(12) United States Patent
Guillemont et al.

(10) Patent No.: US 9,296,760 B2
(45) Date of Patent: Mar. 29, 2016

(54) ANTIBACTERIAL COMPOUNDS

(71) Applicant: JANSSEN SCIENCES IRELAND UC, Little Island, Co Cork (IE)

(72) Inventors: Jerôme Emile Georges Guillemont, Andé (FR); David Francis Alain Lançois, Louviers (FR); Magali Madeleine Simone Motte, Louviers (FR); Wendy Mia Albert Balemans, Kalmthout (BE); Anil Koul, Edegem (BE)

(73) Assignee: Janssen Sciences Ireland UC, Little Island, Co Cork (IE)

( * ) Notice: Subject to any disclaimer, the term of this patent is extended or adjusted under 35 U.S.C. 154(b) by 0 days.

(21) Appl. No.: 14/419,463

(22) PCT Filed: Aug. 9, 2013

(86) PCT No.: PCT/EP2013/066681
§ 371 (c)(1),
(2) Date: Feb. 3, 2015

(87) PCT Pub. No.: WO2014/023815
PCT Pub. Date: Feb. 13, 2014

(65) Prior Publication Data
US 2015/0225424 A1    Aug. 13, 2015

(30) Foreign Application Priority Data

Aug. 10, 2012 (EP) .................... 12180103

(51) Int. Cl.
*C07D 401/06* (2006.01)
*C07D 401/14* (2006.01)
*C07D 405/14* (2006.01)
*C07D 413/14* (2006.01)
*C07D 471/04* (2006.01)
*C07D 498/04* (2006.01)
*C07D 498/14* (2006.01)
*C07D 513/14* (2006.01)

(52) U.S. Cl.
CPC ............ *C07D 513/14* (2013.01); *C07D 401/06* (2013.01); *C07D 401/14* (2013.01); *C07D 405/14* (2013.01); *C07D 413/14* (2013.01); *C07D 471/04* (2013.01); *C07D 498/04* (2013.01); *C07D 498/14* (2013.01)

(58) Field of Classification Search
CPC .. C07D 401/06; C07D 401/14; C07D 405/14; C07D 413/14; C07D 471/04; C07D 498/04; C07D 498/14; C07D 513/14
See application file for complete search history.

(56) References Cited

U.S. PATENT DOCUMENTS

2014/0336153 A1 * 11/2014 Takhi et al. ............... 514/64

FOREIGN PATENT DOCUMENTS

| WO | WO 01/26652 A1 | 4/2001 |
|---|---|---|
| WO | WO 01/26654 A1 | 4/2001 |
| WO | WO 01/27103 A1 | 4/2001 |
| WO | WO 03/088897 A2 | 10/2003 |
| WO | WO 2007/043835 A1 | 4/2007 |
| WO | WO 2007/053131 A2 | 5/2007 |
| WO | WO 2008/098374 A1 | 8/2008 |
| WO | WO 2011/061214 A1 | 5/2011 |

OTHER PUBLICATIONS

Bergler, H., et al., "The Enoyl-[acyl-carrier-protein] Reductase (FabI) of *Escherichia coli*, which Catalyzes a Key Regulatory Step in Fatty Acid Biosynthesis, Accepts NADH and NADPH as Cofactors and is Inhibited by Palmitoyl-CoA", European Journal of Biochemistry, vol. 242, pp. 689-694 (1996).

Bundgaard, H., "Design of Prodrugs: Bioreversible Derivatives for Various Functional Groups and Chemical Entities", Design of Prodrugs, pp. 1-92, Elsevier, New York, Oxford (1985).

Heath, R., et al., "Enoyl-Acyl Carrier Protein Reductdase (fabI) Plays a Determinant Role in Completing Cycles of Fatty Acid Elongation in *Escherichia coli*", The Journal of Biological Chemistry, vol. 270, No. 44, pp. 26538-26542 (1995).

European Search Report dated Dec. 11, 2013 for Application No. EP 12180103.

International Search Report dated Dec. 5, 2013 for Application No. PCT/EP2013/066681.

\* cited by examiner

*Primary Examiner* — Bruck Kifle

(57) ABSTRACT

The present invention is related to novel compounds of formula (I) that may inhibit the activity of the FabI enzyme, and which are useful in the treatment of bacterial infections. It further relates to pharmaceutical compositions comprising these compounds, and chemical processes for preparing these compounds.

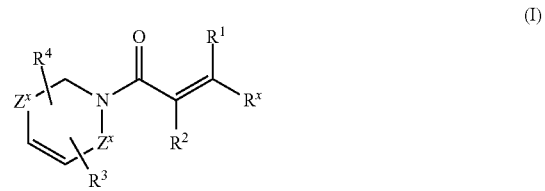

(I)

12 Claims, No Drawings

ANTIBACTERIAL COMPOUNDS

This application is a 35 U.S.C. §371 nationalization of PCT application PCT/EP2013/066681, filed Aug. 9, 2013, which claims priority to European patent application EP 12180103.9, filed Aug. 10, 2012, which are incorporated herein by reference.

The present invention is related to novel compounds of formula (I) that inhibit the activity of the FabI enzyme which are therefore useful in the treatment of bacterial infections. It further relates to pharmaceutical compositions comprising these compounds, and chemical processes for preparing these compounds.

The compounds of the present invention are antibacterial compounds that inhibit the FabI protein, a NADH-dependent enoyl-acyl carrier protein (ACP) reductase enzyme in the fatty acid biosynthesis pathway. Fatty acid synthase (FAS) is involved in the overall biosynthetic pathway of saturated fatty acids in all organisms, but the structural organization of FAS varies considerably among them. The distinctive characteristics of FAS of vertebrates and yeasts are that all enzymatic activities are encoded on one or two polypeptide chains, and that the acyl carrier protein (ACP) exists in the form of a complex. In contrast, in bacterial FAS, each of synthetic steps is catalyzed by a distinct, mono-functional enzyme and the ACP is a discrete protein. Therefore, it is possible to selectively inhibit bacterial FAS by blocking one of the synthetic steps using an inhibitory agent. NADH-dependent enoyl-ACP reductase (Fab I) is involved in the last step of the four reaction steps involved in each cycle of bacterial fatty acid biosynthesis. Thus, the FabI enzyme is the biosynthetic enzyme in the overall synthetic pathway of bacterial fatty acid biosynthesis.

The FabI enzyme has been shown to constitute an essential target in major pathogens such as *E. Coli* (Heath *et al. J. Biol. Chem.* 1995, 270, 26538; Bergler *et al. Eur. J. Biochem.* 1996, 242, 689-694). Hence, compounds that inhibit FabI may be useful as antibacterials.

Compounds having FabI enzyme inhibitory activity have been disclosed in WO-01/26652, WO-01/26654, and WO-01/27103. Substituted naphthyridinone compounds having FabI inhibitory activity have been disclosed in WO-03/088897, WO-2007/043835 and WO-2008/098374. International patent application WO 2007/053131 discloses various compounds for potential use as FabI inhibitors. International patent application WO 2011/061214 also discloses various compounds for potential use as FabI inhibitors. However, none of these documents disclose a double bond-containing nitrogen-based heterocycloalkyl group that is directly attached to a carbonyl moiety that is α to an alkene.

The present invention relates to a compound of formula (I)

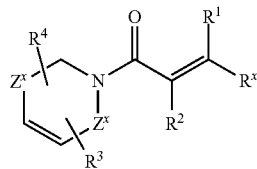

(I)

wherein each $Z^x$ independently represents $—[C(R^{z8})(R^{z9})]_n—$, in which n is 1 or 2; $R^{z8}$ and $R^{z9}$ independently represent hydrogen or a substituent selected from $R^3$ or $R^4$;

$R^1$ is hydrogen, $C_{1-4}$alkyl or halo;
$R^2$ is hydrogen, $C_{1-4}$alkyl or halo;
$R^x$ represents:

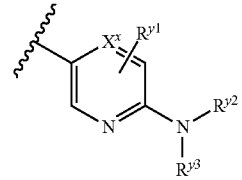

(i)

wherein $X^x$ represents C(H), C($R^{y1}$) or N;

$R^{y1}$ represents one to three optional substituents each independently selected from hydrogen, halo, —CN, —O—$C_{1-6}$ alkyl or $C_{1-6}$ alkyl (which latter two alkyl moieties are optionally substituted by one or more fluoro atoms);

each $R^{y2}$ and $R^{y3}$ independently represent hydrogen or -$Q^1$-$R^5$;

each $Q^1$ independently represents a direct bond or —C(O)—;

$R^5$ represents hydrogen, $C_{1-6}$ alkyl, heterocycloalkyl (which latter two groups are each optionally substituted by one or more substituents independently selected from =O and $Q^2$), aryl or heteroaryl (which latter two groups are optionally substituted by one or more substituents selected from $Q^3$);

$Q^2$ represents halo, —CN, —O$C_{1-6}$ alkyl (optionally substituted by one or more fluoro atoms), aryl or heteroaryl (which latter two groups are optionally substituted by one or more substituents selected from halo, —CN, $C_{1-3}$ alkyl or —O$C_{1-3}$ alkyl, the latter two alkyl moieties being themselves optionally substituted by fluoro);

$Q^3$ represents halo, —CN, —O—$C_{1-6}$ alkyl or $C_{1-6}$ alkyl (which latter two alkyl moieties are optionally substituted by one or more fluoro substituents);

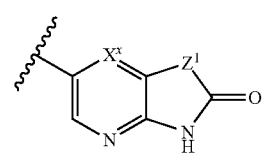

(ii)

wherein $X^x$ represents C(H) or N;

$Z^1$ represents —$X^1$—O—$X^{1a}$—; —$X^2$—N($R^{z3}$)—$X^{2a}$— or —$X^3$—S—$X^{3a}$—;

$X^1$, $X^2$ and $X^3$ independently represent a direct bond, —C(O)— or —C($R^{z4}$)($R^{z5}$)—;

$X^{1a}$, $X^{2a}$ and $X^{3a}$ independently represent a direct bond or —$V^1$—C($R^{z1}$)($R^{z2}$)—;

$V^1$ represents a direct bond or —C(O)—;

$R^{z1}$, $R^{z2}$, $R^{z3}$, $R^{z4}$ and $R^{z5}$ independently represent hydrogen, $C_{1-6}$ alkyl (optionally substituted by one or more substituents selected from =O and halo) or heterocycloalkyl (optionally substituted by one or more substituents selected from =O, halo and $C_{1-3}$ alkyl);

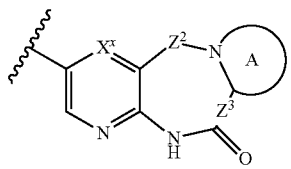

(iii)

wherein $X^x$ represents C(H) or N;

$Z^2$ represents —C($R^{z6}$)($R^{z7}$)— or —C(O)—;

$Z^3$ represents a direct bond (thereby forming a 7-membered ring) or —CH$_2$— (thereby forming an 8-membered ring);

ring A represents a 5- or 6-membered ring optionally containing one, two or three double bonds (and therefore being aromatic or non-aromatic) and optionally containing a further (in addition to the requisite N) one to three (e.g. one or two) heteroatoms (e.g. selected from N and O), and which ring is optionally substituted by one or more substituents each independently selected from =O and $R^{z8}$;

each $R^{z6}$, $R^{z7}$ and $R^{z8}$ independently represents hydrogen or $C_{1-6}$ alkyl optionally substituted by one or more substituents selected from =O, —OC$_{1-4}$ alkyl and halo;

each $R^3$ independently represents hydrogen, halo, —OR$^{10}$ or $C_{1-6}$ alkyl (optionally substituted by one or more halo (e.g. fluoro) atoms);

each $R^4$ independently represents hydrogen, halo or -T$^1$-R$^{20}$;

each $T^1$ independently represents a direct bond, —O—, —C(O)—, —C(O)—O—, —O—C(O)—, —C(O)—N(R$^{21}$)— or —S(O)$_{n1}$—;

n1 represents 0, 1 or 2;

each $R^{10}$ and each $R^{20}$ independently represents $C_{1-6}$ alkyl (optionally substituted by one or more substituents independently selected from =O and $Y^1$), aryl or heteroaryl (which latter two groups are optionally substituted by one or more substituents independently selected from $Y^2$);

$R^{21}$ x represents hydrogen or $C_{1-6}$ alkyl;

each $Y^1$ independently represents halo, —O—R$^{30}$, —CN, aryl or heteroaryl (which latter two groups are optionally substituted by one or more substituents selected from halo, —O—C$_{1-3}$alkyl and $C_{1-3}$ alkyl);

each $Y^2$ independently represents halo, —OC$_{1-6}$alkyl or $C_{1-6}$ alkyl (which latter two alkyl moieties are optionally substituted by one or more fluoro atoms);

each $R^{30}$ independently represents hydrogen, $C_{1-6}$ alkyl (optionally substituted by one or more fluoro atoms), aryl or heteroaryl (which latter two groups are optionally substituted by one or more substituents selected from optionally substituted by one or more substituents selected from halo, —O—C$_{1-3}$alkyl and $C_{1-3}$ alkyl), or a pharmaceutically acceptable salt (e.g. acid addition salt) thereof The above-mentioned compounds of formula (I) (or salts thereof) may be referred to herein as "compounds of the invention".

Pharmaceutically-acceptable salts include acid addition salts and base addition salts. Such salts may be formed by conventional means, for example by reaction of a free acid or a free base form of a compound of formula I with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of the invention in the form of a salt with another counter-ion, for example using a suitable ion exchange resin.

The pharmaceutically acceptable acid addition salts as mentioned hereinabove are meant to comprise the therapeutically active non-toxic acid addition salt forms that the compounds of formula (I) are able to form. These pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

For the purposes of this invention solvates, prodrugs, N-oxides and stereoisomers of compounds of the invention are also included within the scope of the invention.

The term "prodrug" of a relevant compound of the invention includes any compound that, following oral or parenteral administration, is metabolised in vivo to form that compound in an experimentally-detectable amount, and within a predetermined time (e.g. within a dosing interval of between 6 and 24 hours (i.e. once to four times daily)). For the avoidance of doubt, the term "parenteral" administration includes all forms of administration other than oral administration.

Prodrugs of compounds of the invention may be prepared by modifying functional groups present on the compound in such a way that the modifications are cleaved, in vivo when such prodrug is administered to a mammalian subject. The modifications typically are achieved by synthesising the parent compound with a prodrug substituent. Prodrugs include compounds of the invention wherein a hydroxyl, amino, sulfhydryl, carboxy or carbonyl group in a compound of the invention is bonded to any group that may be cleaved in vivo to regenerate the free hydroxyl, amino, sulfhydryl, carboxy or carbonyl group, respectively.

Examples of prodrugs include, but are not limited to, esters and carbamates of hydroxy functional groups, esters groups of carboxyl functional groups, N-acyl derivatives and N-Mannich bases. General information on prodrugs may be found e.g. in Bundegaard, H. "Design of Prodrugs" p. 1-92, Elesevier, N.Y.-Oxford (1985).

Compounds of the invention may contain double bonds and may thus exist as E (entgegen) and Z (zusammen) geometric isomers about each individual double bond. Positional isomers may also be embraced by the compounds of the invention. All such isomers (e.g. if a compound of the invention incorporates a double bond or a fused ring, the cis- and trans-forms, are embraced) and mixtures thereof are included within the scope of the invention (e.g. single positional isomers and mixtures of positional isomers may be included within the scope of the invention).

Compounds of the invention may also exhibit tautomerism. All tautomeric forms (or tautomers) and mixtures thereof are included within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerisations. Valence tautomers include interconversions by reorganisation of some of the bonding electrons.

Compounds of the invention may also contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation (i.e. a 'chiral pool' method), by reaction of the appropriate starting material with a 'chiral auxiliary' which can subsequently be removed at a suitable stage, by derivatisation (i.e. a resolution, including a dynamic resolution), for example with a homochiral acid followed by separation of the diastereomeric derivatives by conventional means such as chromatography, or by reaction with an appropriate chiral reagent or chiral catalyst all under conditions known to the skilled person.

All stereoisomers (including but not limited to diastereoisomers, enantiomers and atropisomers) and mixtures thereof (e.g. racemic mixtures) are included within the scope of the invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds of the present invention may exist in unsolvated as well as solvated forms with pharmaceutically acceptable solvents such as water, ethanol, and the like, and it is intended that the invention embrace both solvated and unsolvated forms.

The present invention also embraces isotopically-labeled compounds of the present invention which are identical to those recited herein, but for the fact that one or more atoms are replaced by an atom having an atomic mass or mass number different from the atomic mass or mass number usually found in nature (or the most abundant one found in nature). All isotopes of any particular atom or element as specified herein are contemplated within the scope of the compounds of the invention. Exemplary isotopes that can be incorporated into compounds of the invention include isotopes of hydrogen, carbon, nitrogen, oxygen, phosphorus, sulfur, fluorine, chlorine and iodine, such as $^{2}H$, $^{3}H$, $^{11}C$, $^{13}C$, $^{14}C$, $^{13}N$, $^{15}O$, $^{17}O$, $^{18}O$, $^{32}P$, $^{33}P$, $^{35}S$, $^{18}F$, $^{36}Cl$, $^{123}I$, and $^{125}I$. Certain isotopically-labeled compounds of the present invention (e.g., those labeled with $^{3}H$ and $^{14}C$) are useful in compound and for substrate tissue distribution assays. Tritiated ($^{3}H$) and carbon-14 ($^{14}C$) isotopes are useful for their ease of preparation and detectability. Further, substitution with heavier isotopes such as deuterium (i.e., $^{2}H$ may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$ and $^{18}F$ are useful for positron emission tomography (PET) studies to examine substrate receptor occupancy. Isotopically labeled compounds of the present invention can generally be prepared by following procedures analogous to those disclosed in the Scheme 1 and/or in the Examples herein below, by substituting an isotopically labeled reagent for a non-isotopically labeled reagent.

Unless otherwise specified, $C_{1-q}$ alkyl groups (where q is the upper limit of the range) defined herein may be straight-chain or, when there is a sufficient number (i.e. a minimum of two or three, as appropriate) of carbon atoms, be branched-chain, and/or cyclic (so forming a $C_{3-q}$-cycloalkyl group). Such cycloalkyl groups may be monocyclic or bicyclic and may further be bridged. Further, when there is a sufficient number (i.e. a minimum of four) of carbon atoms, such groups may also be part cyclic. Such alkyl groups may also be saturated or, when there is a sufficient number (i.e. a minimum of two) of carbon atoms, be unsaturated (forming, for example, a $C_{2-q}$ alkenyl or a $C_{2-q}$ alkynyl group).

$C_{3-q}$ cycloalkyl groups (where q is the upper limit of the range) that may be specifically mentioned may be monocyclic or bicyclic alkyl groups, which cycloalkyl groups may further be bridged (so forming, for example, fused ring systems such as three fused cycloalkyl groups). Such cycloalkyl groups may be saturated or unsaturated containing one or more double bonds (forming for example a cycloalkenyl group). Substituents may be attached at any point on the cycloalkyl group. Further, where there is a sufficient number (i e a minimum of four) such cycloalkyl groups may also be part cyclic.

The term "halo", when used herein, preferably includes fluoro, chloro, bromo and iodo.

Heterocycloalkyl groups that may be mentioned include non-aromatic monocyclic and bicyclic heterocycloalkyl groups in which at least one (e.g. one to four) of the atoms in the ring system is other than carbon (i.e. a heteroatom), and in which the total number of atoms in the ring system is between 3 and 20 (e.g. between three and ten, e.g between 3 and 8, such as 5- to 8-). Such heterocycloalkyl groups may also be bridged. Further, such heterocycloalkyl groups may be saturated or unsaturated containing one or more double and/or triple bonds, forming for example a $C_{2-q}$ heterocycloalkenyl (where q is the upper limit of the range) group. $C_{2-q}$ heterocycloalkyl groups that may be mentioned include 7-azabicyclo[2.2.1]heptanyl, 6-azabicyclo[3.1.1]heptanyl, 6-azabicyclo[3.2.1]-octanyl, 8-azabicyclo-[3.2.1]octanyl, aziridinyl, azetidinyl, dihydropyranyl, dihydropyridyl, dihydropyrrolyl (including 2,5-dihydropyrrolyl), dioxolanyl (including 1,3-dioxolanyl), dioxanyl (including 1,3-dioxanyl and 1,4-dioxanyl), dithianyl (including 1,4-dithianyl), dithiolanyl (including 1,3-dithiolanyl), imidazolidinyl, imidazolinyl, morpholinyl, 7-oxabicyclo[2.2.1]-heptanyl, 6-oxabicyclo-[3.2.1]octanyl, oxetanyl, oxiranyl, piperazinyl, piperidinyl, non-aromatic pyranyl, pyrazolidinyl, pyrrolidinonyl, pyrrolidinyl, pyrrolinyl, quinuclidinyl, sulfolanyl, 3-sulfolenyl, tetrahydropyranyl, tetrahydrofuranyl, tetrahydropyridyl (such as 1,2,3,4-tetrahydropyridyl and 1,2,3,6-tetrahydropyridyl), thietanyl, thiiranyl, thiolanyl, thiomorpholinyl, trithianyl (including 1,3,5-trithianyl), tropanyl and the like. Substituents on heterocycloalkyl groups may, where appropriate, be located on any atom in the ring system including a heteroatom. The point of attachment of heterocycloalkyl groups may be via any atom in the ring system including (where appropriate) a heteroatom (such as a nitrogen atom), or an atom on any fused carbocyclic ring that may be present as part of the ring system. Heterocycloalkyl groups may also be in the N- or S-oxidised form. Heterocycloalkyl mentioned herein may be stated to be specifically monocyclic or bicyclic.

Aryl groups that may be mentioned include $C_{6-20}$, such as $C_{6-12}$ (e.g. $C_{6-10}$) aryl groups. Such groups may be monocyclic, bicyclic or tricyclic and have between 6 and 12 (e.g. 6 and 10) ring carbon atoms, in which at least one ring is aromatic. $C_{6-10}$ aryl groups include phenyl, naphthyl and the like, such as 1,2,3,4-tetrahydronaphthyl. The point of attachment of aryl groups may be via any atom of the ring system. For example, when the aryl group is polycyclic the point of attachment may be via atom including an atom of a non-aromatic ring. However, when aryl groups are polycyclic (e.g. bicyclic or tricyclic), they are preferably linked to the rest of the molecule via an aromatic ring. Most preferred aryl groups that may be mentioned herein are "phenyl".

Unless otherwise specified, the term "heteroaryl" when used herein refers to an aromatic group containing one or more heteroatom(s) (e.g. one to four heteroatoms) preferably selected from N, O and S. Heteroaryl groups include those which have between 5 and 20 members (e.g. between 5 and 10) and may be monocyclic, bicyclic or tricyclic, provided that at least one of the rings is aromatic (so forming, for example, a mono-, bi-, or tricyclic heteroaromatic group). When the heteroaryl group is polycyclic the point of attachment may be via any atom including an atom of a non-aromatic ring. However, when heteroaryl groups are polycyclic (e.g. bicyclic or tricyclic), they are preferably linked to the rest of the molecule via an aromatic ring. Heteroaryl groups that may be mentioned include 3,4-dihydro-1H-isoquinolinyl, 1,3-dihydroisoindolyl, 1,3-dihydroisoindolyl (e.g. 3,4-dihydro-1H-isoquinolin-2-yl, 1,3-dihydroisoindol-2-yl, 1,3-dihydroisoindol-2-yl; i.e. heteroaryl groups that are linked via a non-aromatic ring), or, preferably, acridinyl, benzimidazolyl, benzodioxanyl, benzodioxepinyl, benzodioxolyl (including 1,3-benzodioxolyl), benzofuranyl, benzofurazanyl, benzothiadiazolyl (including 2,1,3-benzothiadiazolyl), benzothiazolyl, benzoxadiazolyl (including 2,1,3-benzoxadiazolyl), benzoxazinyl (including 3,4-dihydro-2H-1,4-benzoxazinyl), benzoxazolyl, benzomorpholinyl, benzoselenadiazolyl (including 2,1,3-benzoselenadiazolyl), benzothienyl, carbazolyl, chromanyl, cinnolinyl, furanyl, imidazolyl, imidazo[1,2-a]pyridyl, indazolyl, indolinyl, indolyl, isobenzofuranyl, isochromanyl, isoindolinyl, isoindolyl, isoquinolinyl, isothiazolyl, isothiochromanyl, isoxazolyl, naphthyridinyl (including 1,6-naphthyridinyl or, preferably, 1,5-naphthyridinyl and 1,8-naphthyridinyl), oxadiazolyl (including 1,2,3-oxadiazolyl, 1,2,4-oxadiazolyl and 1,3,4-oxadiazolyl), oxazolyl, phenazinyl, phenothiazinyl, phthalazinyl, pteridinyl, purinyl, pyranyl, pyrazinyl, pyrazolyl, pyridazinyl, pyridyl, pyrimidinyl, pyrrolyl, quinazolinyl, quinolinyl, quinolizinyl, quinoxalinyl, tetrahydroisoquinolinyl (including 1,2,3,4-tetrahydroisoquinolinyl and 5,6,7,8-tetrahydroisoquinolinyl), tetrahydroquinolinyl (including 1,2,3,4-tetrahydroquinolinyl and 5,6,7,8-tetrahydroquinolinyl), tetrazolyl, thiadiazolyl (including 1,2,3-thiadiazolyl, 1,2,4-thiadiazolyl and 1,3,4-thiadiazolyl), thiazolyl, thiochromanyl, thiophenetyl, thienyl, triazolyl (including 1,2,3-triazolyl, 1,2,4-triazolyl and 1,3,4-triazolyl) and the like. Substituents on heteroaryl groups may, where appropriate, be located on any atom in the ring system including a heteroatom. The point of attachment of heteroaryl groups may be via any atom in the ring system including (where appropriate) a heteroatom (such as a nitrogen atom), or an atom on any fused carbocyclic ring that may be present as part of the ring system. Heteroaryl groups may also be in the N- or S-oxidised form. Heteroaryl groups mentioned herein may be stated to be specifically monocyclic or bicyclic. When heteroaryl groups are polycyclic in which there is a non-aromatic ring present, then that non-aromatic ring may be substituted by one or more =O group. Most preferred heteroaryl groups that may be mentioned herein are 5- or 6-membered aromatic groups containing 1, 2 or 3 heteroatoms (e.g. preferably selected from nitrogen, oxygen and sulfur).

It may be specifically stated that the heteroaryl group is monocyclic or bicyclic. In the case where it is specified that the heteroaryl is bicyclic, then it may consist of a five-, six- or seven-membered monocyclic ring (e.g. a monocyclic heteroaryl ring) fused with another five-, six- or seven-membered ring (e.g. a monocyclic aryl or heteroaryl ring).

Heteroatoms that may be mentioned include phosphorus, silicon, boron and, preferably, oxygen, nitrogen and sulfur.

For the avoidance of doubt, where it is stated herein that a group (e.g. a $C_{1-6}$ alkyl group) may be substituted by one or more substituents (e.g. selected from $Y^1$), then those substituents (e.g. defined by $Y^1$) are independent of one another. That is, such groups may be substituted with the same substituent (e.g. defined by $Y^1$) or different substituents (defined by $Y^1$).

All individual features (e.g. preferred features) mentioned herein may be taken in isolation or in combination with any other feature (including preferred feature) mentioned herein (hence, preferred features may be taken in conjunction with other preferred features, or independently of them).

The skilled person will appreciate that compounds of the invention that are the subject of this invention include those that are stable. That is, compounds of the invention include those that are sufficiently robust to survive isolation from e.g. a reaction mixture to a useful degree of purity.

The term "FabI" is art-recognized and refers to the bacterial enzyme believed to function as an enoyl-acyl carrier protein (ACP) reductase in the final step of the four reactions involved in each cycle of bacterial fatty acid biosynthesis. This enzyme is believed to be widely distributed in bacteria.

For the avoidance of doubt, the following compounds of formula (I) (given sub-definitions (Ia), (Ib) and (Ic)) are within the scope of the invention:

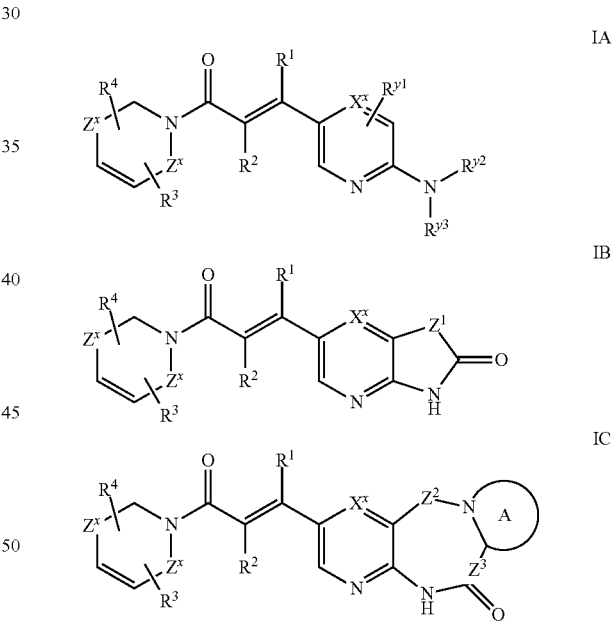

in which the integers are as hereinbefore defined. For the avoidance of doubt that $R^3$ and $R^4$ substituents are optional (given that they are depicted as "floating" and that each can represent hydrogen). When the $R^3$ and $R^4$ group represent a substituent other than hydrogen, then each may be placed at any position on the $Z^x$-containing ring, including on $Z^x$ itself, although preferably the $R^3/R^4$ (e.g. $R^4$) group is attached to the requisite double bond.

Preferred compounds of the invention include those in which:

when $R^1$ or $R^2$ represent halo, then they are preferably F or Cl;
more preferably, $R^1$ represents hydrogen or $C_{1-4}$alkyl;
more preferably, $R^2$ represents hydrogen or $C_{1-4}$alkyl.

Compounds of the invention that may be mentioned include those in which, when $R^x$ represents either ring (i), (ii) or (iii), then those rings represent:

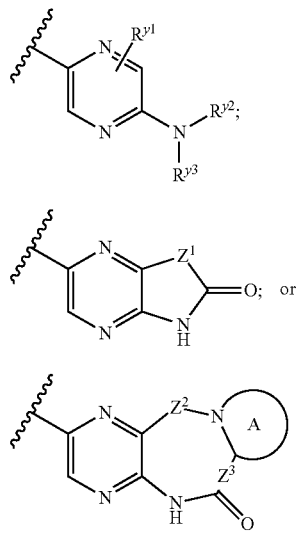

i.e. all are rings in which the monocycle or the first (aromatic) ring of the bicycle or tricycle (which is attached to the remainder of the compound of formula I) contains two nitrogen atoms (in a 1,4-relationship) and wherein the remainder of the integers are as defined herein. However, in an embodiment of the invention (for instance a preferred embodiment), compounds of the invention that may be mentioned include those in which:
when $R^x$ represents either ring (i), (ii) or (iii), then those rings represent

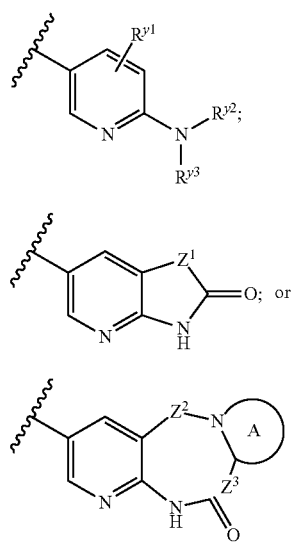

wherein (in each case), the integers are as herein defined. Hence, it is preferred that the rings are those in which $X^x$ represents C.

Preferred compounds of the invention include those in which:

each $Z^x$ independently represents —[C($R^{z8}$)($R^{z9}$)]$_n$—, in which n is 1 or 2, but it is preferred that there are not two $Z^x$ groups in which n is 2 (i.e. it is preferred that the $Z^x$-containing ring is 6- or 7-membered);

each $Z^x$ represents —C($R^{z8}$)($R^{z9}$)— (so forming a 6-membered ring) or either one $Z^x$ moiety represents —C($R^{z8}$)($R^{z9}$)—C($R^{z8}$)($R^{z9}$)— and the other represents —C($R^{z8}$)($R^{z9}$)— (so forming a 7-membered ring);

each $Z^x$ represents —$CH_2$— (so forming a 6-membered ring) or one $Z^x$ represents —$CH_2CH_2$— and the other represents —$CH_2$— (so forming a 7-membered ring);

$R^3$ represents hydrogen, halo, —$OCH_3$, —$OCF_3$ or $C_{1-2}$ alkyl (more preferably $R^3$ represents hydrogen, i.e. is not present);

each $R^{10}$ represents $C_{1-6}$ alkyl (e.g. $C_{1-3}$ alkyl), which may be substituted by one or more halo atoms, but which is preferably unsubstituted;

there is 0 or 1 (preferably 0) $R^3$ substituents present on the $Z^x$-containing ring (i.e. $R^3$ preferably represents hydrogen);

there is 1 or 2 (preferably 1) $R^4$ substituent(s) presents on the $Z^x$-containing ring, for instance attached to either one of the ends of the requisite double bond.

Hence, the preferred $Z^x$-containing rings are:

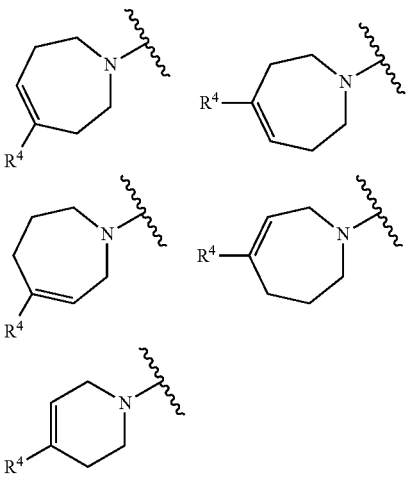

The most preferred $Z^x$-containing ring is:

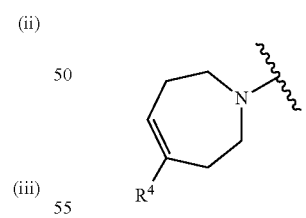

The presence of the double bond in the $Z^x$-containing ring may help to orient the $R^4$ group (if present) such that the compound overall (e.g. in view of the $R^4$ substituent's orientation) displays better/improved binding properties to the FabI bacterial enzyme. Hence, these compounds of the invention may be advantageous in the sense that the presence of the double bond may lead to improved binding to/inhibition of the FabI enzyme. Consequently the compounds of the invention may be advantageous compounds (e.g. compared to known compounds) by virtue of these properties which may consequentially lead to better potency, efficacy, etc.

Preferred compounds of the invention hence include those in which:

when $R^4$ represents a substituent attached to either end of the requisite double bond, then $R^4$ preferably represents a substituent other than hydrogen (i.e. halo or -$T^1$-$R^{20}$), for example, in this context $R^4$ preferably represents -$T^1$-$R^4$;

it is preferred that there is at least one $R^4$ substituent present that represents -$T^1$-$R^4$ (which is attached to either one of the ends of the requisite double bond) in which $R^4$ represents -$T^1$-$R^4$.

Preferred compounds of the invention include those in which there is an $R^4$ substituent present attached to either end of the double bond and, in this context, $R^4$ represents -$T^1$-$R^{20}$. In this context, it is preferred that:

each $Y^2$ independently represents halo or —O—$C_{1-3}$alkyl (optionally substituted by fluoro);

each $Y^2$ independently represents halo, —O—$C_{1-3}$alkyl or $C_{1-3}$ alkyl (which latter two groups are optionally substituted by fluoro);

each $R^{30}$ independently represents hydrogen or $C_{1-4}$ (e.g. $C_{1-3}$) alkyl;

when $Y^1$ represents aryl or heteroaryl, then these groups preferably represent those hereinbefore defined (e.g. phenyl or a 5- or 6-membered aromatic group containing 1, 2 or 3 heteroatoms), which aryl or heteroaryl groups are optionally substituted by one or more substituents selected from halo, —OCH$_3$ and CH$_3$ (but which are preferably unsubstituted);

$T^1$ represents —O—, —C(O)— or, preferably, a direct bond;

$R^{20}$ most preferably represents aryl or heteroaryl, both of which are optionally substituted by one or more substituents selected from $Y^2$;

when $R^{20}$ represents aryl, it preferably represents optionally substituted phenyl (e.g. unsubstituted or substituted in which the optional substituents are selected from halo (e.g. fluoro), —O$C_{1-2}$ alkyl (e.g. —OCH$_3$));

when $R^{20}$ represents heteroaryl, it preferably represents an optionally substituted 5- or 6-membered monocyclic aromatic group containing 1, 2 or 3 (e.g. one) heteroatom(s) (e.g. preferably selected from nitrogen, oxygen and sulfur).

Preferred $R^{20}$ groups include phenyl and 5- or 6-membered monocyclic heteroaryl groups containing one to four heteroatoms (and preferably containing one or two heteroatoms), so forming for example thienyl, pyridyl, thiazolyl, oxazolyl, isoxazolyl, pyrazolyl or the like. Particularly preferred $R^{20}$ groups include phenyl, thienyl, thiazolyl, pyridyl and pyrazolyl, all of which are optionally substituted as defined herein. Especially preferred $R^{20}$ groups include phenyl (e.g. unsubstituted phenyl, 2-methoxy-5-fluoro-phenyl) and thienyl (e.g. 2-thienyl).

$R^4$ may represent the following:

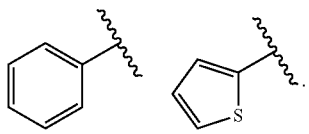 [SMILES: *c1ccccc1 ; *c1cccs1]

Further preferred compounds of the invention include those in which, for compounds of the invention in which $R^x$ represents option (i):

there are no $R^{y1}$ groups present (or there is one $R^{y1}$ group present that represents hydrogen) or there is one $R^{y1}$ substituent present that represents —CN, —O—$C_{1-6}$ alkyl (e.g. —O—$C_{1-3}$ alkyl such as —OCH$_3$) or $C_{1-6}$ alkyl (e.g. $C_{1-3}$ alkyl such as methyl);

both $R^{y2}$ and $R^{y3}$ represent -$Q^1$-$R^5$ or, more preferably, one of $R^{y2}$ and $R^{y3}$ represents hydrogen and the other represents -$Q^1$-$R^5$;

$Q^1$ represents a direct bond or preferably —C(O)—;

$R^5$ represents hydrogen, $C_{1-6}$ alkyl (optionally substituted by one or two (e.g. one) substituent(s) selected from =O and $Q^2$), a 5- or 6-membered heterocycloalkyl group (containing one or two heteroatoms; optionally substituted by one or two substituents selected from =O and $Q^2$) or aryl or heteroaryl (which latter two groups are optionally substituted by one or two (e.g. one) substituent(s) selected from $Q^3$);

when $R^5$ represents $C_{1-6}$ alkyl, it is preferably unsubstituted (e.g. —CH$_3$, isopropyl, tert-butyl or isobutyl) or substituted by one or more $Q^2$ substituents (so forming e.g. —CF$_3$) or it is a cycloalkyl group optionally branched (e.g. cyclopropyl substituted by methyl, or, unsubstituted cyclopentyl, cyclohexyl);

when $R^5$ represents optionally substituted heterocycloalkyl, then it is preferably optionally substituted 5- or 6-membered heterocycloalkyl group containing one or two (e.g. one) heteroatom(s) (preferably selected from oxygen, nitrogen and sulfur), so forming e.g. a tetrahydrofuranyl group (e.g. a 2- or 3-tetrahydrofuranyl group); when $R^5$ represents optionally substituted aryl, then it is preferably unsubstituted phenyl;

when $R^5$ represents optionally substituted heteroaryl, then it is preferably a 5- or 6-membered aromatic group containing 1, 2 or 3 (e.g. one) heteroatom(s) (preferably selected from oxygen, nitrogen and sulfur), so forming for example pyridyl (such as 3-pyridyl, 4-pyridyl or 2-pyridyl), furanyl (e.g. 3-furanyl), pyrazolyl (e.g. 4-pyrazolyl, 5-pyrazolyl), imidazolyl (e.g. 4-imidazolyl), oxazolyl (e.g. 3-oxazolyl) or pyrazinyl (e.g. 2-pyrazinyl);

$Q^2$ represents halo (e.g. fluoro), —O$C_{1-3}$ alkyl or optionally substituted aryl or optionally substituted heteroaryl (e.g. pyridyl, such as 4-pyridyl);

$Q^3$ represents halo (e.g. chloro, fluoro, bromo or iodo), $C_{1-6}$ (e.g. $C_{1-3}$) alkyl (e.g. methyl) or —O$C_{1-6}$ alkyl (e.g. —O$C_{1-3}$ alkyl such as —OCH$_3$).

In a particularly preferred aspect of the invention one of $R^{y2}$ and $R^{y3}$ represents hydrogen and the other represents -$Q^1$-$R^5$, in which:

(i) $R^5$ may represent hydrogen, $C_{1-6}$ alkyl as defined herein. In this aspect of the invention it is particularly preferred that the $C_{1-6}$ alkyl group is substituted with a $Q^2$ group, in which $Q^2$ represents optionally substituted aryl or heteroaryl, as defined herein;

(ii) $R^5$ represents optionally substituted aryl or heteroaryl, as defined herein.

The -$Q^1$-$R^5$ moiety may represent hydrogen (and hence the —N($R^{y2}$)($R^{y3}$) may represent —NH$_2$). However, preferred -$Q^1$- moieties include —C(O)—, and preferred $R^5$ groups include hydrogen, —CH$_3$, —CF$_3$, -isopropyl, tert-butyl, isobutyl (—CH$_2$—C(H)(CH$_3$)$_2$), cyclopentyl, -(cyclopropyl)(methyl), cyclohexyl and the following groups:

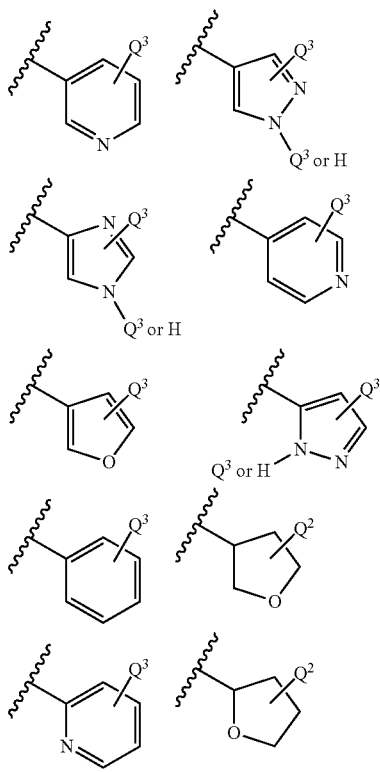

in which the "floating" $Q^2$ or $Q^3$ substituent represents one or more substituents on the ring, as defined herein by $Q^2$ or $Q^3$ (as appropriate).

In particular, the preferred $-Q^1-R^5$ groups are those that contain an aromatic ring.

Further preferred compounds of the invention include those in which, for compounds of the invention in which $R^x$ represents option (ii):

$Z^1$ represents $-X^3-S-X^{3a}-$ or, more preferably, $-X^1-O-X^{1a}-$ or $-X^2-N(R^{z3})-X^{2a}-$;

$X^1$ represents $-C(R^{z4})(R^{z5})-$ or a direct bond;

$X^{1a}$ represents a direct bond or $-C(R^{z1})(R^{z2})-$ $X^2$ represents a direct bond, $-C(O)-$ or $-C(R^{z4})(R^{z5})-$;

$X^{2a}$ represents $-C(R^{z1})(R^{z2})-$ or $-C(O)-C(R^{z1})(R^{z2})-$;

$Z^1$ represents:
  (i) $-X^1-O-X^{1a}-$, in which one of $X^1$ represents $-C(R^{z4})(R^{z5})-$ and $X^{1a}$ represents a direct bond, or, $X^1$ represents a direct bond and $X^{1a}$ represents $-C(R^{z1})(R^{z2})-$;
  (ii) $-X^1-O-X^{1a}-$ or $-X^2-N(R^{z3})-X^{2a}-$, in which each of $X^1$ and $X^2$ represents $-C(R^{z4})(R^{z5})-$ and each of $X^{1a}$ and $X^{2a}$ represents $-C(R^{z1})(R^{z2})-$;
  (iii) $-X^2-N(R^{z3})-X^{2a}-$, in which $X^2$ represents $-C(O)-$ and $X^{2a}$ represents $-C(R^{z1})(R^{z2})-$; or
  (iv) $-X^2-N(R^{z3})-X^{2a}-$, in which $X^2$ represents a direct bond and $X^{2a}$ represents $-C(O)-C(R^{z1})(R^{z2})$;

$R^{z3}$ represents hydrogen, $C_{1-4}$ alkyl (e.g. methyl), $-S(O)_2C_{1-2}$ alkyl (e.g. $-S(O)_2CH_3$), $-C(O)-C_{1-2}$ alkyl (e.g. $-C(O)CH_3$);

each $R^{z1}$, $R^{z2}$, $R^{z4}$ and $R^{z5}$ independently represents hydrogen, $C_{1-4}$ alkyl (e.g. methyl or isopropyl) or heterocycloalkyl (e.g. a 5- or 6-membered heterocycloalkyl group containing one or two (e.g. one) heteroatoms (preferably selected from nitrogen, oxygen and sulfur), and which is preferably attached via a carbon atom, e.g. unsubstituted 4-piperidinyl);

$Z^1$ preferably represents $-CH_2-O-$, $-O-CH_2-$, $-O-C(CH_3)_2-$, $-CH_2-N(H)-CH_2$, $-CH_2-O-CH_2-$, $-CH_2-N(CH_3)-CH_2$, $-O-C(H)(isopropyl)-$, $-C(O)-N(H)-CH_2$, $-N(H)-C(O)-C(CH_3)_2-$ or $-O-C(H)(4-piperidinyl)$.

When $R^x$ represents option (ii), the preferred groups are

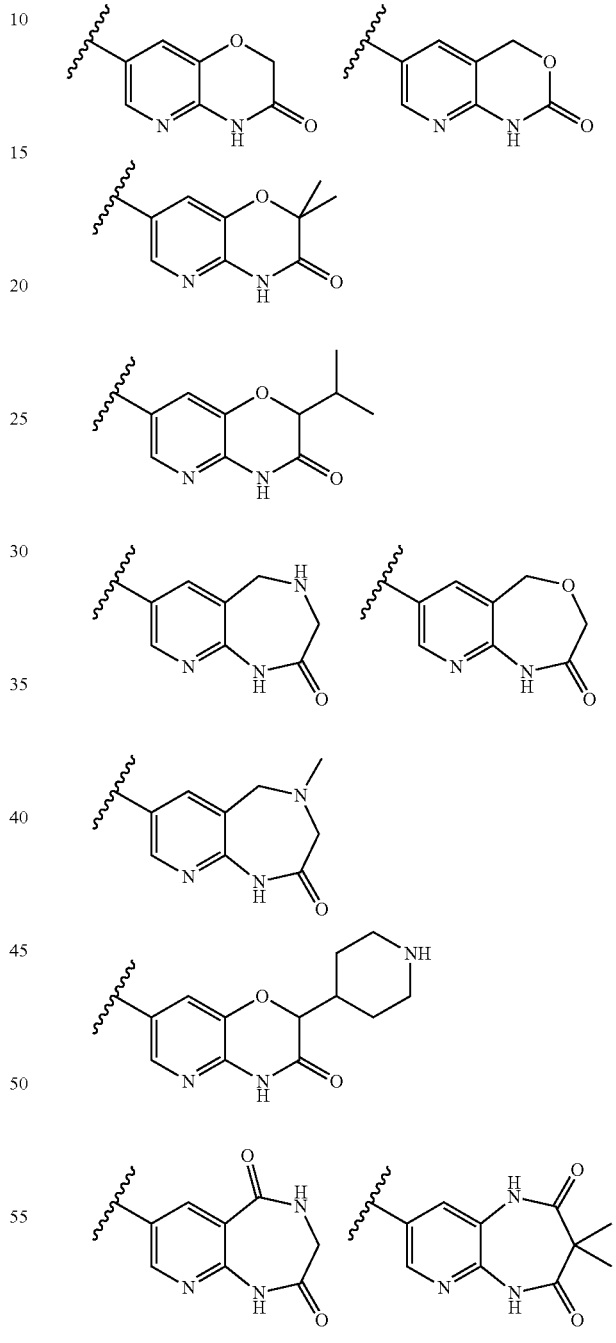

in which the bicycles may be optionally substituted as defined herein. In some structures, optional substituents are depicted (e.g. methyl, isopropyl, piperidinyl), and hence the $R^x$ groups depicted above are preferably of that exact structure (i.e. unsubstituted if depicted as such or substituted with the specific substituents as indicated).

Particularly preferred groups when R^x represents option (ii) include:

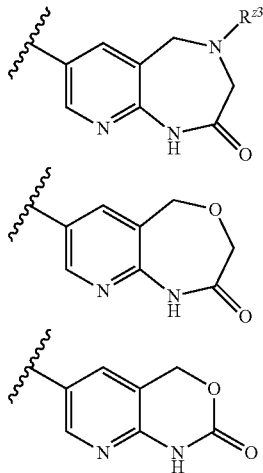

Further preferred compounds of the invention include those in which, for compounds of the invention in which R^x represents option (iii):
$Z^2$ represents —C($R^{z6}$)($R^{z7}$)— or —C(O)—;
$Z^3$ represents a direct bond or —CH$_2$—;
the $Z^2$ and $Z^3$-containing ring is one in which:
(i) $Z^2$ represents —C($R^{z6}$)($R^{z7}$)— and $Z^3$ represents a direct bond;
(ii) $Z^2$ represents —C($R^{z6}$)($R^{z7}$)— and $Z^3$ represents —CH$_2$—;
(iii) $Z^2$ represents —C(O)— and $Z^3$ represents a direct bond;
$R^{z6}$ and $R^{z7}$ independently represent hydrogen;
$R^{z8}$ represents hydrogen (i.e. the A ring is further unsubstituted) or $C_{1-6}$ (e.g. $C_{1-4}$) alkyl (e.g. ethyl) optionally substituted by =O and –O—$C_{1-4}$ alkyl, so forming e.g. a —C(O)—CH$_3$ group, —C(O)—OCH$_2$CH$_3$ group or a —C(O)O-tert-butyl group; the "A" ring is one which preferably represents:
(i) a 5- or 6-membered heterocycloalkyl group optionally containing one further heteroatom (e.g. nitrogen, oxygen or sulphur), so forming e.g. morpholinyl, thiomorpholinyl, piperidinyl or piperazinyl;
(ii) a 5- or 6-membered heteroaryl ring optionally containing one or two further heteroatoms (e.g. selected from nitrogen, oxygen and sulfur), so forming e.g. imidazolyl, triazolyl (e.g. 1,2,4-triazolyl) or pyrazolyl.

When R^x represents option (iii), the preferred groups are

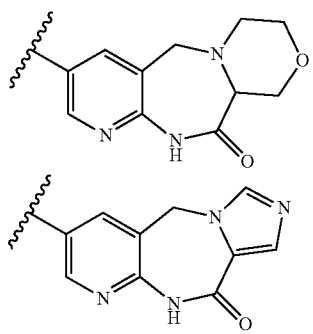

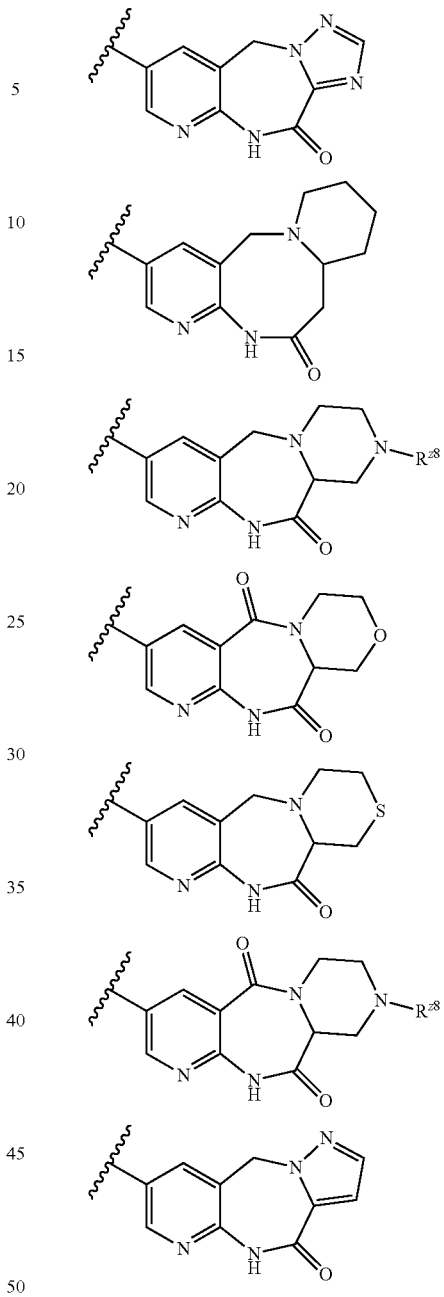

in which the tricycles may be optionally substituted as defined herein. However, preferably the R^x groups are exactly as those depicted above, i.e. further unsubstituted or specific substituents as depicted (e.g. by $R^{z8}$).

Particularly preferred groups when R^x represents option (ii) include:

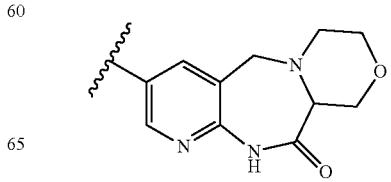

-continued

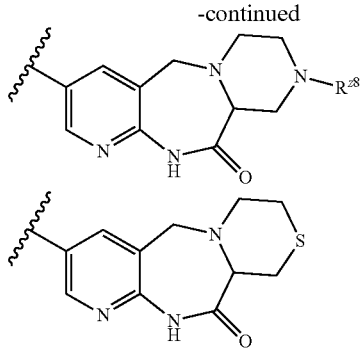

Compounds of formula (I) may be prepared by:
(i) reaction of a compound of formula (II),

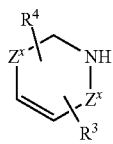
(II)

wherein $Z^x$, $R^3$ and $R^4$ are as hereinbefore defined, with a compound of formula (III),

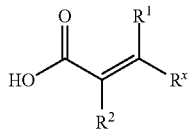
(III)

wherein $R^1$, $R^2$ and $R^x$ are as hereinbefore defined, for example under coupling reaction conditions, for example in the presence of a suitable coupling reagent (e.g. 1,1'-carbonyldiimidazole, N,N'-dicyclohexyl-carbodiimide, 1-(3-dimethylaminopropyl)-3-ethylcarbodiimide (or hydrochloride thereof), N,N'-disuccinimidyl carbonate, benzotriazol-1-yloxytris(dimethylamino) phosphonium hexafluoro-phosphate, 2-(1H-benzotriazol-1-yl)-1,1,3,3-tetramethyluronium hexa-fluorophosphate (i.e. O-(1H-benzotriazol-1-yl)-N,N,N',N'-tetramethyluronium hexafluorophosphate), benzotriazol-1-yloxytris-pyrrolidinophosphonium hexa-fluorophosphate, bromo-tris-pyrrolidinophosponium hexafluorophosphate, 2-(1H-benzotriazol-1-yl)-1, 1,3,3-tetramethyluronium tetra-fluorocarbonate, 1-cyclohexylcarbodiimide-3-propyloxymethyl polystyrene, O-(7-azabenzotriazol-1-yl)-N,N,N',N'-tetramethyluronium hexafluorophosphate, O-benzotriazol-1-yl-N,N, N',N'-tetramethyluronium tetrafluoroborate), optionally in the presence of a suitable base (e.g. sodium hydride, sodium bicarbonate, potassium carbonate, pyridine, triethylamine, dimethylaminopyridine, diisopropylamine, sodium hydroxide, potassium tert-butoxide and/or lithium diisopropylamide (or variants thereof) and an appropriate solvent (e.g. tetrahydrofuran, pyridine, toluene, dichloromethane, chloroform, acetonitrile, dimethylformamide, trifluoromethyl-benzene, dioxane or triethylamine) Such reactions may be performed in the presence of a further additive such as 1-hydroxybenzo-triazole hydrate. Alternatively, a carboxylic acid group may be converted under standard conditions to the corresponding acyl chloride (e.g. in the presence of SOCl$_2$ or oxalyl chloride), which acyl chloride is then reacted with a compound of formula (II), for example under similar conditions to those mentioned above. Alternatively still, when a carboxylic acid ester group is converted to a carboxylic acid amide, the reaction may be performed in the presence of a suitable reagent such as trimethylaluminium (and the relevant compound of formula (II));

(ii) reaction of a compound of formula (IV),

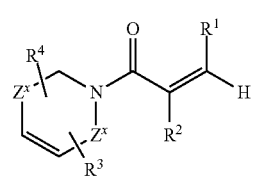
(IV)

wherein $Z^x$, $R^3$, $R^4$, $R^1$ and $R^2$ are as hereinbefore defined, with a compound of formula (V), $$X^{a1}-R^x \quad (V)$$

wherein $X^{a1}$ represents a suitable leaving group, such as a suitable halo group (e.g. chloro, iodo and, especially, bromo), under reaction suitable reaction conditions, for example under metal catalyst coupling reaction conditions (e.g. precious metal coupling reaction conditions, wherein the precious metal is e.g. palladium-based), in particular under Heck reaction conditions using preferably a palladium-based catalyst such as palladium acetate, tetrakis(triphenylphosphione)palladium(0), bis (triphenylphosphine)-palladium(II) dichloride, [1,1'-bis (diphenylphosphino)ferrocene]-palladium(II) dichloride or the like (preferably, the catalyst is palladium acetate), for instance optionally in the presence of a suitable solvent (e.g. acetonitrile or the like), base (e.g. an amine base such as N,N-diisopropyl-amine or the like), and a ligand (e.g. triphenylphosphine, tri-O-tolylphosphine or the like). The reaction may be performed in a sealed tube and/or in a microwave;

(iii) modification of existing compounds of formula (I), for example by conversions of/to standard function groups (e.g. conversion of a —N(H)— moiety to a —N(—C (O)-alkyl)- moiety by acylation, etc).

Compounds of formula (II) in which there is a aromatic $R^4$ substituent attached to either end of the requisite double bond, may be prepared by reaction of a compound of formula (VI),

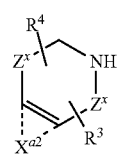
(VI)

or a protected derivative thereof (e.g. an amino-protected derivative, e.g. —N-Boc derivative), wherein $X^{a2}$ is attached to either end of the requisite double bond and represents a suitable leaving group, such as such as iodo, bromo, chloro or a sulfonate group (e.g. —OS(O)$_2$CF$_3$, a nonaflate or the like), and Z$^x$, R$^3$ and R$^4$ are as hereinbefore defined, with a compound of formula (VII),

  (VII)

wherein Ar represents an aromatic group (aryl or heteroaryl) that R$^4$ may represent, and X$^{a3}$ represents a suitable group, such as —B(OH)$_2$, —B(OR$^{wx}$)$_2$ or —Sn(R$^{wx}$)$_3$, in which each R$^{wx}$ independently represents a C$_{1-6}$ alkyl group, or, in the case of —B(OR')$_2$, the respective R$^{wx}$ groups may be linked together to form a 4- to 6-membered cyclic group (such as a 4,4,5,5-tetramethyl-1,3,2-dioxaborolan-2-yl group), thereby forming e.g. a pinacolato boronate ester group. The reaction may be performed in the presence of a suitable catalyst system, e.g. a metal (or a salt or complex thereof) such as Pd, CuI, Pd/C, PdCl$_2$, Pd(OAc)$_2$, Pd(Ph$_3$P)$_2$Cl$_2$, Pd(Ph$_3$P)$_4$ (i.e. palladium tetrakistriphenyl-phosphine), Pd$_2$(dba)$_3$ and/or NiCl$_2$ (preferred catalysts include palladium) and optionally a ligand such as PdCl$_2$(dppf).DCM, t-Bu$_3$P, (C$_6$H$_{11}$)$_3$P, Ph$_3$P, AsPh$_3$, P(o-Tol)$_3$, 1,2-bis(diphenylphosphino)ethane, 2,2'-bis(di-tert-butylphosphino)-1,1'-biphenyl, 2,2'-bis(diphenylphosphino)-1,1'-bi-naphthyl, 1,1'-bis(diphenyl-phosphino-ferrocene), 1,3-bis(diphenylphosphino)propane, xantphos, or a mixture thereof, together with a suitable base such as, Na$_2$CO$_3$, K$_3$PO$_4$, Cs$_2$CO$_3$, NaOH, KOH, K$_2$CO$_3$, CsF, Et$_3$N, (i-Pr)$_2$NEt, t-BuONa or t-BuOK (or mixtures thereof; preferred bases include Na$_2$CO$_3$ and K$_2$CO$_3$) in a suitable solvent such as dioxane, toluene, ethanol, dimethylformamide, dimethoxyethane, ethylene glycol dimethyl ether, water, dimethylsulfoxide, acetonitrile, dimethylacetamide, N-methylpyrrolidinone, tetrahydrofuran or mixtures thereof (preferred solvents include dimethylformamide and dimethoxyethane). The reaction may be carried out for example at room temperature or above (e.g. at a high temperature such as at about the reflux temperature of the solvent system). The reaction may be carried out at elevated temperature in a closed reactor or microwave.

Compound of formula (II) (e.g. in which there is an aromatic R$^4$ group attached to either end of the requisite double bond) may also be prepared by elimination of a compound of formula (VIIA),

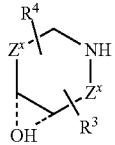  (VIIA)

wherein the dotted lines indicate that the —OH substituent is attached to either of the two positions on the nitrogen-containing heterocycloalkyl group, and Z$^x$, R$^3$ and R$^4$ are as hereinbefore defined (and preferably, there is an aromatic R$^4$ attached to the same carbon atom that the —OH group is attached to), for instance under standard conditions, e.g. under base elimination reaction conditions (e.g. using K$_2$CO$_3$ or the like as the base).

Compounds of formula (III) may be prepared by reaction of a compound of formula (VIII),

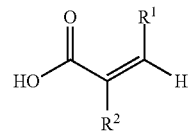  (VIII)

or a derivative thereof (e.g. an ester thereof such as —C(O)O-tert-butyl), wherein R$^1$ and R$^2$ are as hereinbefore defined, with a compound of formula (V) as hereinbefore defined, for example under reaction conditions such as those hereinbefore described above (preparation of compounds of formula (I), process step (ii)), e.g. DIPEA, Pd(OAc)$_2$, tri-O-tolylphosphine.

Compounds of formula (IV) may be prepared by reaction of a compound of formula (II) as hereinbefore defined, with a compound of formula (IX),

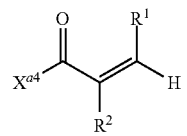  (IX)

wherein X$^{a4}$ represents a suitable leaving group, e.g. a sulfonate, chloro, iodo or bromo (especially chloro), under standard reaction conditions, such as an in presence of a suitable base (e.g. amine base such as triethylamine) and a suitable solvent (e.g. dichloromethane).

Compounds of formula V in which R$^x$ represents ring (i) and X$^x$ represents N may be prepared by reaction of a compound of formula (IXA),

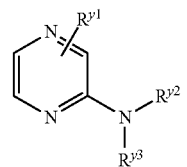  (IXA)

wherein R$^{y2}$ and R$^{y3}$ are as hereinbefore defined (e.g. both represent hydrogen), and R$^{y1}$ is as hereinbefore defined (e.g. there is one R$^{y1}$ substituent a to the —N(R$^{y2}$)(R$^{y3}$) group, for instance in which R$^{y1}$ represents —COO-ethyl), by halogenation, for instance by reaction in the presence of a suitable halide source, e.g. a source of bromide ions includes N-bromosuccinimide (NBS) and bromine, a source of iodide ions includes iodine, diiodoethane, diiodotetrachloroethane or, preferably, N-iodosuccinimide, and a source of chloride ions includes N-chlorosuccinimide, chlorine and iodine monochloride, for instance in the presence of a suitable solvent such as acetonitrile (e.g. NBS in the presence of a suitable solvent such as acetonitrile).

Compounds of formula (V) in which R$^x$ represents option (ii), i.e. the bicycle as hereinbefore defined, may be prepared by intramolecular cyclisation of a compound of formula (X),

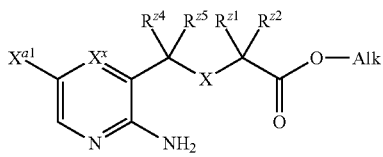

(X)

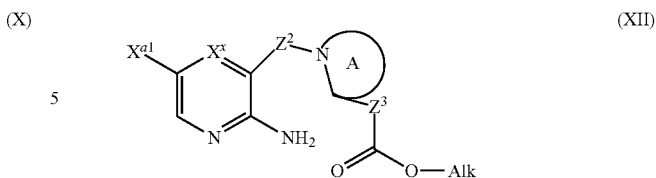

(XII)

wherein "Alk" represents a alkyl group (e.g. $C_{1-6}$ alkyl such as ethyl), X represents —O— or —N($R^{z3}$)—, and the remaining integers ($X^x$, $X^{a1}$, $R^{z1}$, $R^{z2}$, $R^{z3}$, $R^{z4}$ and $R^{z5}$ are as hereinbefore defined), for example under reaction conditions for instance in the presence of a suitable base (e.g. NaH) and suitable solvent (e.g. DMF).

Compounds of formula (V) in which $R^x$ represents option (ii), i.e. a bicycle, in which $X^1$ and $X^2$ represent a direct bond, may be prepared by reaction of a compound of formula (XI),

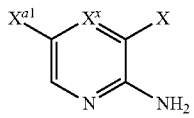

(XI)

wherein the integers are as hereinbefore defined, with a compound of formula (XII),

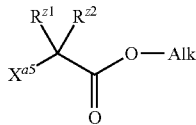

(XII)

wherein $X^{a5}$ represents a suitable leaving group such as chloro, iodo or bromo (especially bromo) and the other integers ($R^{z1}$, $R^{z2}$ and Alk) are as hereinbefore defined, for example under reaction conditions for instance in the presence of a suitable base (e.g. NaH) and suitable solvent (e.g. DMF). Corresponding compounds of formula (V) in which $X^{a1}$ is not present (i.e. represents hydrogen) may also be prepared accordingly (from corresponding compounds of formula (XI) in which $X^{a1}$ is not present, i.e. represents hydrogen).

Compounds of formula (V) in which $X^{a1}$ represents halo (e.g. bromo) may be prepared by reaction of a compound corresponding to a compound of formula (V) but in which $X^{a1}$ represents hydrogen, under appropriate reaction conditions, e.g. those that contain a source of halide (e.g. bromide) ions, for instance an electrophile that provides a source of iodide ions includes iodine, diiodoethane, diiodotetrachloroethane or, preferably, N-iodosuccinimide, a source of bromide ions includes N-bromosuccinimide and bromine, and a source of chloride ions includes N-chlorosuccinimide, chlorine and iodine monochloride, for instance in the presence of a suitable solvent.

Compounds of formula (V) in which $R^x$ is option (iii), i.e. a tricycle (e.g. in which $Z^3$ is a direct bond), may be prepared by intramolecular cyclisation of a compound of formula (XII), wherein the integers are as hereinbefore defined, for example under reaction conditions for instance in the presence of a suitable base (e.g. NaH) and suitable solvent (e.g. DMF).

Compounds of formula (VI) in which $X^{a2}$ represents —O—S(O)$_2$CF$_3$ may be prepared by reaction of by reaction of a compound of formula (XIII),

(XIII)

or a protected derivative thereof, for instance by reaction in the presence of a suitable base (e.g. an amine base, such as LDA, or the like), which may be prepared first and the compound of formula (XIII) may be added to it, in e.g. the presence of an inert solvent (e.g. a dry polar aprotic solvent, such as dry THF) at low temperature (e.g. at about −78° C.), followed by addition of N-phenyl-trifluoromethane sulfonimide or the like.

Compounds of formula (X) may be prepared by reaction of a compound of formula (XIV),

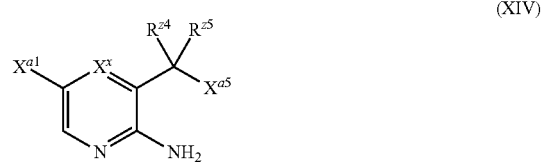

(XIV)

wherein $X^{a5}$ represents a suitable leaving group, such as bromo, chloro or iodo (especially bromo), and the other integers are as hereinbefore defined, with a compound of formula (XV),

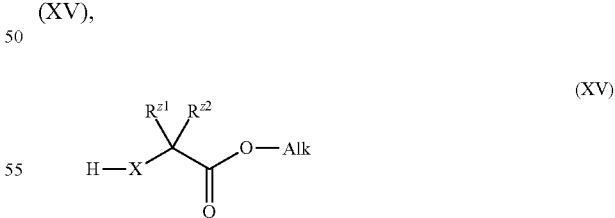

(XV)

wherein the integers are as hereinbefore defined, under conditions for instance the presence of a suitable base (e.g. an amine base, such as triethylamine) and a suitable solvent (e.g. DMF), which reaction may be performed at elevated temperature e.g. in a sealed tube and/or in a microwave.

Compounds of formula (XII) may be prepared for example under similar conditions to those described in respect of preparation of compounds of formula (X) (i.e. reaction of a compound of formula (XIV) with a compound of formula (XV)), but wherein the "—X—H" moiety (e g amino moiety) of the compound of formula (XV) corresponds to the —N(H)— moiety of the "A" ring for the preparation of compounds of formula (XII).

Compounds of formula (XIII) may be prepared by reduction of the double bond of the corresponding enone.

Certain intermediate compounds may be commercially available, may be known in the literature, or may be obtained either by analogy with the processes described herein, or by conventional synthetic procedures, in accordance with standard techniques, from available starting materials using appropriate reagents and reaction conditions.

Certain substituents on/in final compounds of the invention or relevant intermediates may be modified one or more times, after or during the processes described above by way of methods that are well known to those skilled in the art. Examples of such methods include substitutions, reductions, oxidations, alkylations, acylations, hydrolyses, esterifications, etherifications, halogenations or nitrations.

Compounds of the invention may be isolated from their reaction mixtures using conventional techniques (e.g. recrystallisations, where possible under standard conditions).

It will be appreciated by those skilled in the art that, in the processes described above and hereinafter, the functional groups of intermediate compounds may need to be protected by protecting groups.

The need for such protection will vary depending on the nature of the remote functionality and the conditions of the preparation methods (and the need can be readily determined by one skilled in the art). Suitable amino-protecting groups include acetyl, trifluoroacetyl, t-butoxycarbonyl (BOC), benzyloxycarbonyl (CBz), 9-fluorenyl-methyleneoxycarbonyl (Fmoc) and 2,4,4-trimethylpentan-2-yl (which may be deprotected by reaction in the presence of an acid, e.g. HCl in water/alcohol (e.g. MeOH)) or the like. The need for such protection is readily determined by one skilled in the art. For example the a —C(O)O-tert-butyl ester moiety may serve as a protecting group for a —C(O)OH moiety, and hence the former may be converted to the latter for instance by reaction in the presence of a mild acid (e.g. TFA, or the like).

The protection and deprotection of functional groups may take place before or after a reaction in the above-mentioned schemes.

Protecting groups may be removed in accordance with techniques that are well known to those skilled in the art and as described hereinafter. For example, protected compounds/intermediates described herein may be converted chemically to unprotected compounds using standard deprotection techniques.

The type of chemistry involved will dictate the need, and type, of protecting groups as well as the sequence for accomplishing the synthesis.

The use of protecting groups is fully described in "*Protective Groups in Organic Synthesis*", 3$^{rd}$ edition, T. W. Greene & P. G. M. Wutz, Wiley-Interscience (1999).

The compounds of formula (I) as prepared in the hereinabove described processes may be synthesized in the form of racemic mixtures of enantiomers which can be separated from one another following art-known resolution procedures. Those compounds of formula (I) that are obtained in racemic form may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds described herein are inhibitors of the FabI enzyme, as demonstrated in by the examples herein. In view of these FabI enzyme inhibiting properties the compounds described herein may therefore be useful for treating bacterial infections. For instance, these compounds are useful for the treatment of bacterial infections, such as, for example, infections of upper respiratory tract (e.g. otitis media, bacterial tracheitis, acute epiglottitis, thyroiditis), lower respiratory (e.g. empyema, lung abscess), cardiac (e.g. infective endocarditis), gastrointestinal (e.g. secretory diarrhoea, splenic abscess, retroperitoneal abscess), CNS (e.g. cerebral abscess), eye (e.g. blepharitis, conjunctivitis, keratitis, endophthalmitis, preseptal and orbital cellulitis, darcryocystitis), kidney and urinary tract (e.g. epididymitis, intrarenal and perinephric abscess, toxic shock syndrome), skin (e.g. impetigo, folliculitis, cutaneous abscesses, cellulitis, wound infection, bacterial myositis), and bone and joint (e.g. septic arthritis, osteomyelitis). Additionally, the compounds may be useful in combination with known antibiotics.

Therefore the present invention also relates to compounds of the invention for use as a medicine especially for use in treating bacterial infections, in particular bacterial infections caused by a bacterium that expresses a FabI enzyme. Subsequently the present compounds may be used for the manufacture of a medicine for treatment of bacterial infections, in particular bacterial infections caused by a bacterium that expresses a FabI enzyme.

Further, the present invention provides a method of treating bacterial infections which comprises administering to a subject in need thereof a FabI enzyme inhibiting compound of the invention.

A subject in need of treatment has a bacterial infection or has been exposed to an infectious bacterium, the symptoms of which may be alleviated by administering a therapeutically effective amount of the compounds of the present invention. For example, a subject in need of treatment can have an infection for which the compounds of the invention can be administered as a treatment. In another example, a subject in need of treatment can have an open wound or burn injury, for which the compounds of the invention can be administered as a prophylactic. Typically a subject will be treated for an existing bacterial infection.

A subject can have a bacterial infection caused by *Bacillus anthracis, Citrobacter* sp., *Escherichia coli, Francisella tularensis, Haemophilus influenza, Listeria mono-cytogenes, Moraxella catarrhalis, Mycobacterium tuberculosis, Neisseria meningitidis, Proteus mirabilis, Proteus vulgaris, Salmonella* sp., *Serratia* sp., *Shigella* sp., *Stenotrophomonas maltophilia, Staphylococcus aureus,* or *Staphylococcus epidermidis*. Preferably, the subject is treated (prophylactically or therapeutically) for a bacterial infection caused by a bacterium that expresses a FabI enzyme.

The term "treating" and "treatment', as used herein, refers to curative, palliative and prophylactic treatment, including reversing, alleviating, inhibiting the progress of, or preventing the disease, disorder or condition to which such term applies, or one or more symptoms of such disease, disorder or condition.

A "therapeutically effective amount" of a compound of the present invention is the quantity which, when administered to a subject in need of treatment, improves the prognosis of the subject, e.g. delays the onset of and/or reduces the severity of one or more of the subject's symptoms associated with a bacterial infection. The amount of the disclosed compound to be administered to a subject will depend on the particular disease, the mode of administration, and the characteristics of the subject, such as general health, other diseases, age, sex, genotype, body weight and tolerance to drugs. The skilled person will be able to determine appropriate dosages depending on these and other factors.

The compounds may be tested in one of several biological assays to determine the concentration of compound which is required to have a given pharmacological effect.

Additionally the present invention provides pharmaceutical compositions comprising at least one pharmaceutically acceptable carrier and a therapeutically effective amount of a compound of the invention.

In order to prepare the pharmaceutical compositions of this invention, an effective amount of the particular compound, in base or acid addition salt form, as the active ingredient is combined in intimate admixture with at least one pharmaceutically acceptable carrier, which carrier may take a wide variety of forms depending on the form of preparation desired for administration. These pharmaceutical compositions are desirably in unitary dosage form suitable, preferably, for oral administration, rectal administration, percutaneous administration or parenteral injection.

For example in preparing the compositions in oral dosage form, any of the usual liquid pharmaceutical carriers may be employed, such as for instance water, glycols, oils, alcohols and the like in the case of oral liquid preparations such as suspensions, syrups, elixirs and solutions; or solid pharmaceutical carriers such as starches, sugars, kaolin, lubricants, binders, disintegrating agents and the like in the case of powders, pills, capsules and tablets. Because of their easy administration, tablets and capsules represent the most advantageous oral dosage unit form, in which case solid pharmaceutical carriers are obviously employed. For parenteral injection compositions, the pharmaceutical carrier will mainly comprise sterile water, although other ingredients may be included in order to improve solubility of the active ingredient. Injectable solutions may be prepared for instance by using a pharmaceutical carrier comprising a saline solution, a glucose solution or a mixture of both. Injectable suspensions may also be prepared by using appropriate liquid carriers, suspending agents and the like. In compositions suitable for percutaneous administration, the pharmaceutical carrier may optionally comprise a penetration enhancing agent and/or a suitable wetting agent, optionally combined with minor proportions of suitable additives which do not cause a significant deleterious effect to the skin. Said additives may be selected in order to facilitate administration of the active ingredient to the skin and/or be helpful for preparing the desired compositions. These topical compositions may be administered in various ways, e.g., as a transdermal patch, a spot-on or an ointment. Addition salts of the compounds of formula (I), due to their increased water solubility over the corresponding base form, are obviously more suitable in the preparation of aqueous compositions.

It is especially advantageous to formulate the pharmaceutical compositions of the invention in dosage unit form for ease of administration and uniformity of dosage. "Dosage unit form" as used herein refers to physically discrete units suitable as unitary dosages, each unit containing a predetermined amount of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

For oral administration, the pharmaceutical compositions of the present invention may take the form of solid dose forms, for example, tablets (both swallowable and chewable forms), capsules or gelcaps, prepared by conventional means with pharmaceutically acceptable excipients and carriers such as binding agents (e.g. pregelatinised maize starch, polyvinylpyrrolidone, hydroxypropylmethylcellulose and the like), fillers (e.g. lactose, microcrystalline cellulose, calcium phosphate and the like), lubricants (e.g. magnesium stearate, talc, silica and the like), disintegrating agents (e.g. potato starch, sodium starch glycollate and the like), wetting agents (e.g. sodium laurylsulphate) and the like. Such tablets may also be coated by methods well known in the art.

Liquid preparations for oral administration may take the form of e.g. solutions, syrups or suspensions, or they may be formulated as a dry product for admixture with water and/or another suitable liquid carrier before use. Such liquid preparations may be prepared by conventional means, optionally with other pharmaceutically acceptable additives such as suspending agents (e.g. sorbitol syrup, methylcellulose, hydroxypropylmethylcellulose or hydrogenated edible fats), emulsifying agents (e.g. lecithin or acacia), non-aqueous carriers (e.g. almond oil, oily esters or ethyl alcohol), sweeteners, flavours, masking agents and preservatives (e.g. methyl or propyl p-hydroxybenzoates or sorbic acid).

Pharmaceutically acceptable sweeteners useful in the pharmaceutical compositions of the invention comprise preferably at least one intense sweetener such as aspartame, acesulfame potassium, sodium cyclamate, alitame, a dihydrochalcone sweetener, monellin, stevioside sucralose (4,1',6'-trichloro-4,1',6'-trideoxygalactosucrose) or, preferably, saccharin, sodium or calcium saccharin, and optionally at least one bulk sweetener such as sorbitol, mannitol, fructose, sucrose, maltose, isomalt, glucose, hydrogenated glucose syrup, xylitol, caramel or honey. Intense sweeteners are conveniently used in low concentrations. For example, in the case of sodium saccharin, the said concentration may range from about 0.04% to 0.1% (weight/volume) of the final formulation. The bulk sweetener can effectively be used in larger concentrations ranging from about 10% to about 35%, preferably from about 10% to 15% (weight/volume).

The pharmaceutically acceptable flavours which can mask the bitter tasting ingredients in the low-dosage formulations are preferably fruit flavours such as cherry, raspberry, black currant or strawberry flavour. A combination of two flavours may yield very good results. In the high-dosage formulations, stronger pharmaceutically acceptable flavours may be required such as Caramel Chocolate, Mint Cool, Fantasy and the like. Each flavour may be present in the final composition in a concentration ranging from about 0.05% to 1% (weight/volume). Combinations of said strong flavours are advantageously used. Preferably a flavour is used that does not undergo any change or loss of taste and/or color under the circumstances of the formulation.

The compounds of the invention may be formulated for parenteral administration by injection, conveniently intravenous, intra-muscular or subcutaneous injection, for example by bolus injection or continuous intravenous infusion. Formulations for injection may be presented in unit dosage form, e.g. in ampoules or multi-dose containers, including an added preservative. They may take such forms as suspensions, solutions or emulsions in oily or aqueous vehicles, and may contain formulating agents such as isotonizing, suspending, stabilizing and/or dispersing agents. Alternatively, the active ingredient may be present in powder form for mixing with a suitable vehicle, e.g. sterile pyrogen-free water, before use.

The compounds of the invention may also be formulated in rectal compositions such as suppositories or retention enemas, e.g. containing conventional suppository bases such as cocoa butter and/or other glycerides.

Those of skill in the treatment of antibacterial diseases linked to the inhibition of the FabI enzyme will easily determine the therapeutically effective amount of a compound of the invention from the test results presented hereinafter. In general it is contemplated that a therapeutically effective dose will be from about 0.001 mg/kg to about 50 mg/kg of body weight, more preferably from about 0.01 mg/kg to about 10 mg/kg of body weight of the patient to be treated. It may be appropriate to administer the therapeutically effective dose in the form of two or more sub-doses at appropriate intervals throughout the day. Said sub-doses may be formulated as unit dosage forms, for example each containing from about 0.1 mg to about 1000 mg, more particularly from about 1 to about 500 mg, of the active ingredient per unit dosage form.

The exact dosage and frequency of administration depends on the particular compound of the invention used, the particular condition being treated, the severity of the condition being treated, the age, weight and general physical condition of the particular patient as well as the other medication, the patient may be taking, as is well known to those skilled in the art. Furthermore, said "therapeutically effective amount" may be lowered or increased depending on the response of the treated patient and/or depending on the evaluation of the physician prescribing the compounds of the instant invention. The effective daily amount ranges mentioned hereinabove are therefore only guidelines.

Compounds of the invention/formula (I) may have the advantage that they may be more efficacious than, be less toxic than, be longer acting than, be more potent than, produce fewer side effects than, be more easily absorbed than, and/or have a better pharmacokinetic profile (e.g. higher oral bioavailability and/or lower clearance) than, and/or have other useful pharmacological, physical, or chemical properties over, compounds known in the prior art, whether for use in the above-stated indications or otherwise. The compounds may also exhibit such advantages in view of the requisite double bond in the $Z^x$-containing ring.

For instance, compounds of the invention/formula (I) may have the advantage that they have a good or an improved thermodynamic solubility (e.g. compared to compounds known in the prior art; and for instance as determined by a known method and/or a method described herein). Compounds of the invention/formula (I) may also have the advantage that they have a broad spectrum of activity against antibacterials (e.g. a broader spectrum of antibacterial activity compared to compounds known in the prior art; and for instance as determined by known tests and/or tests described herein). Compounds of the invention/formula (I) may also have the advantage that they have good or improved in vivo pharmacokinetics and oral bioavailabilty. They may also have the advantage that they have good or improved in vivo efficacy. For instance, the compounds of the invention may adaptable for intravenous formulation/dosing and hence may exhibit an improved in vivo efficacy when administered intravenously. The compounds may also exhibit such advantages in view of the requisite double bond in the $Z^x$-containing ring.

EXPERIMENTAL PART

Abbreviations

"DMF" is defined as N,N-dimethylformamide, "DCM" or "CH$_2$Cl$_2$" is defined as dichloromethane, "MeOH" is defined as methanol, "EtOH" is defined as ethanol, "MgSO$_4$" is defined as magnesium sulfate, and "THF" is defined as tetrahydrofuran, "AcOEt" or "EtOAc" is defined as ethyl acetate, "DIPEA" is defined as diisopropylethylamine, "EDCI" is defined as N'-(ethylcarbonimidoyl)-N,N-dimethyl-1,3-propanediamine monohydrochloride, "HOBT" is defined as 1-hydroxy-1H-benzotriazole, "DIPA" is defined as diisopropylamine, "K$_2$CO$_3$" is defined as potassium carbonate, "TFA" is defined as trifluoroacetic acid, "NH$_4$OH" is defined as ammonium hydroxide, "NaHCO$_3$" is defined as carbonic acid monosodium salt, "Et$_2$O" is defined as diethyl ether, "Na$_2$SO$_4$" is defined as sulfuric acid disodium salt, "CH$_3$CN" is defined as acetonitrile, "NaOH" is defined as sodium hydroxide, "n-BuLi" is defined as n-Butyllithium, "i-PrOH" is defined as isopropanol, "Pd(OAc)$_2$" is defined as palladium acetate, "DMA" is defined as dimethylacetamide, "Et$_3$N" is defined as triethylamine, SFC is defined as Supercritical Fluid Chromatography.

Stereochemical Representation

The compounds of formula (I) may have at least two asymmetric carbon atoms, for instance the fused rings that $R^x$ may represent. The fused ring systems may only exist as 'cis' forms, as the 'trans' forms may not be able to be prepared due to ring tension.

Synthesis of Examples

Synthesis of Final Compounds in which $R^x$ Represents Ring (i)

Synthesis of Final Compounds C

Example A

Preparation of Intermediate A

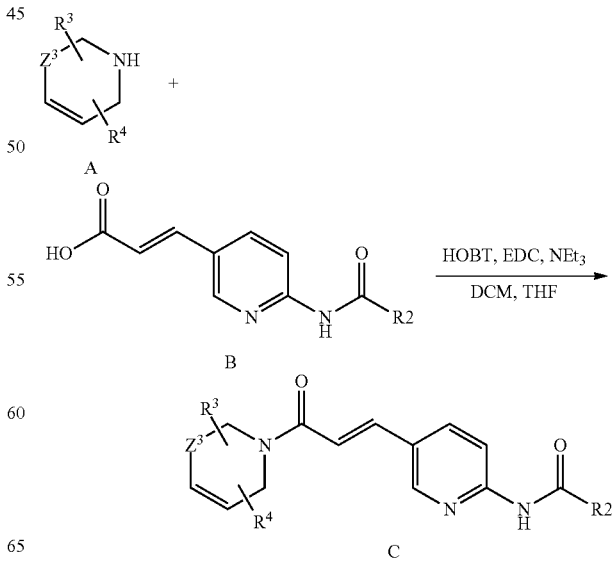

Preparation of CAS [324784-95-4]

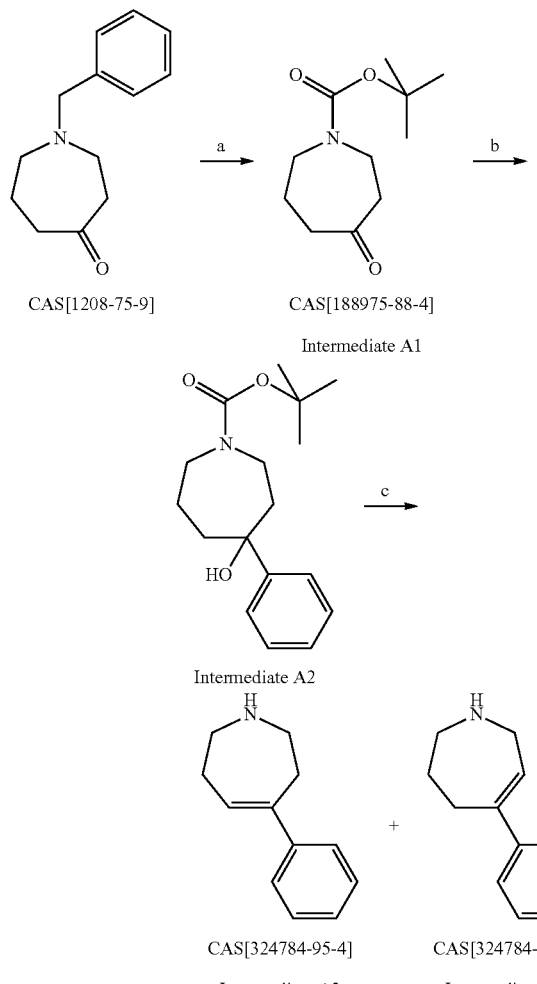

a) Pd((OH)$_2$)$_2$, NEt$_3$, EtOAc, RT, 3 bars; b) phenylmagnesium, THF, 5° C., 3 h; c) HCl, reflux, 30 minutes

Preparation of 4-Boc-hexahydroazepinone CAS [1889-75-88-4] (Intermediate A1)

A mixture of 1-Benzylhexahydro-4H-azepin-4-one CAS [1208-75-9] (34.0 g, 141.8 mmol), di-tert-butyl-dicarbonate (34.1 g, 156 mmol) and Pearlman's catalyst CAS[12135-22-7] (6.1 g, 42.5 mmol) in EtOAc (750 mL) and triethylamine (23.7 mL, 170.2 mmol) was hydrogenated at 3 bars and room temperature overnight in a Parr shaker.

The reaction mixture was filtered through a short pad of Celite®, the cake was washed with EtOAc, the filtrate was washed with water then brine, dried (MgSO$_4$) and evaporated to dryness to give 28.8 g (95%) of 4-Boc-hexahydroazepinone CAS [1889-75-88-4].

Preparation of Alcohol Intermediate A2

Under N$_2$ flow, phenylmagnesium chloride (1.8M, 91.5 mL, 165 mmol) was added dropwise to a solution of 4-Boc-hexahydroazepinone CAS [1889-75-88-4] (29.3 g, 137 mmol; Intermediate A1) in THF (300 mL) at 0° C. then the mixture was stirred 3 hours at 5° C. NH$_4$Cl 10% aq. and EtOAc were added, the organic layer was separated, washed with water and brine, dried (MgSO$_4$) and evaporated till dryness to give 37.8 g (95%) of alcohol intermediate.

Intermediate A3—1H-Azepine, 2,3,6,7-tetrahydro-4-phenyl CAS [324784-75-95-4]

A solution of alcohol intermediate (37.8 g, 129.7 mmol; Intermediate A2) in an aqueous solution of 35% HCl in water (190 mL) was stirred at room temperature for 1 hour. The reaction mixture was poured out into ice water and K$_2$CO$_3$ solid was added portionwise (until pH=9-10), then it was extracted twice with DCM. The organic layer were gathered, washed with water, dried (MgSO$_4$) and evaporated. The residue (15.2 g) was purified by column chromatography over silica gel (eluent: gradient from 1% NH$_4$OH, 93% DCM, 7% MeOH to 1% NH$_4$OH, 90% DCM, 10% MeOH). The pure fractions were collected and the solvent was evaporated. Yielding: 7.1 g, (32%) of 1H-Azepine, 2,3,6,7-tetrahydro-4-phenyl CAS [324784-75-95-4] (Intermediate A3a) and 2.3 g (10%) of 1H-Azepine, 2,3,4,7-tetrahydro-5-phenyl CAS [324784-75-93-2] (Intermediate A3b).

Further Intermediates of Example A intermediate (A4)

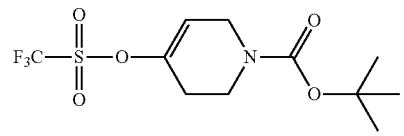

Reaction under N$_2$. BuLi (1.6 M in hexane) (8.28 ml, 13.2 mmol) was added dropwise at −20° C. to a solution of DIPA (1.86 ml, 13.2 mmol) in THF (20 ml) then the mixture was stirred at −20° C. for 20 minutes. A solution of 1-tert-butyloxycarbonyl-4-piperidone (2.2 g, 11.0 mmol) in THF (20 ml) was then added at −78° C. and the resulting mixture was stirred for 30 minutes at −78° C. A solution of 2-[N,N-bis(trifluoromethylsulfonyl)-amino]-5-chloropyridine (4.97 g, 12.1 mmol) in THF (10 ml) was added at −78° C. then the mixture was allowed to reach room temperature and was stirred overnight. The mixture was concentrated and the purification of the residue was carried out by flash chromatography over silica gel (silicagel 30 nm, 80 g, heptane/EtOAc 75/25. The desired product was collected and the solvent was evaporated, yielding 2.9 g of intermediate (A4).

intermediate (A5)

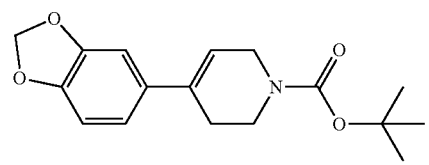

Reaction under N$_2$. A solution of intermediate (4) (0.3 g, 0.905 mmol) and 3,4-(methylenedioxy)phenyl boronic acid (0.18 g, 1.09 mmol) in K$_2$CO$_3$ (2 M, 0.905 ml) and ethylene glycol dimethyl ether (3 ml) was purged with N$_2$ for 10 minutes then tetrakis(triphenyl-phosphine)palladium(0)

(0.105 g, 0.0905 mmol) was added. The mixture was heated at 80° C. using a singlemode microwave (Biotage® initiator60) with a power output ranging from 0 to 400 W for 20 min, cooled to room temperature, water and EtOAc were added, the organic layer was separated, washed with water then brine, dried (MgSO$_4$) and evaporated till dryness. Purification of the residue was carried out by flash chromatography over silica gel (silicagel 10 g, 15-40 μm, heptane 100 to heptane/EtOAc 90/10) The pure fractions were collected and evaporated to dryness, yielding 0.17 g of intermediate (A5).

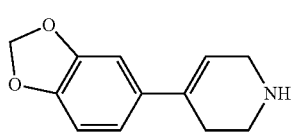

intermediate (A6)

A solution of intermediate (A5) (0.17 g, 0.56 mmol) in TFA (0.5 ml) and DCM (3 ml) was stirred at room temperature for 30 minutes, K$_2$CO$_3$ (10% aqueous solution) and DCM were added, the organic layer was separated, washed with water, dried (MgSO$_4$) and evaporated till dryness, yielding 0.11 g of intermediate (A6).

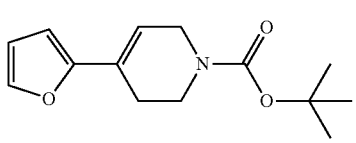

intermediate (A7)

Reaction under N$_2$. A solution of intermediate (A4) (0.3 g, 0.905 mmol) and furan-2-boronic acid (0.122 g, 1.09 mmol) in K$_2$CO$_3$ (0.905 ml) and ethylene glycol dimethyl ether (3 ml) was purged with N$_2$ for 10 minutes then tetrakis(triphenylphosphine)-palladium(0) (0.105 g, 0.0905 mmol) was added. The mixture was heated at 80° C. using a singlemode microwave (Biotage® initiator60) with a power output ranging from 0 to 400 W for 20 min, cooled to room temperature, water and EtOAc were added, the organic layer was separated, washed with water then brine, dried (MgSO$_4$) and evaporated till dryness. Purification of the residue was carried out by flash chromatography over silica gel §(10 g, 15-40 μm, heptane 100 to heptane/EtOAc 90/10).

The pure fractions were collected and evaporated to dryness, yielding 0.1 g of intermediate (A7).

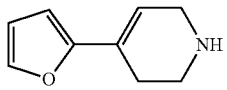

intermediate (A8)

A solution of intermediate (A7) (0.1 g, 0.401 mmol) in TFA (0.3 ml) and DCM (2 ml) was stirred at room temperature for 30 minutes, K$_2$CO$_3$ (10% aqueous solution) and DCM were added, the organic layer was separated, washed with water, dried (MgSO$_4$) and evaporated till dryness, yielding 0.046 g of intermediate (A8).

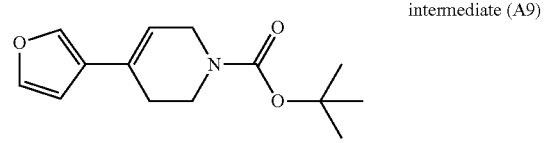 [SMILES: CC(C)(C)OC(=O)N1CC=C(c2ccoc2)CC1]

intermediate (A9)

Reaction under N$_2$. A solution of intermediate (A4) (0.28 g, 0.845 mmol) and furan-3-boronic acid (0.104 g, 0.93 mmol) in K$_2$CO$_3$ (2 M, 0.845 ml) and ethylene glycol dimethyl ether (3 ml) was purged with N$_2$ for 10 minutes then tetrakis(triphenyl-phosphine)palladium(0) (0.0977 g, 0.0845 mmol) was added. The mixture was heated at 80° C. using a singlemode microwave (Biotage® initiator60) with a power output ranging from 0 to 400 W for 20 min, cooled to room temperature, water and EtOAc were added, the organic layer was separated, washed with water then brine, dried (MgSO$_4$) and evaporated till dryness. Purification of the residue was carried out by flash chromatography over silica gel (10 g, 15-40 μm, heptane 100 to heptane/EtOAc 90/10). The pure fractions were collected and evaporated to dryness, yielding 0.146 g of intermediate (9).

intermediate (10)

A solution of intermediate (A9) (0.146 g, 0.586 mmol) in TFA (0.5 ml) and DCM (3 ml) was stirred at room temperature for 30 minutes, K$_2$CO$_3$ (10% aqueous solution) and DCM were added, the organic layer was separated, washed with water, dried (MgSO$_4$) and evaporated till dryness, yielding 0.085 g of intermediate (A10).

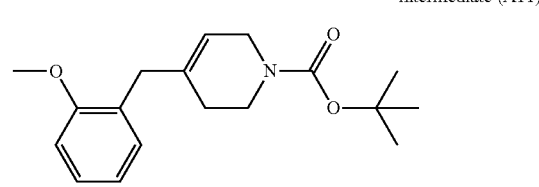

intermediate (A11)

Reaction under N$_2$. A solution of intermediate (A4) (0.1 g, 0.302 mmol) and 2-methoxybenzylzinc chloride (0.724 ml, 0.93 mmol) in THF (0.5 ml) was degassed by N$_2$ bubbling for 10 minutes then 1,1'-bis(diphenylphosphino)ferrocene-dichloro-palladium(II) (0.022 g, 0.03 mmol) was added. The mixture was heated at 80° C. using a singlemode microwave (Biotage® initiator60) with a power output ranging from 0 to 400 W for 20 min, cooled to room temperature, water and EtOAc were added, the organic layer was separated, washed with water then brine, dried (MgSO$_4$) and evaporated till dryness, yielding intermediate (A11).

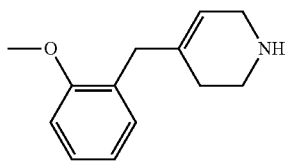

intermediate (A12)

A solution of intermediate (A11) (0.232 g, 0.765 mmol) in TFA (0.6 ml) and DCM (5 ml) was stirred at room temperature for 45 minutes, $K_2CO_3$ (10% aqueous solution) and DCM were added, the organic layer was separated, washed with water, dried ($MgSO_4$) and evaporated till dryness, yielding 0.145 g of intermediate (A12).

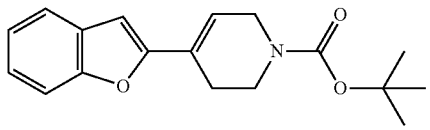

intermediate (A13)

Reaction under $N_2$. A solution of intermediate (A4) (0.3 g, 0.905 mmol) and benzo[b]furan-2-boronic acid (0.176 g, 1.09 mmol) in $K_2CO_3$ (2 M, 0.905 ml) and ethylene glycol dimethyl ether (3 ml) was purged with $N_2$ for 10 minutes then tetrakis(triphenyl-phosphine)palladium(0) (0.105 g, 0.0905 mmol) was added. The mixture was heated at 80° C. using a singlemode microwave (Biotage® initiator60) with a power output ranging from 0 to 400 W for 20 min, cooled to room temperature, water and EtOAc were added, the organic layer was separated, washed with water then brine, dried ($MgSO_4$) and evaporated till dryness. Purification of the residue was carried out by flash chromatography over silica gel (10 g, 15-40 μm, heptane 100 to heptane/EtOAc 90/10). The pure fractions were collected and evaporated to dryness, yielding 0.217 g of intermediate (A13).

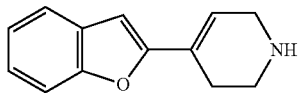

intermediate (A14)

A solution of intermediate (A13) (0.217 g, 0.725 mmol) in TFA (0.6 ml) and DCM (4 ml) was stirred at room temperature for 30 minutes, $K_2CO_3$ (10% aqueous solution) and DCM were added, the organic layer was separated, washed with water, dried ($MgSO_4$) and evaporated till dryness.

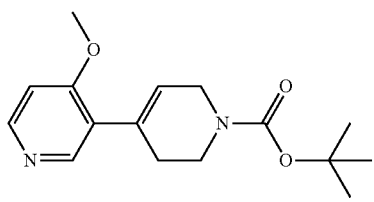

intermediate (A15)

Reaction under $N_2$. A solution of intermediate (A4) (0.752 g, 1.36 mmol) and 4-methoxy-3-pyridinylboronic acid (0.25 g, 1.64 mmol) in $K_2CO_3$ (2 M, 1.36 ml) and ethylene glycol dimethyl ether (8 ml) was degassed with $N_2$ for 10 minutes then tetrakis(triphenylphosphine)palladium(0) (0.157 g, 0.0136 mmol) was added. The mixture was heated at 80° C. using a singlemode microwave (Biotage® initiator60) with a power output ranging from 0 to 400 W for 30 min, cooled to room temperature, water and EtOAc were added, the organic layer was separated, washed with water then brine, dried ($MgSO_4$) and evaporated till dryness. Purification of the residue was carried out by flash chromatography over silica gel (30 g, 15-40 μm, gradient elution from $CH_2Cl_2$ to $CH_2Cl_2$/ MeOH/$NH_4OH$: 97/3/0.1) The pure fractions were collected and evaporated to dryness, yielding 0.19 g of intermediate (A15).

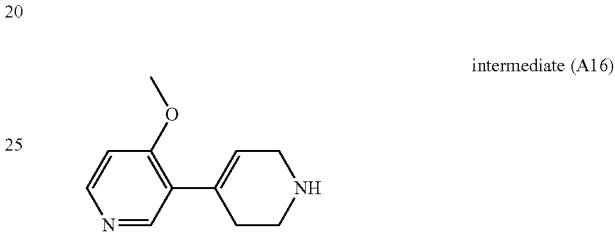

intermediate (A16)

A mixture of intermediate (A15) (0.2 g, 0.689 mmol) and TFA (0.218 ml) in DCM (2 ml) was stirred at room temperature for 30 minutes, $K_2CO_3$ (10% aqueous solution) and DCM were added, the organic layer was separated, washed with water, dried ($MgSO_4$) and evaporated till dryness, yielding 0.11 g of intermediate (A16).

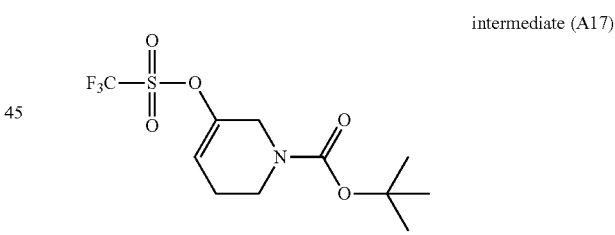

intermediate (A17)

Reaction under $N_2$. BuLi (1.6M in hexane) (3.76 ml, 6.02 mmol) was added dropwise at −20° C. to a solution of DIPA (0.846 ml, 6.02 mmol) in THF (10 ml) then the mixture was stirred at −20° C. for 20 minutes. A solution of 1-N-Boc-3-piperidone (1.0 g, 5.02 mmol) in THF (10 ml) was then added at −78° C. and the resulting mixture was stirred for 30 minutes at −78° C. A solution of 2-[N,N-bis(trifluoromethylsulfonyl)-amino]-5-chloropyridine (2.26 g, 5.52 mmol) in THF (5 ml) was added at −78° C. then the mixture was allowed to reach room temperature and was stirred overnight. The reaction mixture was evaporated till dryness. The obtained residue was purified by normal phase on (silicagel, 450 g, 20-45 μm, mobile phase (90% heptane, 10% AcOEt)). The desired fractions were collected and the solvent was evaporated, yielding 0.32 g of intermediate (A17).

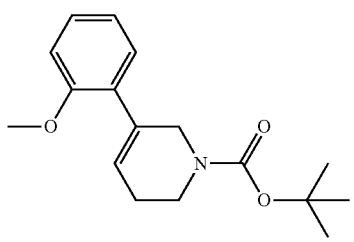

intermediate (A18)

Reaction under N₂. A solution of intermediate (A17) (0.32 g, 0.966 mmol) and 2-methoxyphenylboronic acid (0.176 g, 1.16 mmol) in K₂CO₃ (2 M, 0.97 ml) and ethylene glycol dimethyl ether (3 ml) was purged with N₂ for 10 minutes then tetrakis(triphenylphosphine)palladium(0) (0.112 g, 0.097 mmol) was added. The mixture was heated at 80° C. using a singlemode microwave (Biotage® initiator60) with a power output ranging from 0 to 400 W for 20 min, cooled to room temperature, water and EtOAc were added, the organic layer was separated, washed with water then brine, dried (MgSO₄) and evaporated till dryness. Purification of the residue was carried out by flash chromatography over silica gel (10 g, 15-40 μm, heptane 100 to heptane/EtOAc 80/20) The pure fractions were collected and evaporated to dryness, yielding 0.22 g of intermediate (A18).

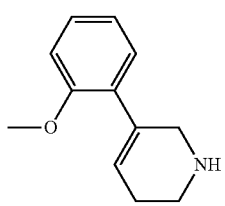

intermediate (A19)

A mixture of intermediate (18) (0.2 g, 0.76 mmol) and TFA (0.6 ml) in DCM (4 ml) was stirred at room temperature for 30 minutes, K₂CO₃ (10% aqueous solution) and DCM were added, the organic layer was separated, washed with water, dried (MgSO₄) and evaporated till dryness, yielding 0.13 g of intermediate (A19).

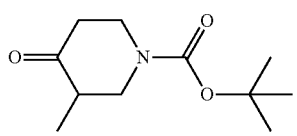

intermediate (A20)

A mixture of 1-benzyl-3-methyl-4-piperidone (2.0 g, 9.84 mmol), di-tert-butyl dicarbonate (2.36 g, 10.8 mmol) and Pearlman's catalyst (palladium(II)hydroxide) (0.35 g, 2.46 mmol) in EtOAc (50 ml) was hydrogenated (3 bar, room temperature) overnight in a Parr shaker. The reaction mixture was filtered through a short pad of celite, the cake was washed with EtOAc, the filtrate was washed with water then brine, dried (MgSO₄) and evaporated till dryness, yielding 2.2 g of intermediate (A20).

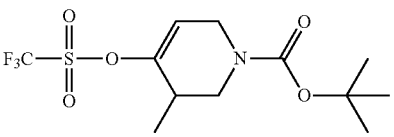

intermediate (A21)

Reaction under N₂. BuLi (1.6M in hexane) (3.52 ml, 5.63 mmol) was added dropwise at −20° C. to a solution of DIPA (0.791 ml, 5.63 mmol) in THF (8 ml) then the mixture was stirred at −20° C. for 20 minutes. A solution of intermediate (A20) (1.0 g, 4.70 mmol) in THF (10 ml) was then added at −78° C. and the resulting mixture was stirred for 30 minutes at −78° C. A solution of N-phenyltrifluoromethanesulfonimide (1.92 g, 5.16 mmol) in THF (6 ml) was added at −78° C. then the mixture was allowed to reach room temperature and was stirred overnight. The mixture was concentrated and purified by normal phase on (silicagel, 20-45 μm, 450 g, mobile phase (80% heptane, 20% AcOEt)). The desired fractions were collected and the solvent was evaporated, yielding 1.7 g of intermediate (A21).

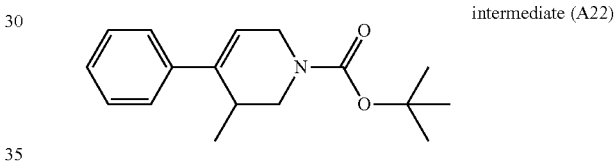

intermediate (A22)

Reaction under N₂. A solution of intermediate (A21) (1.0 g, 1.45 mmol) and phenylboronic acid (0.194 g, 1.59 mmol) in K₂CO₃ (2M, 1.45 ml) and ethylene glycol dimethyl ether (10 ml) was purged with N₂ for 10 minutes then tetrakis(triphenyl-phosphine)palladium(0) (0.167 g, 0.145 mmol) was added. The mixture was heated at 80° C. using a singlemode microwave (Biotage® initiator60) with a power output ranging from 0 to 400 W for 20 min, cooled to room temperature, water and EtOAc were added, the organic layer was separated, washed with water then brine, dried (MgSO₄) and evaporated till dryness, yielding 0.23 g of intermediate (A22).

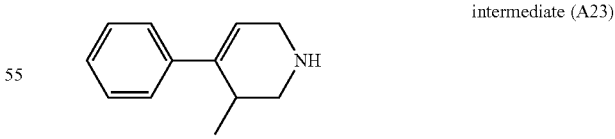

intermediate (A23)

A mixture of intermediate (A22) (0.23 g, 0.841 mmol) and TFA (0.8 ml) in DCM (5 ml) was stirred at room temperature for 30 minutes then the reaction mixture was poured out into K₂CO₃ (10% aqueous solution) and extracted with DCM. The organic layer was separated, washed with water, dried (MgSO₄) and evaporated till dryness, yielding 0.143 g of intermediate (A23).

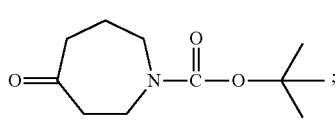

intermediate (A24)

A mixture of N-benzylhexahydroazepin-4-one hydrochloride (25.0 g, 104.3 mmol), di-tert-butyl dicarbonate (25.0 g, 114.7 mmol) and Pearlman's catalyst (4.46 g, 31.3 mmol) in EtOAc (550 ml) and triethylamine (17.4 ml, 125.13 mmol) was hydrogenated (3 bar, room temperature) overnight in a Parr shaker. The reaction mixture was filtered through a short pad of Celite®, the cake was washed with EtOAc, the filtrate was washed with water then brine, dried (MgSO$_4$) and evaporated till dryness to give 23.4 g of intermediate (A24).

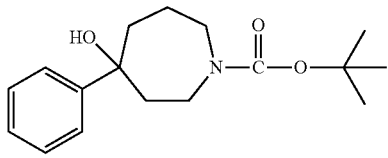

intermediate (A25)

Reaction under N$_2$. Phenylmagnesium chloride (1.8M, 93.8 ml, 169 mmol) was added dropwise to a solution of intermediate (A24) (30 g, 141 mmol) in THF (300 ml) at 0° C. then the mixture was stirred 3 hours at 5° C. NH$_4$Cl 10% aqueous and EtOAc were added, the organic layer was separated, washed with water and brine, dried (MgSO$_4$) and evaporated till dryness to give 39.2 g of intermediate (A25).

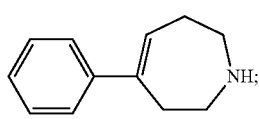

intermediate (A26)

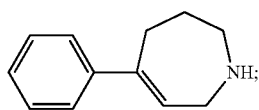

intermediate (A27)

A solution of intermediate (A25) (38.85 g, 133.3 mmol) in HCl (35% in water, 200 ml) was stirred at room temperature for 1 hour. The reaction mixture was poured out into crushed ice and K$_2$CO$_3$ solid was added portionwise (until pH=9-10), then it was extracted twice with DCM. The organic layer were gathered, washed with water, dried (MgSO$_4$) and evaporated until dryness. The residue was purified by preparative liquid chromatography on (silicagel 20-45 μm, 1000 g, mobile phase (1% NH$_4$OH, 93% DCM, 7% MeOH)). The pure fractions were collected and the solvent was evaporated to yield intermediate (A26) and intermediate (A27).

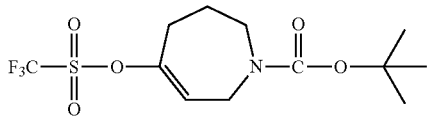

intermediate (A28)

Reaction under N$_2$. n-Butyllithium 1.6M in hexane (6.35 ml, 9.31 mmol) was added dropwise at −20° C. to a solution of diisopropylamine (1.43 ml, 10.2 mmol) in THF (15 ml) then the mixture was stirred at −20° C. for 20 minutes. A solution of intermediate (A24) (1.9 g, 8.46 mmol) in THF (20 ml) was then added at −78° C. and the resulting mixture was stirred for 30 minutes at −78° C. A solution of 2-[N,N-bis(trifluoromethyl-sulfonyl)-amino]-5-chloropyridine (3.8 g, 9.31 mmol) in THF (10 ml) was added at −78° C. then the mixture was allowed to reach room temperature and was stirred overnight and concentrated. The residue was purified by normal phase column chromatography (silicagel 20-45 μm, 450 g, mobile phase (80% heptane, 20% ethyl acetate)). The pure fractions were collected and the solvent was evaporated to give 1.34 g of intermediate (A28).

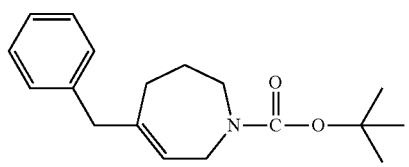

intermediate (A29)

Reaction under N$_2$. A solution of intermediate (A28) (0.24 g, 0.695 mmol) in THF (2 ml) and benzylzinc bromide in THF (0.5 M, 3.34 ml, 1.67 mmol) was degassed with nitrogen bubbling for 10 minutes then 1,1'-bis(diphenylphosphino)ferrocenedichloro-palladium(II) (0.102 g, 0.139 mmol) was added. The mixture was heated at 80° C. using a singlemode microwave (Biotage® initiator60) with a power output ranging from 0 to 400 W for 20 min, cooled to room temperature, water and ethyl acetate were added, the mixture was filtered through a short pad of Celite®, the organic layer was separated, washed with water then brine, dried (MgSO$_4$) and evaporated till dryness. The residue was purified by flash chromatography over a short silica gel cartridge with a mixture of heptane to heptane/EtOAc 90/10). The pure fractions were collected and evaporated to dryness to yield 0.11 g of intermediate (A29).

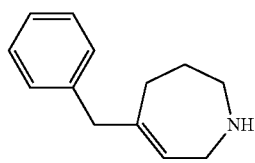

intermediate (A30)

A mixture of intermediate (A29) (0.11 g, 0.383 mmol) and TFA (0.3 ml) in DCM (2 ml) was stirred at room temperature for 30 minutes then the reaction mixture was poured out into K$_2$CO$_3$ (10% aqueous solution) and extracted with DCM. The organic layer was separated, washed with water, dried (MgSO$_4$) and evaporated till dryness to yield 0.058 g of intermediate (A30).

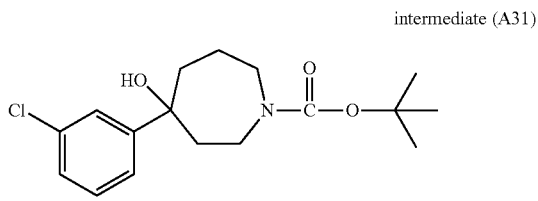 [SMILES: CC(C)(C)OC(=O)N1CCCC(O)(c2cccc(Cl)c2)CC1]

intermediate (A31)

Reaction under N$_2$. 3-Chlorophenylmagnesium bromide (0.5M, 100 ml, 50.0 mmol) was added dropwise to a solution of intermediate (4) (8.9 g, 41.7 mmol) in THF (90 ml) at 0° C. then the mixture was stirred 3 hours at 5° C. NH$_4$Cl (10% aqueous solution) and EtOAc were added, the organic layer was separated, washed with water and brine, dried (MgSO$_4$) and evaporated till dryness. The residue was carried out by flash chromatography over a silica gel cartridge [15-40 μm, heptane/EtOAc 80/20 to heptane/EtOAc 60/40]. The pure fractions were collected and evaporated to dryness to yield 4.4 g of intermediate (A31).

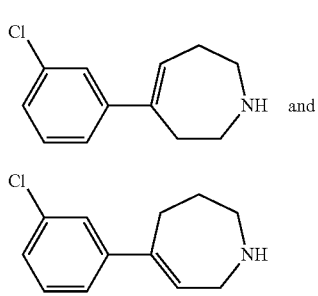

intermediate (A32)

intermediate (A33)

A solution of intermediate (A31) (4.4 g, 13.5 mmol) in HCl in water (35%, 22 ml) was stirred at room temperature for 1 hour. The reaction mixture was poured out into crushed ice and K$_2$CO$_3$ solid was added portionwise (until pH=9-10), then it was extracted twice with DCM. The organic layer were gathered, washed with water, dried (MgSO$_4$) and evaporated until dryness. The aqueous layer was evaporated, taken up in DCM and filtered. It was gathered with the first extract and evaporated till dryness. The residue was carried out by flash chromatography over silica gel (15-40 μm, 90 g, from DCM to DCM/MeOH/NH$_4$OH: 90/10/0.5). The pure fractions were collected and evaporated to dryness. The residue was purified by preparative liquid chromatography on [silicagel 15-40 μm, 300 g, mobile phase (0.5% NH$_4$OH, 90% DCM, 10% MeOH)]. The pure fractions were collected and the solvent was evaporated to give 1 g of intermediate (12) and 0.4 g of intermediate (A33).

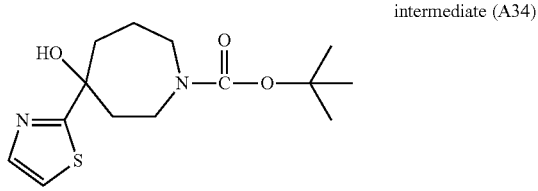 [SMILES: CC(C)(C)OC(=O)N1CCCC(O)(c2nccs2)CC1]

intermediate (A34)

Reaction under N$_2$. n-Butyllithium in hexane (1.6 M, 3.52 ml, 5.63 mmol) was added dropwise at −78° C. to a solution of thiazole (0.366 ml, 5.16 mmol) in diethyl ether (5 ml) and the mixture was stirred for 30 minutes. A solution of intermediate (A24) (1.0 g, 4.69 mmol) in diethyl ether (5 ml) was added then the mixture stirred and allowed to reach room temperature for 2 hours. Water and EtOAc were added, the organic layer was separated, washed with water then brine, dried (MgSO$_4$) and evaporated till dryness. The residue was purified by preparative liquid chromatography (silicagel 15-40 μm, 25 g, mobile phase (70% heptane, 30% EtOAc) to give 1.05 g of intermediate (A34).

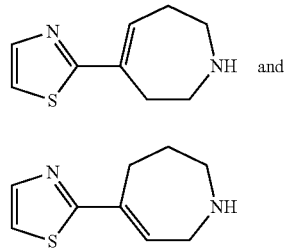

intermediate (A35)

and intermediate (A36)

Intermediate (A34) (710 mg, 2.38 mmol) and HCl concentrated (2 mL) in acetonitrile (6 mL) were stirred at reflux 2 days. The solvent was evaporated. Water and DCM were added. K$_2$CO$_3$ powder was added to basify the aqueous layer and the organic layer was removed. The aqueous layer was extracted again with DCM after saturation of the aqueous layer with K$_2$CO$_3$. The combined organic layers were concentrated and the residue was purified and separated by column chromatography over silica gel (15-40 μm, 25 g), yielding 137 mg of intermediate (A35) and 65 mg of intermediate (A36).

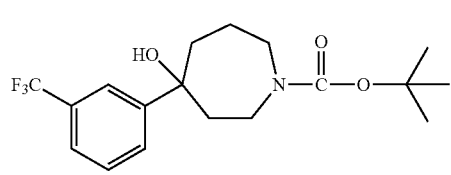

intermediate (A37)

Reaction under N$_2$. 3-(Trifluoromethyl)phenylmagnesium bromide (0.5M in Et$_2$O, 5.6 mmol, 10 ml) was added dropwise to a solution of intermediate (4) (1 g, 4.69 mmol) in THF (15 ml) at 0° C. then the mixture was stirred 3 hours at 5° C. NH$_4$Cl (10% aqueous solution) and EtOAc were added, the organic layer was separated, washed with water and brine, dried (MgSO$_4$) and evaporated till dryness. Purification was carried out by flash chromatography over silica gel (40 g, heptane/EtOAc from 85/15). Pure fractions were collected and concentrated, yielding 520 mg of intermediate (A37).

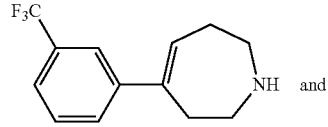

intermediate (A38)

and intermediate (A39)

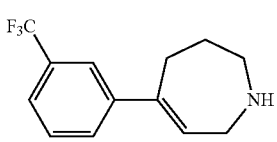

A solution of intermediate (A37) (400 mg, 1.13 mmol) in HCl (37% in water, 15 ml) was stirred for 30 minutes at reflux then cooled to room temperature. The reaction mixture was poured out into crushed ice and $K_2CO_3$ solid was added portionwise (until pH=9-10), then it was extracted twice with DCM. The organic layer were gathered, washed with water, dried ($MgSO_4$) and evaporated until dryness. The residue was purified by preparative liquid chromatography on (silicagel 5 μm, 150×30.0 mm, mobile phase (gradient from 0.2% $NH_4OH$, 98% DCM, 2% MeOH to 1.2% $NH_4OH$, 88% DCM, 12% MeOH)). The pure fractions were collected and the solvent was evaporated to yield 140 mg of intermediate (A38) and 42 mg of intermediate (A39).

intermediate (A40)

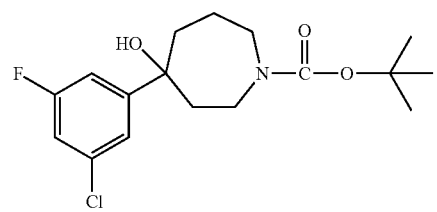

Reaction under $N_2$. 3-Chloro-5-fluorophenylmagnesium bromide (5M in THF) (14.1 mL, 7 mmol) was added dropwise to a solution of intermediate (A24) (1 g, 4.7 mmol) in THF (20 ml) at 0° C. then the mixture was stirred 3 hours at 5° C. $NH_4Cl$ (10% aqueous solution) and EtOAc were added, the organic layer was separated, washed with water and brine, dried ($MgSO_4$) and evaporated till dryness. Purification was carried out by flash chromatography over silica gel (40 g, heptane/EtOAc from 85/15). Pure fractions were collected and concentrated to yield 900 mg of intermediate (A40).

intermediate (A41)

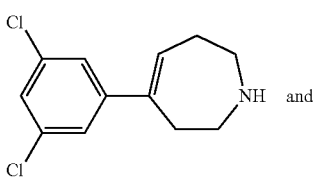

intermediate (A42)

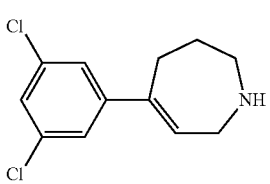

A solution of intermediate (A40) (900 mg, 2.5 mmol) in HCl (37% in water, 30 ml) was stirred for 30 minutes at reflux then cooled to room temperature. The reaction mixture was poured out into crushed ice and $K_2CO_3$ solid was added portionwise (until pH=9-10), then it was extracted twice with DCM. The organic layer were gathered, washed with water, dried ($MgSO_4$) and evaporated until dryness. The residue was purified by preparative liquid chromatography on (silicagel 5 μm 150×30.0 mm) mobile phase (gradient from 0.2% $NH_4OH$, 98% DCM, 2% MeOH to 1% $NH_4OH$, 90% DCM, 10% MeOH). Two fractions were collected and the solvent was evaporated to yield 290 mg of intermediate (A41) and 80 mg of intermediate (A42).

intermediate (A43)

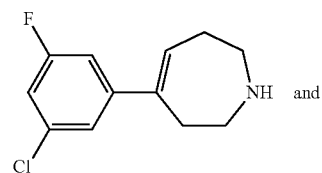

Reaction under $N_2$. 3-Chloro-5fluorophenylmagnesiumbromide (0.5 M in THF, 18.7 mL, 9.37 mmol) was added dropwise to a solution of intermediate (A4) (1 g, 4.7 mmol) in THF (20 ml) at 0° C. then the mixture was stirred 3 hours at 5° C. $NH_4Cl$ (10% aqueous solution) and EtOAc were added. The organic layer was separated, washed with water and brine, dried ($MgSO_4$) and evaporated till dryness. Purification was carried out by flash chromatography over silica gel (40 g, heptane/EtOAc from 85/15). The pure fractions were collected and the solvent was evaporated to yield 650 mg of intermediate (A43).

intermediate (A44)

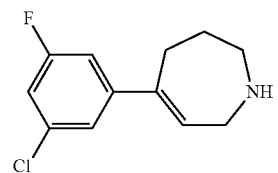

intermediate (A45)

A solution of intermediate (A43) (800 mg, 2.33 mmol) in HCl (37% in water, 25 ml) was stirred for 30 minutes at reflux and then cooled to room temperature. The reaction mixture was poured out into crushed ice and $K_2CO_3$ solid was added portionwise (until pH=9–10), then it was extracted twice with DCM. The organic layers were gathered, washed with water, dried ($MgSO_4$) and evaporated until dryness. The crude product was purified by preparative liquid chromatography on (silicagel 5 μm 150×30.0 mm, mobile phase (gradient from 0.2% $NH_4OH$, 98% DCM, 2% MeOH to 1% $NH_4OH$, 90% DCM, 10% MeOH)). Two fractions were collected and the solvent was evaporated to yield 325 mg of intermediate (A44) and 90 mg of intermediate (A45).

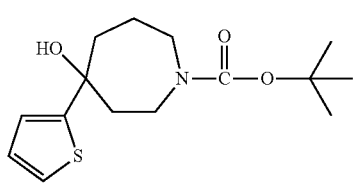

intermediate (A46)

Reaction under N$_2$. n-Butyllithium (1.6 M in hexane, 10.55 ml, 16.88 mmol) was added dropwise at −78° C. to a solution of 2-bromothiophene (1.5 ml, 15.47 mmol) in diethyl ether (7.5 ml) then the mixture was stirred for 30 minutes. A solution of intermediate (A24) (3 g, 14.07 mmol) in diethyl ether (7.5 ml) was added. The mixture was stirred and allowed to reach room temperature for 2 hours. Water and EtOAc were added, the organic layer was separated, washed with water then brine, dried (MgSO$_4$) and evaporated till dryness. The residue was purified by preparative liquid chromatography on (silicagel 15-40 µm, 90 g, mobile phase (80% heptane, 20% EtOAc)). The pure fractions were collected and the solvent was evaporated to yield 2.65 g of intermediate (A46).

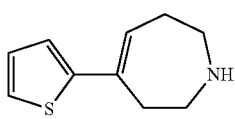

intermediate (A47)

Intermediate (A46) (6.3 g, 21.18 mmol) and HCl concentrated (15 mL) in acetic acid (45 mL) were stirred at reflux for 45 minutes. Solvents were evaporated. Water and DCM were added. K$_2$CO$_3$ powder was added to basify and the organic phase was removed. The aqueous phase was saturated with K$_2$CO$_3$ powder and extracted with a solvent mixture of DCM with methanol (95/5). Both organic phases were combined, evaporated to dryness and the residue was purified by column chromatography over silica gel (15-40 µm, 100 g) with a solvent mixture of DCM/methanol/NH$_4$OH (92/7/1), yielding intermediate (A47).

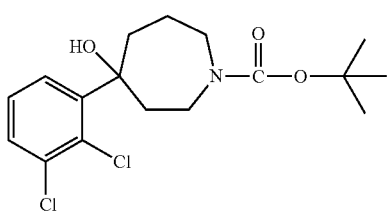

intermediate (A49)

Reaction under N$_2$. Bromo(2,3-dichlorophenyl)-magnesium (0.75M in Et$_2$O, 15 mmol, 20 ml) was added dropwise to a solution of intermediate (A24) (2.1 g, 10 mmol) in THF (20 ml) at 0° C. then the mixture was stirred for 3 hours at 5° C. NH$_4$Cl (10% aqueous solution) and EtOAc were added, the organic layer was separated, washed with water and brine, dried (MgSO$_4$) and evaporated till dryness. The crude product was crystallized from heptane/EtOAc 80/20 and air dried, yielding 700 mg of intermediate (A49).

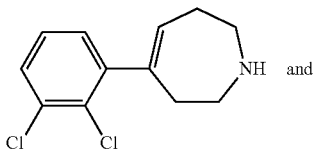

intermediate (A50)

and

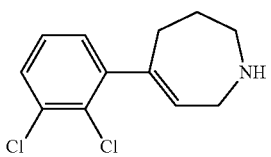

intermediate (A51)

A solution of intermediate (A49) (700 mg, 1.694 mmol) in HCl (37% in water, 20 ml) was stirred for 30 minutes at reflux then cooled to room temperature. The reaction mixture was poured out into crushed ice and K$_2$CO$_3$ solid was added portionwise (until pH=9–10), then it was extracted twice with DCM. The organic layer were gathered, washed with water, dried (MgSO$_4$) and evaporated until dryness. The crude product was purified by preparative liquid chromatography on (silicagel 5 µm 150×30.0 mm, mobile phase (gradient from 0.2% NH$_4$OH, 98% DCM, 2% MeOH to 1.1% NH$_4$OH, 89% DCM, 11% MeOH)). The pure fractions were collected and the solvent was evaporated, yielding intermediate (A50) and a second fraction. The second fraction was purified by preparative liquid chromatography on (silicagel 5 µm 150×30.0 mm, mobile phase (gradient from 0.2% NH$_4$OH, 98% DCM, 2% MeOH to 1.1% NH$_4$OH, 89% DCM, 11% MeOH)). The pure fractions were collected and the solvent was evaporated, yielding intermediate (A51).

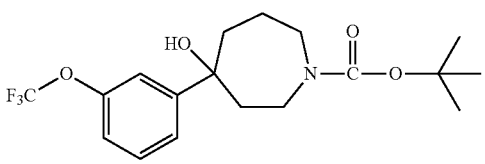

intermediate (A52)

Reaction under N$_2$. Bromo[3-(trifluoromethoxy)phenyl]-magnesium (0.5M in Et$_2$O, 4.15 mmol) was added dropwise to a solution of intermediate (A24) (0.6 g, 2.77 mmol) in THF (10 ml) at 0° C. then the mixture was stirred 3 hours at 5° C. NH$_4$Cl (10% aqueous solution) and EtOAc were added, the organic layer was separated, washed with water and brine, dried (MgSO$_4$) and evaporated till dryness. Purification was carried out by flash chromatography over silica gel (40 g, heptane/EtOAc from 80/20). Pure fractions were collected and concentrated, yielding 250 mg of intermediate (A52).

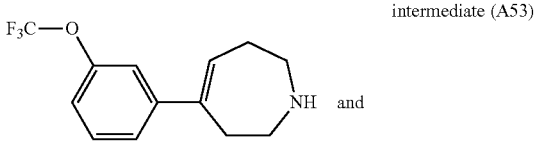

intermediate (A53)

and

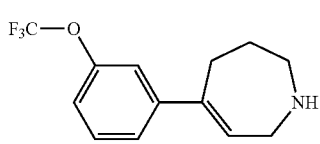

intermediate (A54)

A solution of intermediate (A52) (240 mg, 0.639 mmol) in HCl (37% in water, 10 ml) was stirred for 30 minutes at reflux then cooled to room temperature. The reaction mixture was poured out into crushed ice and K₂CO₃ solid was added portionwise (until pH=9–10), then it was extracted twice with DCM. The organic layer were gathered, washed with water, dried (MgSO₄) and evaporated until dryness. The residue (136 mg) was purified by column chromatography over silica gel (15-40 μm, 25 g) with a solvent mixture of DCM/methanol/acetonitrile (92/7/1) to give 86 mg of intermediate (A53) and 33 mg of intermediate (A54).

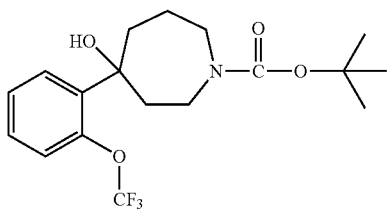

intermediate (A55)

Reaction under N₂. Bromo[2-(trifluoromethoxy)phenyl]-magnesium (1M in Et₂O, 13.7 mmol) was added dropwise to a solution of intermediate (A24) (1.95 g, 9.1 mmol) in THF (20 ml) at 0° C. then the mixture was stirred 3 hours at 5° C. NH₄Cl (10% aqueous solution) and EtOAc were added, the organic layer was separated, washed with water and brine, dried (MgSO₄) and evaporated till dryness. Purification was carried out by flash chromatography over silica gel (40 g, heptane/EtOAc from 80/20). Pure fractions were collected and concentrated, yielding 550 mg of intermediate (A55).

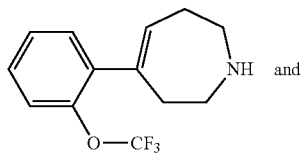

intermediate (A56)

and

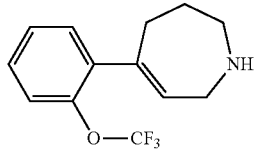

intermediate (A57)

Intermediate (A55) (450 mg, 1.2 mmol) and HCl concentrated (1.5 mL) in acetic acid (4.5 mL) were stirred at reflux overnight. Solvents were evaporated. Water and DCM were added. K₂CO₃ powder was added to basify. The organic layer was removed and evaporated and the crude product (350 mg) was purified by preparative liquid chromatography on (sili-cagel 5 μm 150×30.0 mm, mobile phase (gradient from 0.2% NH₄OH, 98% DCM, 2% MeOH to 1.2% NH₄OH, 88% DCM, 12% MeOH)). Two fractions were collected and the solvent was evaporated, yielding 140 mg of intermediate (A56) and 63 mg of intermediate (A57).

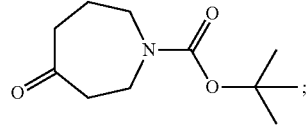

intermediate (A58)

Hexahydro-1-(phenylmethyl)-4H-azepin-4-one, hydrochloride (56 g, 233 mmol) was added to Na₂CO₃ (saturated, aqueous solution, 1000 mL) and EtOAc (1000 mL). The mixture was stirred for 30 minutes. The organic layer was separated, the water layer was extracted with EtOAc (1000 mL). The combined organic layers were dried over Na₂SO₄, filtrated and the filtrate's solvent was evaporated. The residue and tert-butyl dicarbonate (66 g, 300 mmol) in EtOAc (800 mL) was hydrogenated at room temperature (0.4 MPa) with Pd(OH)₂ (15 g) as a catalyst. After uptake of hydrogen (1 equivalent), the catalyst was filtered off and the filtrate was evaporated. The residue was purified by column chromatography over silica gel (eluent: petroleum ether/EtOAc 3/1). The product fractions were collected and the solvent was evaporated, yielding 49 g of intermediate (A58).

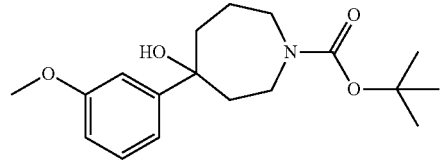

intermediate (A59)

Mg (0.34 g, 14 mmol), a few drops of a solution of 1-bromo-3-methoxy-benzene (1.1 ml, 9.28 mmol) in THF (5 mL) and iodine (0.01 g) in THF (30 mL) was introduced in to an anhydrous three-necked flask equipped with a nitrogen supply, a funnel, and a reflux condenser. The mixture was gently heated until the reaction started, then the rest solution of 1-bromo-3-methoxy-benzene was added dropwise at a rate which maintained reflux. Agitation was continued until the iodine completely disappeared (about 1 hour). Then the mixture was cooled to 0° C. The solution of intermediate (A58) (2.0 g, 9.38 mmol) in THF (10 ml) was added to the mixture. The reaction mixture was stirred at ice-bath, then warmed to room temperature. The reaction mixture was quenched with saturated NH₄Cl (20 mL) and stirred at room temperature overnight. The organic layer was separated, the water layer was extracted with EtOAc (3×50 mL). The combined organic layers were dried over Na₂SO₄, filtrated and the filtrate's solvent was evaporated. The residue was purified by column chromatography over silica gel (eluent: petroleum ether/EtOAc 10/1). The product fraction were collected and the solvent was evaporated, yielding 2.3 g of intermediate (A59).

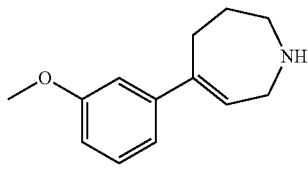
intermediate (A60)

To a solution of intermediate (A59) (2.0 g, 6.5 mmol) in DCM (30 mL) was added drop wise TFA (20 mL) at 0° C. After the addition, the mixture was stirred for 2 hour at room temperature. The reaction mixture was concentrated (<35° C.). The mixture was partitioned with brine (20 mL), $Na_2CO_3$ (5 g) and EtOAc (20 mL), the water layer was extracted with EtOAc (3×20 mL). The combined organic layer was dried over $Na_2SO_4$, filtrated and the solvent was evaporated. The residue was purified by column chromatography over silica gel (eluent: DCM/MeOH 30/1). The pure fractions were collected and the solvent was evaporated, yielding 0.2 g of intermediate (A60).

The following compounds were made using the same procedure as the example above whereby 1-methoxy-3-methyl-benzene was replaced by 1-bromo-2-methyl-benzene, 2-bromo-4-fluoro-1-methoxy-benzene, 1-bromo-4-chloro-benzene, 1-bromo-2-methoxy-benzene, 2-bromo-4-fluoro-1-methyl-benzene, 1-bromo-4-methoxy-benzene, 1-bromo-3-methoxy-benzene, 1-bromo-3-chloro-benzene or 1-bromo-2-chloro-benzene respectively.

intermediate (61)

intermediate (62)

intermediate (63)

intermediate (64)

intermediate (65)
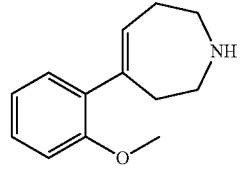

intermediate (66)
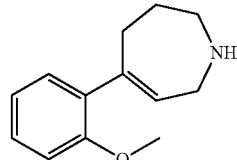

intermediate (67)
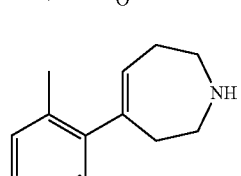

intermediate (68)
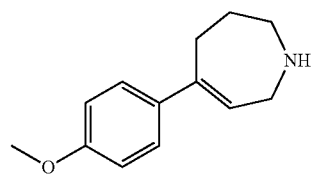

intermediate (69)
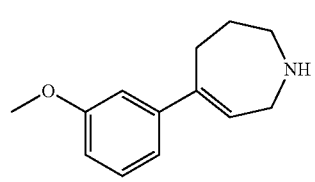

intermediate (70)
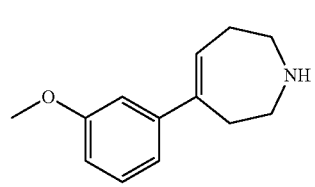

intermediate (71)
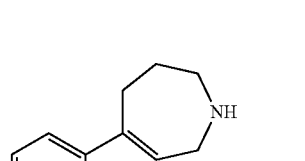

intermediate (72)
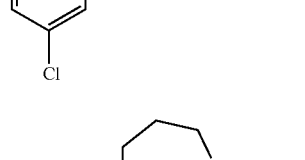

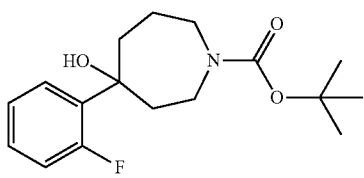

intermediate (73)

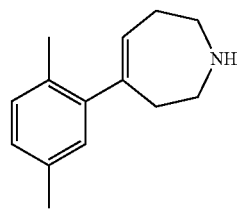

intermediate (76)

A solution of 1-bromo-2-fluoro-benzene (1.48 g, 8.5 mmol) in anhydrous THF (50 mL) was stirred under nitrogen at −78° C. for 30 minutes and then n-butyllithium (2.5 M in hexane, 3.5 mL, 10.1 mmol) was added dropwise −78° C. over 5 to 10 minutes and the formed mixture was stirred for 30 minutes. Then intermediate (A58) (1.5 g, 101 mmol) in THF (10 mL) was added via syringe. After addition, the cooling bath was removed. The reaction mixture was stirred for 1 hour, then quenched with 1N HCl (200 ml), The mixture was extracted with DCM (3×100 mL). The combined organic layers were separated and dried over anhydrous Na$_2$SO$_4$, then filtered and concentrated in vacuum. The residue was purified by column chromatograph over silica gel (eluent: petroleum ether/EtOAc 10/1). The pure fractions were collected and the solvent was evaporated, yielding 1.54 g of intermediate (A73).

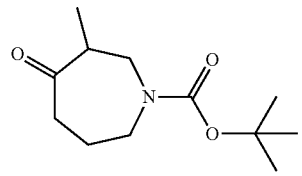

intermediate (A77)

To a solution of intermediate (A58) (5 g, 23 mmol) in THF (100 ml) was added LDA (23 ml, 46 mmol) at −78° C. The mixture was stirred for 0.5 hours at −50° C. Iodomethane (6.5 g, 46 mmol) was added to the mixture and stirred overnight at ambient temperature. The reaction mixture was quenched with 100 ml of brine. The organic layer was separated and the aqueous layer was extracted with EtOAc. The organic layers were combined and concentrated. The crude product was purified by column chromatography over silica gel (eluent: petroleum ether/EtOAc 9/1). The product fraction were collected and the solvent was evaporated, yielding 3 g of intermediate (A77).

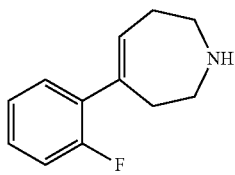

intermediate (A74)

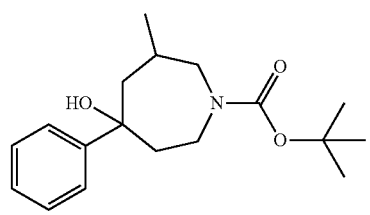

intermediate (A78)

To a solution of intermediate (A73) (1 g, 3.2 mmol) in DCM (20 mL) was added drop wise TFA (15 mL) at 0° C. After the addition, the mixture was stirred for 2 hours at room temperature. The reaction mixture was concentrated (<35° C.). The mixture was partitioned with brine (5 mL), Na$_2$CO$_3$ (5 g) and EtOAc (50 mL), the water layer was extracted with EtOAc (3×50 mL). The combined organic layers were dried over Na$_2$SO$_4$, filtrated and the solvent was evaporated. The residue was purified by column chromatography over silica gel (eluent: DCM/MeOH 30/1). The pure fractions were collected and the solvent was evaporated, yielding 0.6 g of intermediate (A74).

The following compounds were made using the same procedure as the example above whereby 1-bromo-2-fluoro-benzene was replaced by 2-bromo-1-fluoro-3-methoxy-benzene or 2-bromo-1,4-dimethyl-benzene respectively.

To a solution of intermediate (A77) (1.7 g, 7.5 mmol) in THF (50 ml) was added bromophenyl-magnesium (3M, 3.7 ml, 11.2 mmol) at 0° C. The mixture was stirred overnight at ambient temperature. The reaction mixture was quenched with 50 ml of brine. The organic layer was separated and the aqueous layer was extracted with EtOAc. The organic layers were combined and concentrated. The crude product was purified by column chromatography over silica gel (eluent: petroleum ether/EtOAc 1/1). The product fraction were collected and the solvent was evaporated, yielding 0.5 g of intermediate (A78).

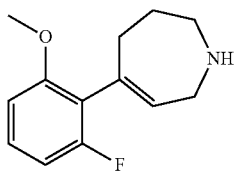

intermediate (75)

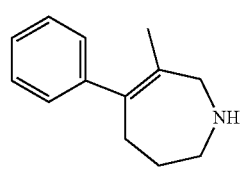

intermediate (A79)

A mixture of intermediate (A78) (0.5 g, 1.64 mmol) in HCl (10 ml, 6 mol/L in water) was refluxed overnight. The solvent was removed under reduced pressure. The residue was dissolved with 20 ml of water. The formed solution was basified pH to 10 with $K_2CO_3$. The resulting solution was extracted with EtOAc (4×50 ml). The organic layers were combined and concentrated, yielding 0.3 g of intermediate (A79).

Example B

Preparation of Intermediate B

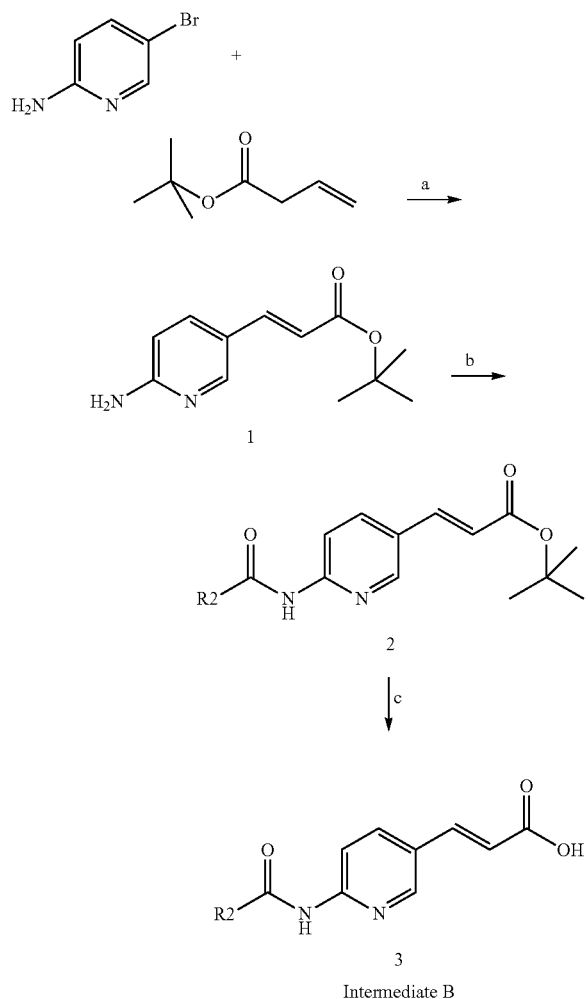

a) DIPEA, Pd(OAc)$_2$, tri-O-tolylphosphine, DMF, ACN, μW 180° C.; b) HATU, DIPEA, DMF, 70° C.; c) TFA, HCl in dioxane, DCM, RT Preparation of Intermediate (B3)

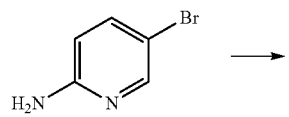

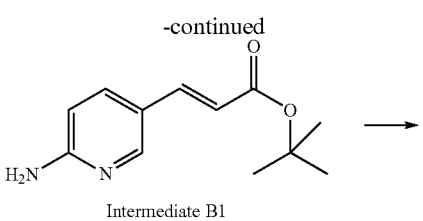

Intermediate B1

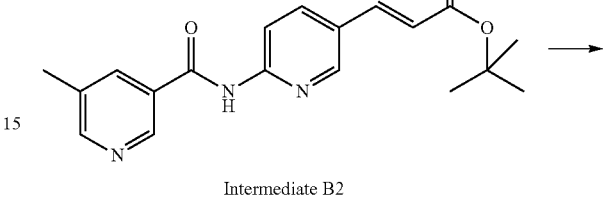

Intermediate B2

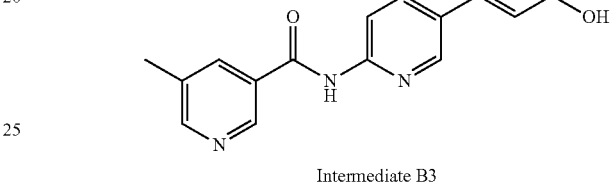

Intermediate B3

Preparation of Intermediate B1

A solution of 2-amino-5-bromopyridine (4 g, 23.12 mmol), tert-Butyl-acrylate (13.42 mL, 92.48 mmol) and N,N-diisopropylethylamine (7.64 mL, 46.24 mmol) in DMF (60 mL) and ACN (20 mL) was stirred and degased with $N_2$ for 10 minutes. Palladium acetate (0.52 g, 2.32 mmol) and Tri-O-tolylphosphine (1.41 g, 4.63 mmol) were added and the solution was heated at 180° C. using a multimode cavity microwave CEM® MARS system with a power output ranging from 0 to 400 W for 30 min. The reaction mixture was filtered through a short pad of Celite® and washed with EtOAc. The organic layer was washed with water, dried over MgSO$_4$, filtered and evaporated to dryness. The residue was purified by column chromatography over silica gel (SiOH 20-45 μm, 450 g, eluent: 0.1% NH$_4$OH, 97% DCM, 3% MeOH). Yielding: Intermediate B1 a pale yellow powder 3.55 g (70%)

Preparation of Intermediate B2

A solution of Intermediate B1 (0.8 g, 3.63 mmol), 5-methylnicotinic acid (0.9 g, 6.54 mmol), O-(7-Azabenzotriazol-1-yl)-N,N,N'N'-tetramethyluronium hexafluorophosphate CAS [148893-10-1] (2.49 g, 6.54 mmol) and N,N-diisopropylethylamine (1.4 mL, 7.99 mmol) in DMF dry (16 mL) was stirred overnight at 70° C. The mixture was poured out into water. The organic layer was extracted with CH$_2$Cl$_2$. The combined organic layers were washed with brine, dried over MgSO$_4$, filtered and concentrated. The residue was crystallized from EtOH to obtain a pale beige powder, Yielding: (50140532-AAA) 0.86 g (70%).

Preparation of Intermediate B3

Trifluoroacetic acid (4.9 mL, 63.35 mmol) was added to a solution of Intermediate B2 (0.86 g, 2.53 mmol) in CH$_2$Cl$_2$ (9 mL). The reaction mixture was stirred at room temperature for 4 hours, concentrated under reduce pressure and then triturated with Et₂O, filtered off and dried under vacuum. The residue was then triturated overnight in hydrogen chloride 4M in dioxane (8.2 mL, 32.94 mmol), the solid was filtered off, washed with Et₂O and dried under vacuum (70° C.). Yielding: Intermediate B3 white powder, 0.878 g, (99%).

Preparation of Intermediate B5

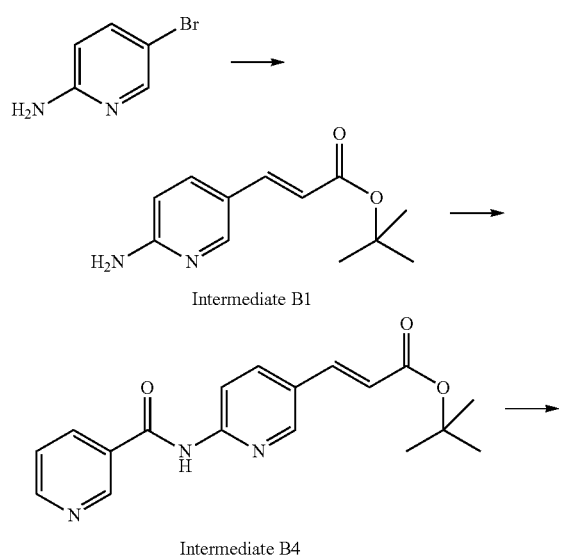

Preparation of Intermediate B4

Compound Intermediate B4 was prepared in the same way as Intermediate B2, starting from Intermediate B1 and nicotinic acid CAS [59-67-6]. Yielding: 0.35 g, 29%.

Preparation of Intermediate B5

Compound Intermediate B5 was prepared in the same way as Intermediate B3, starting from Intermediate B4. Yielding: 0.99 g, 99%.

Preparation of Intermediate B7

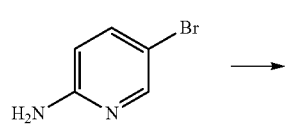

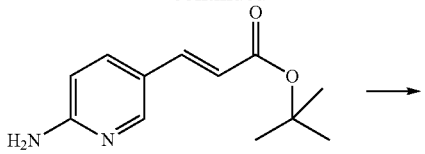

Intermediate B1

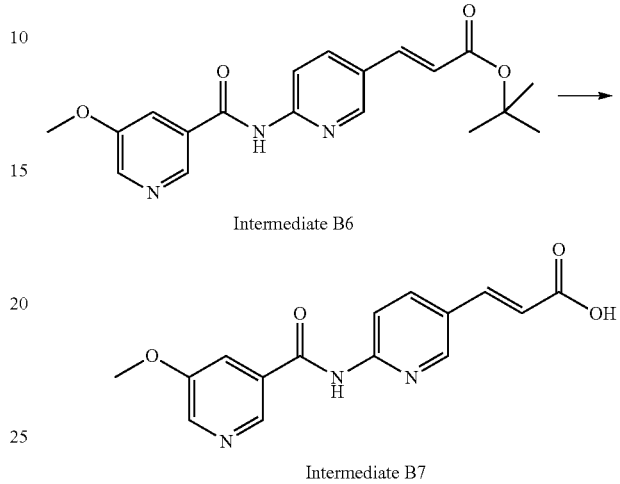

Preparation of Intermediate B6

Compound Intermediate B6 was prepared in the same way as Intermediate B2, starting from Intermediate B1 and 5-methoxynicotinic acid CAS [1044919-31-4]. Yielding: 0.74 g, 92%.

Preparation of Intermediate B7

Compound Intermediate B7 was prepared in accordance with the procedures to prepare Intermediate B3, starting from Intermediate B6. Yielding: 0.75 g, 97%.

Preparation of Intermediate B9

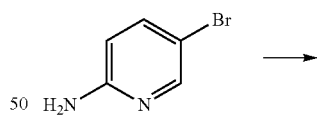

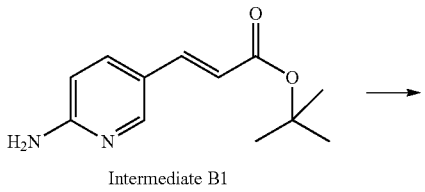

Intermediate B1

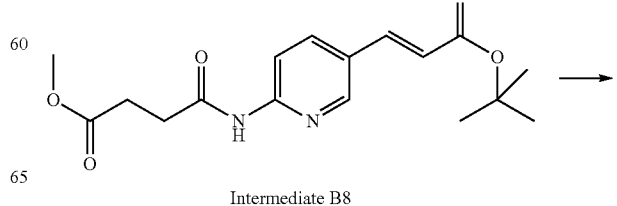

Intermediate B8

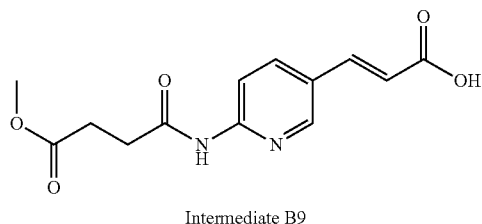

Intermediate B9

Preparation of Intermediate B8

Compound Intermediate B8 was prepared in the same way as Intermediate B2, starting from Intermediate B1 and monomethyl succinate CAS [3878-55-5]. Yielding: 0.76 g, 65%.

Preparation of Intermediate B9

Compound Intermediate B9 was prepared in the same way as Intermediate B3, starting from Intermediate B8. Yielding: 0.40 g, 99%.

Preparation of Intermediate B11

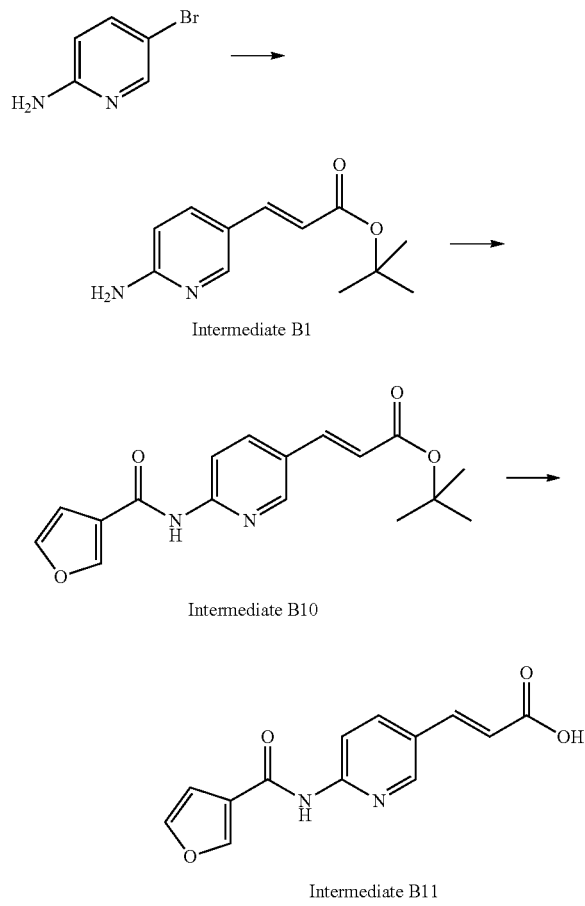

Preparation of Intermediate B10

Compound Intermediate B10 was prepared in the same way as Intermediate B2, starting from Intermediate B1 and 3-furoic acid CAS [488-93-7]. Yielding: 0.35 g, 49%.

Preparation of Intermediate B11

Compound Intermediate B11 was prepared in the same way as Intermediate B3, starting from Intermediate B10. Yielding: 0.38 g, 91%.

Example C

Final Compounds

Synthesis of Final Compounds (Compound C)

Preparation of Compound C1

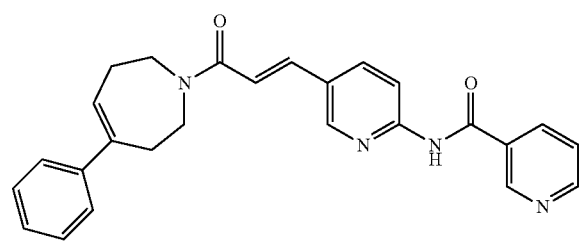 [SMILES: O=C(Nc1ccc(/C=C/C(=O)N2CCC=C(c3ccccc3)CC2)cn1)c1cccnc1]

The compound Compound C1 was prepared from 1H-Azepine, 2,3,6,7-tetrahydro-4-phenyl CAS [324784-75-95-4] (Intermediate A3) and Intermediate B5. About a 1:1 molar equivalent of the azepine and Intermediate B5, 1-hydroxybenzotriazole (about 1.2 molar equivalents, compared to Intermediate B5), coupling agent such as 1-(3-dimethylaminopropyl)-3-ethylcarbodiimide hydrochloride (e.g. about 1.2 molar equivalents, compared to Intermediate B5), base (e.g. triethylamine, e.g. about 3 molar equivalents compared to Intermediate B5) and solvent (e.g. dichloromethane, THF, or the like or mixtures thereof) were stirred (e.g. overnight) at room temperature. The mixture was poured out into water. The organic layer was extracted with $CH_2Cl_2$. The combined organic layers were washed with brine, dried over $MgSO_4$, filtered and concentrated. If possible, the residue may be crystallized 9 e.g. from ethanol or another suitable solvent), filtered off and dried under vacuum, optionally at elevated temperature.

Yielding: Compound C1 as a white powder 0.027 g, (21%). m.p. 186° C.

$^1$H NMR (500 MHz, DMSO-$d_6$) δ (ppm) 11.27 (s, 1H), 9.14 (s, 1H), 8.76 (d, J=4.41 Hz, 1H), 8.71 (br. s., 1H), 8.36 (d, J=7.88 Hz, 1H), 8.28-8.33 (m, 1H), 8.22-8.27 (m, 1H), 7.51-

7.59 (m, 2H), 7.27-7.40 (m, 5H), 7.20-7.26 (m, 1H), 5.97-6.07 (m, 1H), 3.67-3.98 (m, 4H), 2.72-2.83 (m, 2H), 2.51-2.60 (m, 2H).

Preparation of Compound C2

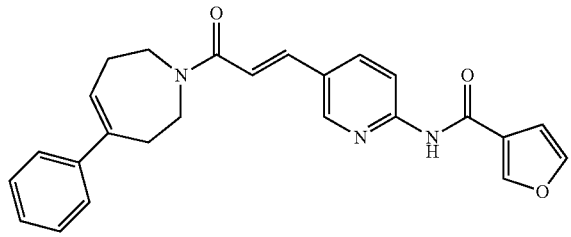 [SMILES: O=C(Nc1ccc(/C=C/C(=O)N2CCC=C(c3ccccc3)CC2)cn1)c1ccoc1]

The compound Compound C2 was prepared in the same way as Compound C1, starting from 1H-Azepine, 2,3,6,7-tetrahydro-4-phenyl CAS [324784-75-95-4] (Intermediate A3) and Intermediate B11. Yielding: Compound C2 as a white powder 0.024 g, (6%). m.p. 156° C.

$^1$H NMR (500 MHz, DMSO-d$_6$) δ (ppm) 10.82 (s, 1H), 8.67 (br. s., 1H), 8.57 (s, 1H), 8.24-8.30 (m, 1H), 8.18-8.24 (m, 1H), 7.80 (s, 1H), 7.53 (d, J=15.45 Hz, 1H), 7.27-7.37 (m, 5H), 7.20-7.26 (m, 1H), 7.08 (s, 1H), 6.07-6.00 (m, 1H), 3.66-3.97 (m, 4H), 2.74-2.83 (m, 2H), 2.54 (m, 2H).

Synthesis of Final Compounds in which R$^x$ Represents Ring (ii)

Synthesis of Final Compounds F

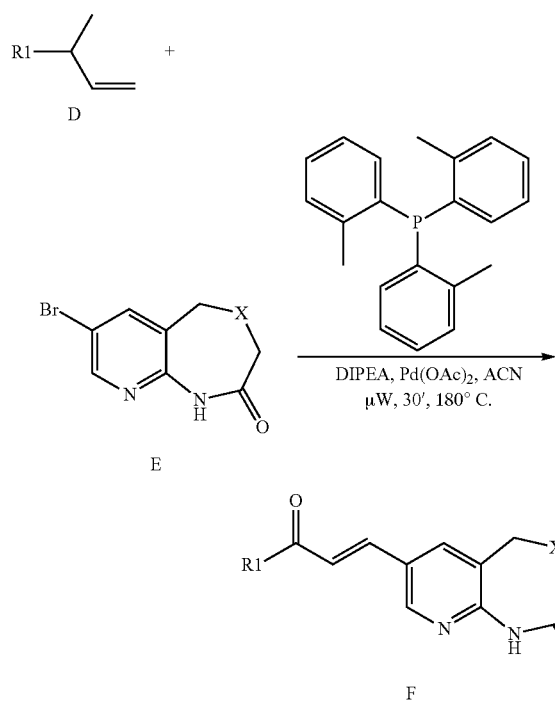

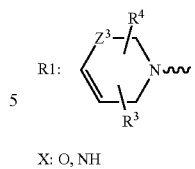

X: O, NH

Preparation of Intermediate D

Preparation of Intermediate D1

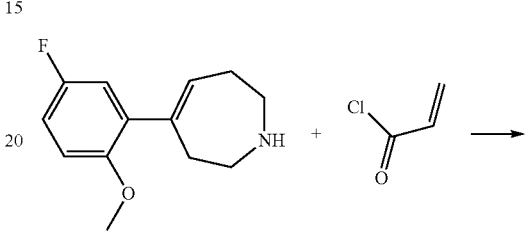

Intermediate D1

Compound Intermediate D1 was prepared from 2,3,6,7-tetrahydro-4-(4-fluoro-2-methoxyphenyl)-azepine (which was prepared in accordance with the procedures described herein; see for example preparation of Intermediates A above) whereby a solution of acryloyl chloride (e.g. at least one equivalent, such as about 1.2 equivs) in solvent (e.g. DCM) was added dropwise to the starting material (2,3,6,7-tetrahydro-4-(4-fluoro-2-methoxyphenyl)-azepine; 1 equiv) and base (e.g. triethylamine, at least 1 equiv. such as about 1.2 equiv.) in solvent (e.g. DCM), which mixture may be stirred at room temperature, after which the reaction can be worked up (e.g. by adding water and DCM, separating the organic layer, washing with water, drying with MgSO$_4$ and evaporating to dryness) and the product isolated in accordance with standard procedures (e.g. chromatography). Yielding: 0.27 g, 65%.

Preparation of intermediate E

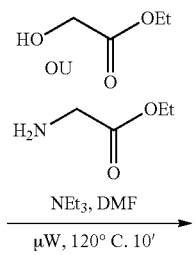

CAS[769109-93-5]

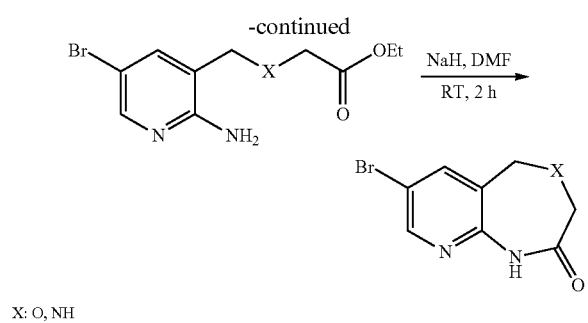

X: O, NH

Preparation of Intermediate E2

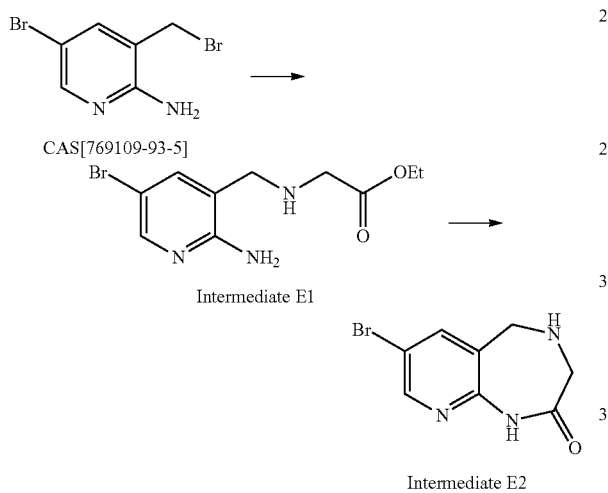

Preparation of Intermediate E1

A mixture of glycine methyl ester hydrochloride (4.93 g, 39.3 mmol), 2-amino-5-bromo-3-bromoethylpyridine (10 g, 19.7 mmol) and triethylamine (13.7 mL, 98.3 mmol) in DMF (100 mL), in a sealed tube, was heated at 120° C. using a single mode microwave (Biotage® Initiator EXP 60) with a power output ranging from 0 to 400 W for 10 min. $CH_2Cl_2$ and the minimum of water were added, the organic layer was separated, dried ($MgSO_4$) and evaporated till dryness The residue (6 g) was purified by flash chromatography over silica gel (120 g, 15-40 nm, mobile phase 100% $CH_2Cl_2$). The pure fractions were collected and concentrated to afford 3 g of Intermediate E1.

Preparation of Intermediate E2

Under $N_2$ flow, NaH (0.8 g, 20.1 mmol) was added portionwise to a solution of Intermediate E1 (4.6 g, 16.8 mmol) in DMF (50 mL) at 5° C. then the mixture was stirred for 2 hours at room temperature. EtOAc and the minimum of water were added, the organic layer was separated, the aqueous layer was saturated with NaCl and extracted with EtOAc. The combined organic layers were dried ($MgSO_4$) and evaporated until dryness. The residue was crystallized from EtOH, the precipitate was filtered off and dried under vacuum to give 1.5 g (37%) of Intermediate E2.

Preparation of Intermediate E4

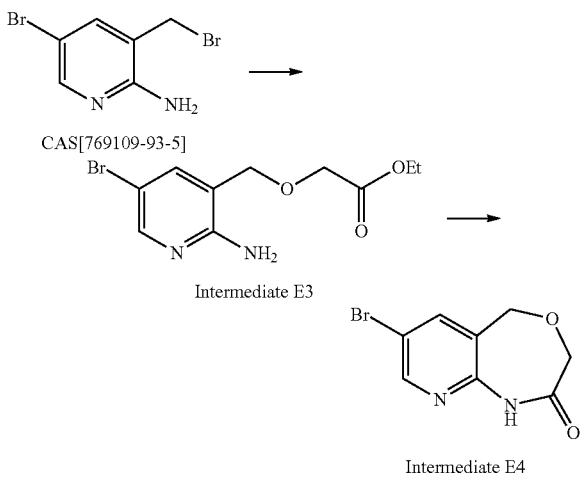

Preparation of Intermediate E3

Intermediate E3 was prepared in the same way as Intermediate E1, starting from 2-amino-5-bromo-3-bromoethylpyridine and ethyl glycolate. Yielding: 1.2 g, 22%.

Preparation of Intermediate E4

Intermediate E4 was prepared in the same way as Intermediate E2, starting from Compound 4. Yielding: 1.2 g, 27%.

Synthesis of Final Compound F

Preparation of Compound F1

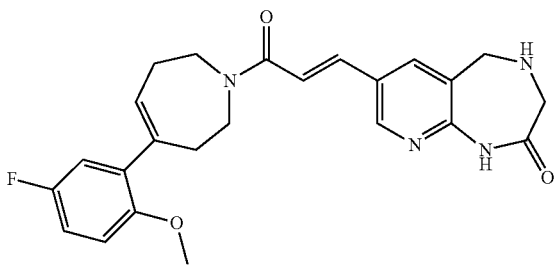 [SMILES: COc1ccc(F)cc1C1=CCCN(C(=O)/C=C/c2cnc3c(c2)CNCC(=O)N3)CC1]

The compound Compound F1 was prepared in the same way as hereinbefore described, starting from Intermediate E2 and Intermediate D1. Intermediate D1 (1.5 equivs.) and intermediate E2 (1 equiv.) in an appropriate solvent (e.g. acetonitrile and DMF, or the like) are stirred and degassed with $N_2$ for 10 minutes. Palladium acetate (cat.) and tri-O-tolylphosphine are added in a sealed tube. The solution is heated at 180° C. using a monomode microwave (Biotage® Initiator EXP 60) with a power output ranging from 0 to 400 W for 30 min. The reaction mixture is worked up and the desired product isolated (e.g. by chromatography). Yielding: Compound F1 0.170 g, (32%). m.p. 192° C.

¹H NMR (400 MHz, DMSO-d₆) δ 9.72 (br. s., 1H), 8.42 (s, 1H), 7.97 (br. s., 1H), 7.50 (d, J=15.2 Hz, 1H), 7.22 (d, J=15.2 Hz, 1H), 6.85-7.07 (m, 3H), 5.73-5.80 (m, 1H), 3.60-3.98 (m, 11H), 2.97 (br. s., 1H), 2.59 (br. s., 2H), 2.44 (br. s., 2H).

Example G

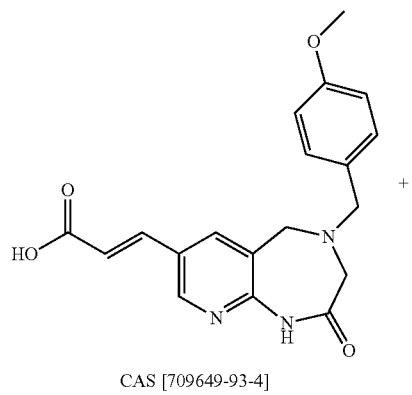

CAS [709649-93-4]

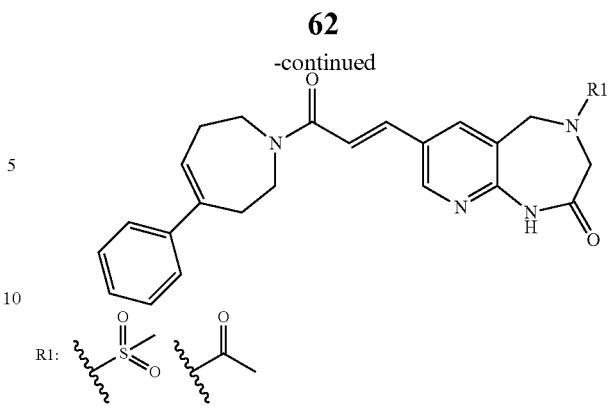

a) HOBT, EDCI, NEt₃, DCM, THF, RT, 18 h; b) chloroethyl chloroformate, DCE, MeOH, 50° C., 1h; c) NaH, DMF, RT, 3 h.

Preparation of Compound G1

A mixture of CAS [709649-93-4] (3.37 g, 5.80 mmol), CAS [324784-95-4] (1.21 g, 6.96 mmol; Intermediate A3), N'(ethylcarbonimidoyl)-N,N-dimethyl-1,3-propanediamine (1.33 g, 6.96 mmol), 1-hydroxybenzotriazole (0.94 g, 6.96 mmol) and triethylamine (1.93 mL, 13.9 mmol) in CH₂Cl₂ (70 mL) and THF (70 mL) was stirred overnight at room temperature. Water and CH₂Cl₂ were added, the organic layer was separated, washed with water, dried (MgSO₄) and evaporated until dryness. The residue (3.13 g) was taken up in EtOH, filtered off and dried (vacuum, 60° C.) to give 2.56 g (87%) of Compound G1.

Preparation of Compound G2

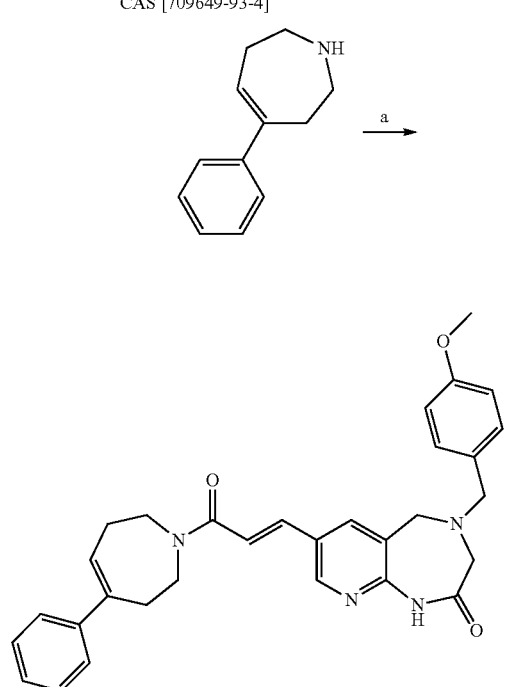

Compound G1

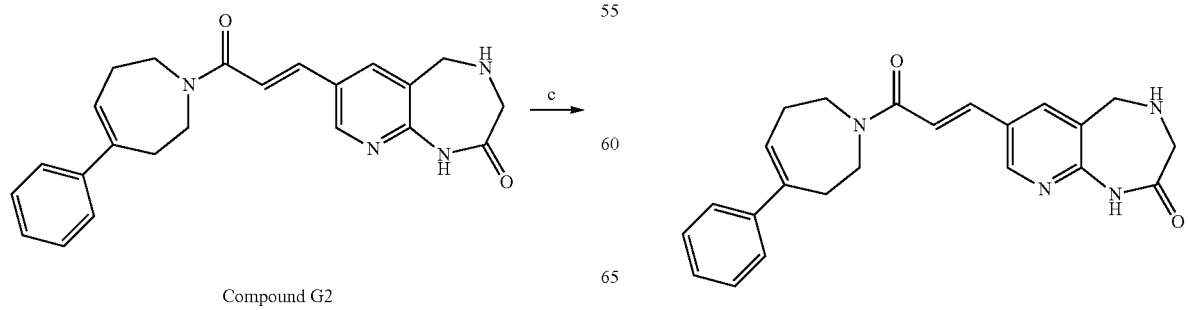

Compound G2

1-chloroethyl chloroformate (0.064 mL, 0.59 mmol) was added to a solution of Compound G1 (250 mg, 0.49 mmol) in MeOH (5 mL) then the mixture was stirred at 80° C. for 1 hour and evaporated till dryness. Then, dichloroethane (5 mL) was added to the resulting precipitate and the mixture was stirred to 50° C. for 1 hour. The resulting mixture was evaporated until dryness. Then, the remaining precipitate was taken up with K$_2$CO$_3$ (10%) and EtOAc, the organic layer was separated, washed with water and brine, dried (MgSO$_4$) and evaporated till dryness. The residue (0.3 g) was purified by flash chromatography over silica gel (15-40 μam 10 g, mobile phase gradient from 100% CH$_2$Cl$_2$ to 96% CH$_2$Cl$_2$, 4% CH$_3$OH, 0.1% NH$_4$OH). The pure fractions were collected and evaporated to dryness. The residue (0.080 g) was crystallized from EtOH, the precipitate was filtered off and dried to afford 0.050 g (26%) of 448162946-AAA (Compound G2). m.p. 216° C.

Preparation of Compound G3

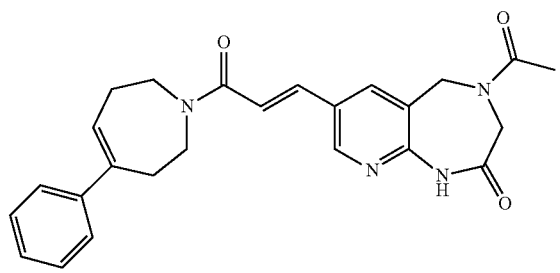 [SMILES: CC(=O)N1CC(=O)Nc2ncc(/C=C/C(=O)N3CCC=C(c4ccccc4)CC3)cc2C1]

Acetyl chloride (14.6 μL, 0.21 mmol) was added to a solution of Compound G2 (50 mg, 0.13 mmol) in triethylamine (21.5 μL, 0.15 mmol) and CH$_2$Cl$_2$ (2 mL). The mixture was stirred at room temperature for the night. Water and CH$_2$Cl$_2$ were added, the organic layer was separated, washed with water, dried (MgSO$_4$) and evaporated until dryness to give 0.053 g of Compound G3.

$^1$H NMR (400 MHz, DMSO-d$_6$) δ 9.88 (br. s., 1H), 8.49 (br. s., 1H), 8.10 (s, 1H), 7.49 (d, J=15.5 Hz, 1H), 7.19-7.37 (m, 6H), 5.99-6.05 (m, 1H), 4.71 (br. s., 2H), 4.44 (s, 2H), 3.76-3.92 (m, 4H), 2.77-2.84 (m, 2H), 2.52-2.58 (m, 2H), 2.05 (s, 3H).

Preparation of Compound G4

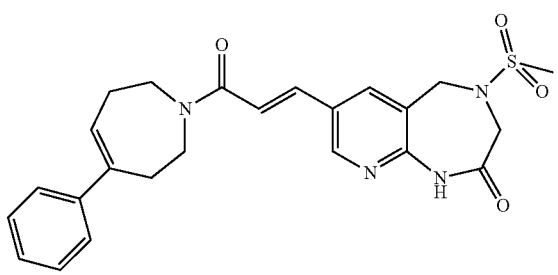 [SMILES: CS(=O)(=O)N1CC(=O)Nc2ncc(/C=C/C(=O)N3CCC=C(c4ccccc4)CC3)cc2C1]

The compound Compound G4 was prepared in the same way as compound Compound G3, starting from Compound G2 and methanesulfonylchloride. Yielding: 0.030 g, (50%).

$^1$H NMR (400 MHz, DMSO-d$_6$) δ 10.28 (br. s., 1H), 8.56 (s, 1H), 8.20 (s, 1H), 7.50 (d, J=16 Hz 1H), 7.19-7.37 (m, 6H), 6.02 (m, 1H), 4.55 (s, 2H), 4.15 (s, 2H), 3.72-3.96 (m, 4H), 2.98 (s, 3H), 2.80 (m, 2H), 2.54 (m, 2H).

Example H

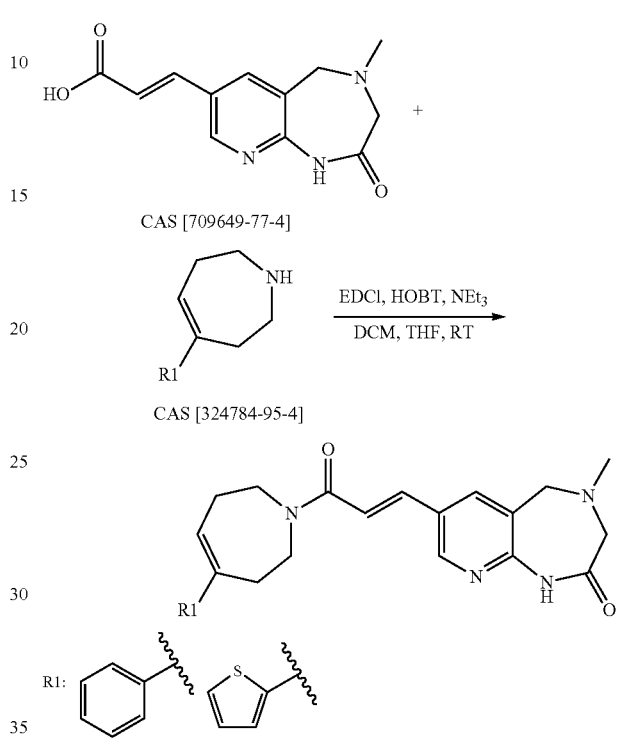

Preparation of Compound H1

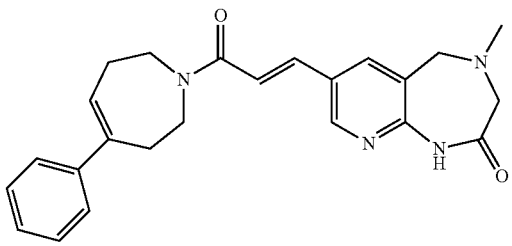 [SMILES: CN1CC(=O)Nc2ncc(/C=C/C(=O)N3CCC=C(c4ccccc4)CC3)cc2C1]

A mixture of CAS [709649-77-4] (2.2 g, 4.57 mmol), CAS [324784-95-4] (0.95 g, 5.48 mmol; Intermediate A3), N'(ethylcarbonimidoyl)-N,N-dimethyl-1,3-propanediamine (1.05 g, 5.48 mmol), 1-hydroxybenzotriazole (0.74 g, 5.48 mmol) and triethylamine (2.2 mL, 15.9 mmol) in CH$_2$Cl$_2$ (40 mL) and THF (40 mL) was stirred for 48 hours at room temperature. Water and CH$_2$Cl$_2$ were added, the organic layer was separated, washed with water, dried (MgSO$_4$) and evaporated until dryness. The residue (3.13 g) was taken up in EtOH, filtered off and dried (vacuum, 60° C.) to give 1.42 g (77%) of Compound H1. m.p. 201° C.

$^1$H NMR (500 MHz, DMSO-d$_6$) δ 10.37 (s, 1H), 8.52 (s, 1H), 8.17 (br. s., 1H), 7.47-7.53 (m, 1H), 7.20-7.37 (m, 6H), 5.99-6.07 (m, 1H), 3.67-3.96 (m, 6H), 3.42 (s, 2H), 2.74-2.82 (m, 2H), 2.52-2.48 (m, 2H), 2.37 (s, 3H).

Preparation of Compound H2

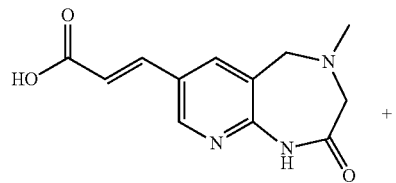

CAS[709649-77-4]

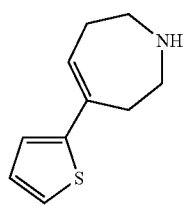

Intermediate A47

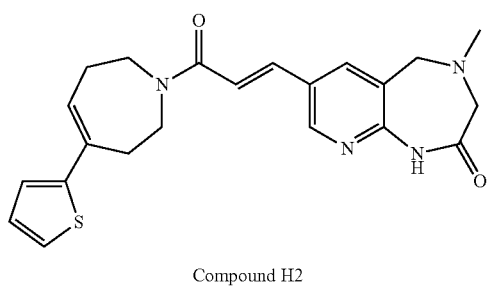

Compound H2

The compound Compound H2 was prepared in the same way as compound Compound H1, starting from CAS [709649-77-4] and Intermediate A47 (which was prepared in according with the procedures described herein; see preparation of Intermediate A). Yielding: Compound H2, 0.06 g (7.5%).

Example I

Intermediates I

Preparation of Final Compounds from Intermediate I (e.g. I4)

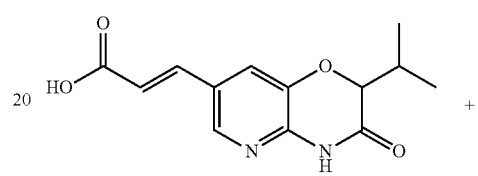

Intermediate I4

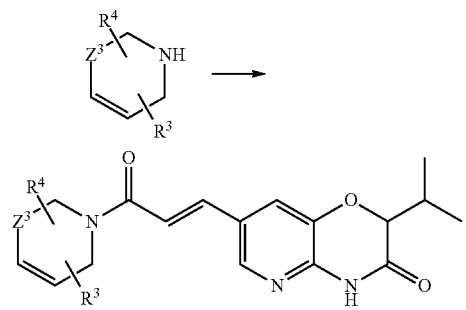

Preparation of Intermediate I4

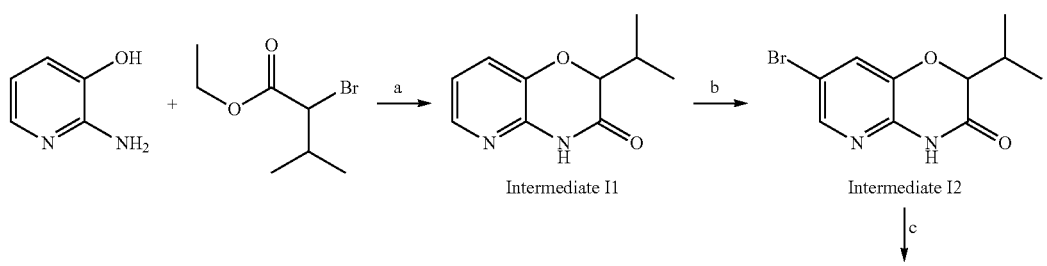

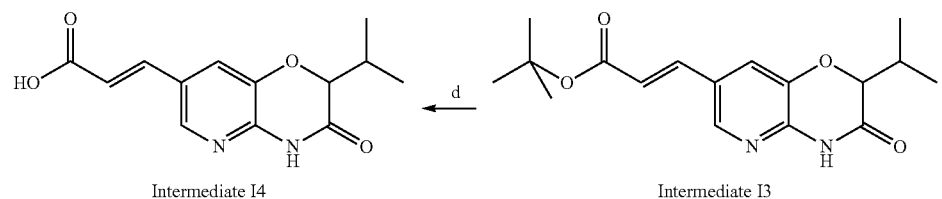

a) NaH, DMF, 80° C.; b) Br$_2$, DMF, RT; c) DIPEA, Pd(OAc)$_2$, tri-O-tolylphosphine, DMF, ACN, μW, 180° C.; d) TFA, HCl in dioxane, DCM, RT Preparation of Intermediate I1

To a suspension of NaH (0.77 g, 19.23 mmol) in DMF (15 mL) was added dropwise a solution of 2-amino-3-hydroxypyridine (3 g, 27.24 mmol) in DMF (15 mL) at room temperature over a period of 10 minutes and the mixture was stirred at room temperature for 20 minutes. To the mixture was added dropwise ethyl-2-bromo-isovalerate CAS [609-12-1] (2.63 mL, 16.03 mmol) over a period of 20 minutes, the reaction mixture was stirred at room temperature for 1 hour and at 80° C. for 2 hours. After cooling, cold water was added, and the mixture was extracted with EtOAc. The organic layer was successively washed with water and brine, dried over MgSO$_4$ and concentrated under reduced pressure. The residue was purified by flash chromatography over silica gel (80 g, mobile phase gradient Heptane/EtOAc from 85/15 to 70/30). Pure fractions were collected and the solvent was removed. Yielding: Intermediate I1 as a white powder, 1.14 g, (37%).

Preparation of Intermediate I2

To a solution of Intermediate I1 (1.14 g, 3.26 mmol) in DMF (24 mL) was added dropwise bromine (0.23 mL, 4.57 mmol). The reaction mixture was stirred overnight at room temperature. The reaction mixture was poured out into water under vigorous stirring. EtOAc was added, the organic layer was separated, dried over MgSO$_4$, filtered off and evaporated. The residue was crystallized from EtOH and dried. Yielding: Intermediate I2, 0.66 g, (75%).

Preparation of Intermediate I3

Compound Intermediate I3 was prepared in accordance with the procedures to prepare Intermediate B1 (described hereinbefore), starting from Intermediate I2 and tert-Butyl-acrylate. Yielding: a white powder 0.31 g (40%).

Preparation of Intermediate I4

Compound Intermediate I4 was prepared in accordance with the procedures to prepare Intermediate B3 (as hereinbefore described), starting from Intermediate I3. Yielding: a white powder 0.29 g (89%).

Synthesis of Final Compounds in which R$^x$ Represents Ring (iii)

Intermediate Examples J and Final Examples K

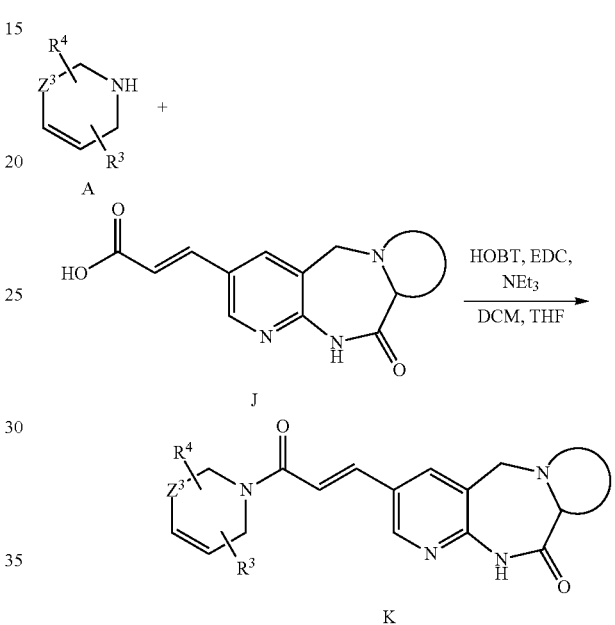

Preparation of Intermediate A

These are/were prepared as hereinbefore described.

Preparation of Intermediate J

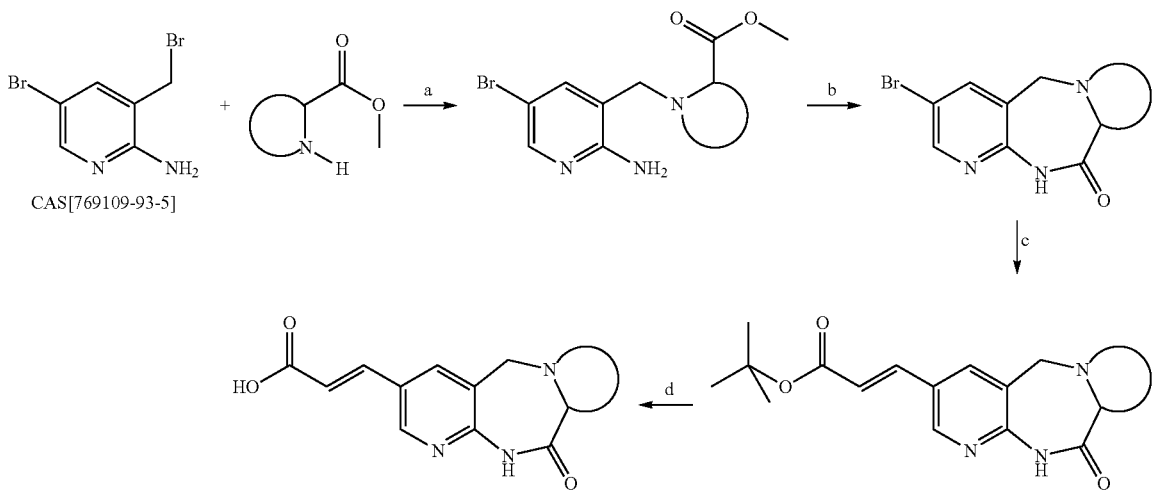

a) Et₃N, DMF, μW; b) NaH, DMF, RT; c) DIPEA, Pd(OAc)₂, tri-O-tolylphosphine, DMF, ACN, μW; d) TFA, HCl, DCM, RT Preparation of Intermediate J4

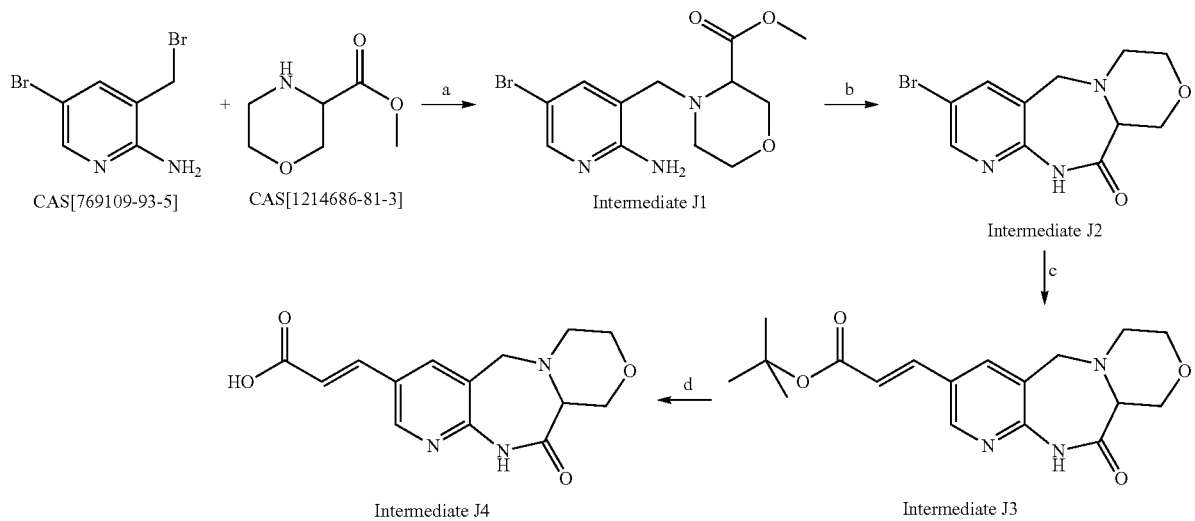

Preparation of Intermediate J1

A solution of 2-Amino-5-bromo-3-(bromomethyl)pyridine (15.2 g, 30.3 mmol), 3-morpholinecarboxylic acid methyl ester hydrochloride (5.5 g, 30.3 mmol) and triethylamine (21 mL, 151 mmol) in DMF (150 mL) and the solution was heated at 120° C. using a multimode cavity microwave CEM® MARS system with a power output ranging (50%) from 0 to 400 W for 10 min in open vessel. Water and EtOAc were added, the organic layer was separated, washed with water, brine, dried over MgSO₄, filtered and evaporated to dryness, Yielding: Intermediate J1 11.2 g (quantitative).

Preparation of Intermediate J2

NaH was added portionwise to a solution of Intermediate J1 (13.3 g, 40.3 mmol) in DMF (100 mL) at room temperature then the mixture was stirred for 5 hours. Water and EtOAc were added, the precipitate was filtered off. The organic layer was separated, washed with water then brine, dried (MgSO₄) and evaporated till dryness. The residue and the precipitate were gathered and crystallized from EtOH. Yielding: Intermediate J2 5 g (42%).

Preparation of Intermediate J3

A solution of Intermediate J2 (4 g, 13.42 mmol), tert-Butyl-acrylate (7.8 mL, 53.7 mmol) and N,N-diisopropylethylamine (4.4 mL, 26.83 mmol) in DMF (30 mL) and ACN (80 mL) was stirred and degassed with N₂ for 10 minutes. Palladium acetate (0.3 g, 1.34 mmol) and Tri-O-tolylphosphine (0.82 g, 2.68 mmol) were added and the solution was heated at 180° C. using a multimode cavity microwave CEM® MARS system with a power output ranging from 0 to 400 W for 30 min. The reaction mixture was filtered through a short pad of Celite® and washed with EtOAc. The organic layer was washed with water, dried over MgSO₄, filtered and evaporated to dryness. The residue was taken up EtOH, filtered and dried vacuum, Yielding: Intermediate J3 3.1 g (67%)

Preparation of Intermediate J4

Trifluoroacetic acid (17.5 mL, 227.25 mmol) was added to a solution of Intermediate J3 (3.1 g, 8.97 mmol) in CH₂Cl₂ (30 mL). The reaction mixture was stirred at room temperature for 30 minutes, concentrated under reduce pressure and then triturated with Et₂O, filtered off and dried under vacuum. Yielding: Intermediate J4 3.6 g (99%).

Preparation of Intermediate J8

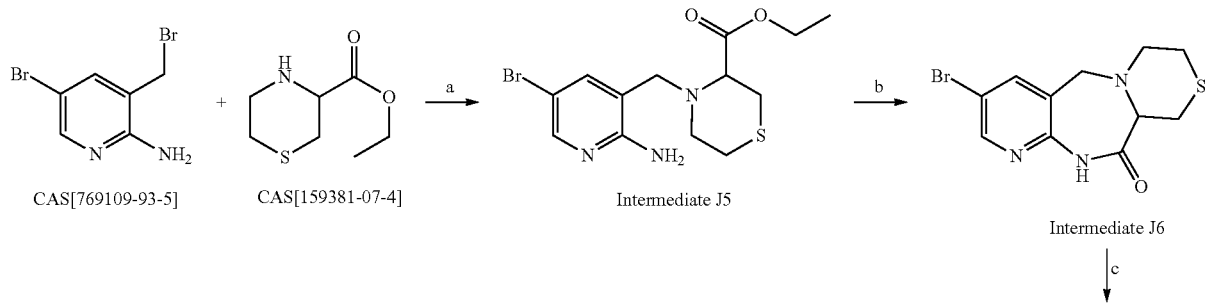

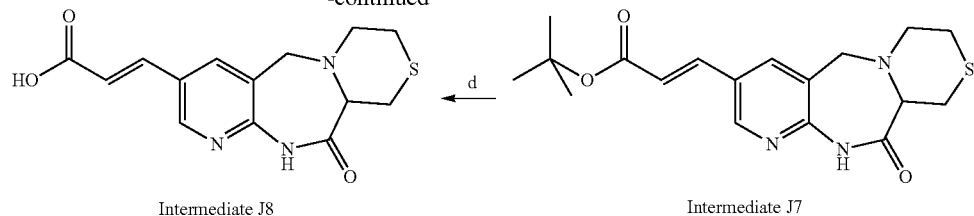

Intermediate J8          Intermediate J7

Preparation of Intermediate J5

Intermediate J5 was prepared in the same way as Intermediate J1, starting from 2-Amino-5-bromo-3-(bromomethyl)pyridine CAS [769109-93-5] and ethyl thiomorpholine-3-carboxylate hydrochloride[159381-07-4]. Yielding: 2 g, quantitative.

Preparation of Intermediate J6

Compound Intermediate J6 was prepared in the same way as Intermediate J2, starting from Intermediate J5. Yielding: 0.65 g, 46%.

Preparation of Intermediate J7

Compound Intermediate J7 was prepared in the same way as Intermediate J3, starting from Intermediate J6. Yielding: 0.57 g, 76%.

Preparation of Intermediate J8

Compound Intermediate J8 was prepared in the same way as Intermediate J4, starting from Intermediate J7. Yielding: 0.66 g, 99%.

Preparation of Intermediate J14

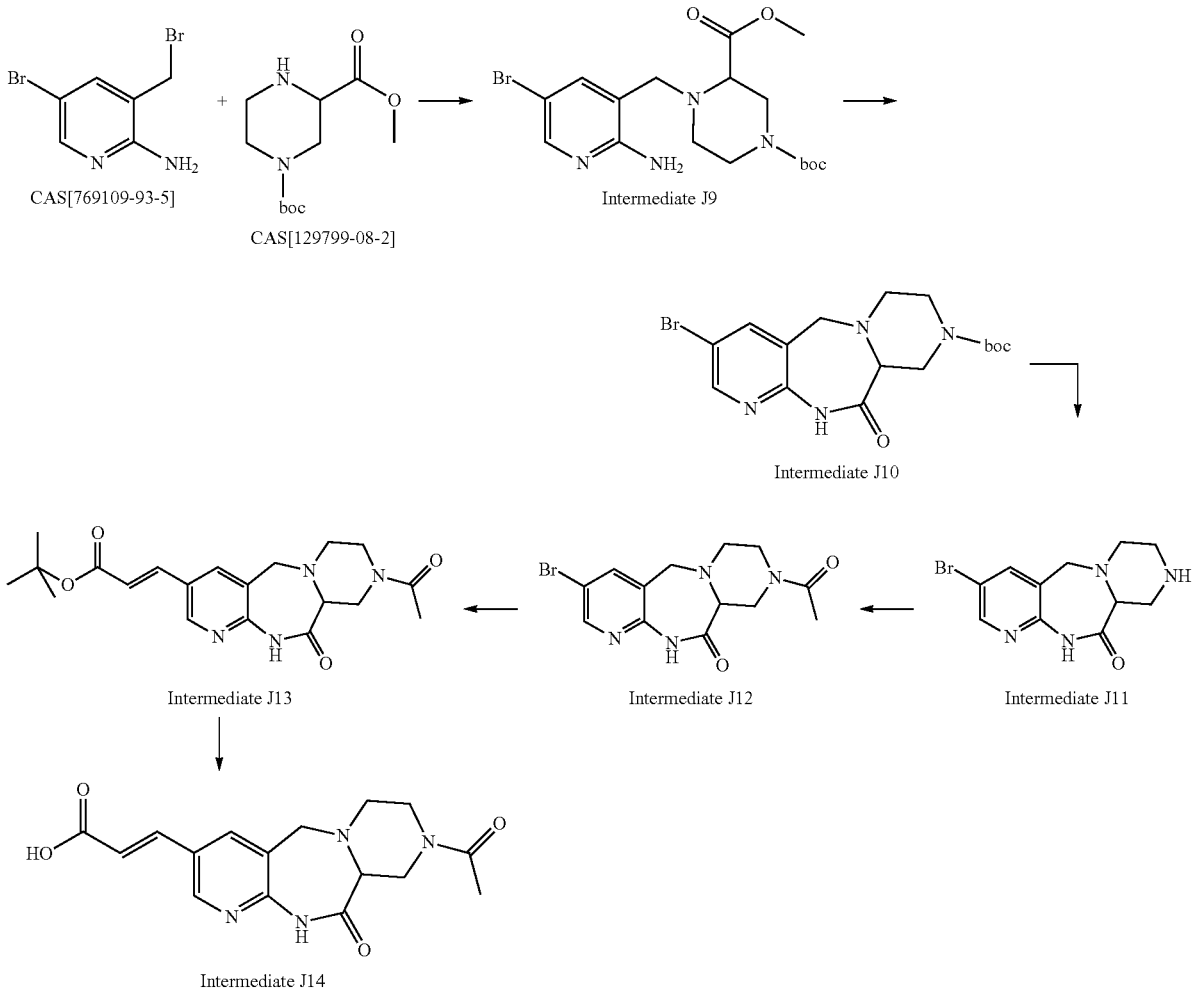

Preparation of Intermediate J9

Intermediate J9 was prepared in the same way as Intermediate J1, starting from 2-Amino-5-bromo-3-(bromomethyl)pyridine CAS [769109-93-5] and 1-(1,1-dimethyl-ethyl)-3-methylester-1,3-piperazine dicarboxylic acid [129799-08-2]. Yielding: as brown gum 36 g, quantitative.

Preparation of Intermediate J10

Intermediate J10 was prepared in the same way as Intermediate J2, starting from Intermediate J9. Yielding: Intermediate J10 as white powder 13.8 g, 60%.

Preparation of Intermediate J11

Trifluoroacetic acid (15.5 mL, 201 mmol) was added to a suspension of Intermediate J10 (8.00 g, 20.1 mmol) in DCM (90 mL). The mixture was stirred at room temperature for 20 hours and concentrated under reduced pressure. The residue was dissolved in dichloromethane (200 mL) and washed with saturated aqueous NaHCO$_3$ solution (200 mL). The aqueous layer was extracted with dichloromethane (20×50 mL). The combined organic layers were dried (Na$_2$SO$_4$), filtered and concentrated under reduced pressure. Yielding: Intermediate J11 as yellow solid 6 g, 100%.

Preparation of Intermediate J12

Acetyl chloride (1.86 mL, 26.0 mmol) was added to a solution of Intermediate J11 (5.95 g, 20.0 mmol) and triethylamine (3.91 mL, 28.0 mmol) in DCM (100 mL) at 0° C. The mixture was allowed to reach room temperature and was stirred for 3 days. The reaction mixture was diluted with dichloromethane (150 mL) and washed with water (250 mL). The organic layer was dried (Na$_2$SO$_4$), filtered and concentrated under reduced pressure. The residue was triturated in ethanol (30 mL) and vacuum-dried. Yielding: Intermediate J12 as a white solid 1.41 g, 21%.

Preparation of Intermediate J13

Intermediate J13 was prepared in the same way as Intermediate J3, starting from Intermediate J12. Yielding: Intermediate J13 as an orange foam 1.38 g, 86%.

Preparation of Intermediate J14

Intermediate J14 was prepared in the same way as Intermediate J4, starting from Intermediate J13. Yielding: Intermediate J14 as a white product 1 g, 94%.

Preparation of Intermediate J16

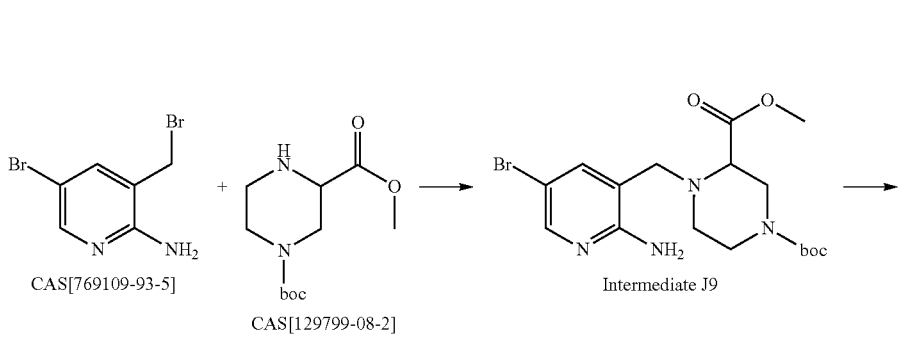

CAS[769109-93-5] + CAS[129799-08-2] → Intermediate J9

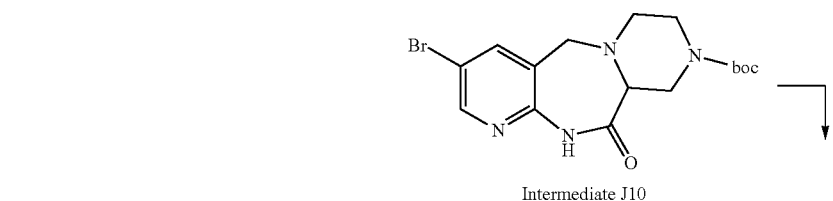

Intermediate J10

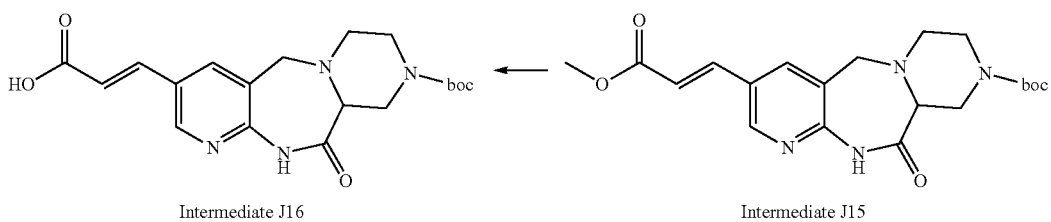

Intermediate J16 ← Intermediate J15

Preparation of Intermediate J15

Intermediate J10 (4.30 g, 10.8 mmol) was suspended in a mixture of DMF (20 mL) and acetonitrile (60 mL). Methyl acrylate (2.92 mL, 32.5 mmol), diisopropylethylamine (3.96 mL, 22.7 mmol), and tri-o-tolylphosphine (0.659 g, 2.16 mmol) were added. The resulting mixture was purged with argon and palladium acetate (0.243 g, 1.08 mmol) was added. The mixture was purged with argon again and stirred under reflux (oil bath 110° C.) for 19 hours. The reaction mixture was concentrated under reduced pressure. The residue was dissolved in ethyl acetate (500 mL) and washed with saturated aqueous NaHCO$_3$ solution (300 mL), then with brine (300 mL). The organic layer was dried (Na$_2$SO$_4$), filtered and concentrated. The residue (6.15 g) was purified by column chromatography over silica gel (mobile phase gradient ethyl acetate/methanol 100/0 to 95/5). The product fractions were collected and the solvent was evaporated. The residue was triturated in ethanol (30 ml) and vacuum-dried (40° C., 1 h). Yielding: Intermediate J15 as a white solid 3.37 g, (77%).

Preparation of Intermediate J16

Sodium hydroxide (0.670 g, 16.7 mmol) and water (8 mL) were added to a solution of Intermediate J15 (3.37 g, 8.38 mmol) in THF (32 mL). The mixture was stirred at room temperature for 20 hours and then was concentrated under reduced pressure. The residue was dissolved in water (30 mL) and conc. HCl (~1.4 mL) was added until pH~5-6. The precipitate was filtered off on a glass frit, washed with water (15 mL) and vacuum-dried. Yielding: as a white solid 2.45 g, (75%).

Preparation of Intermediate J20

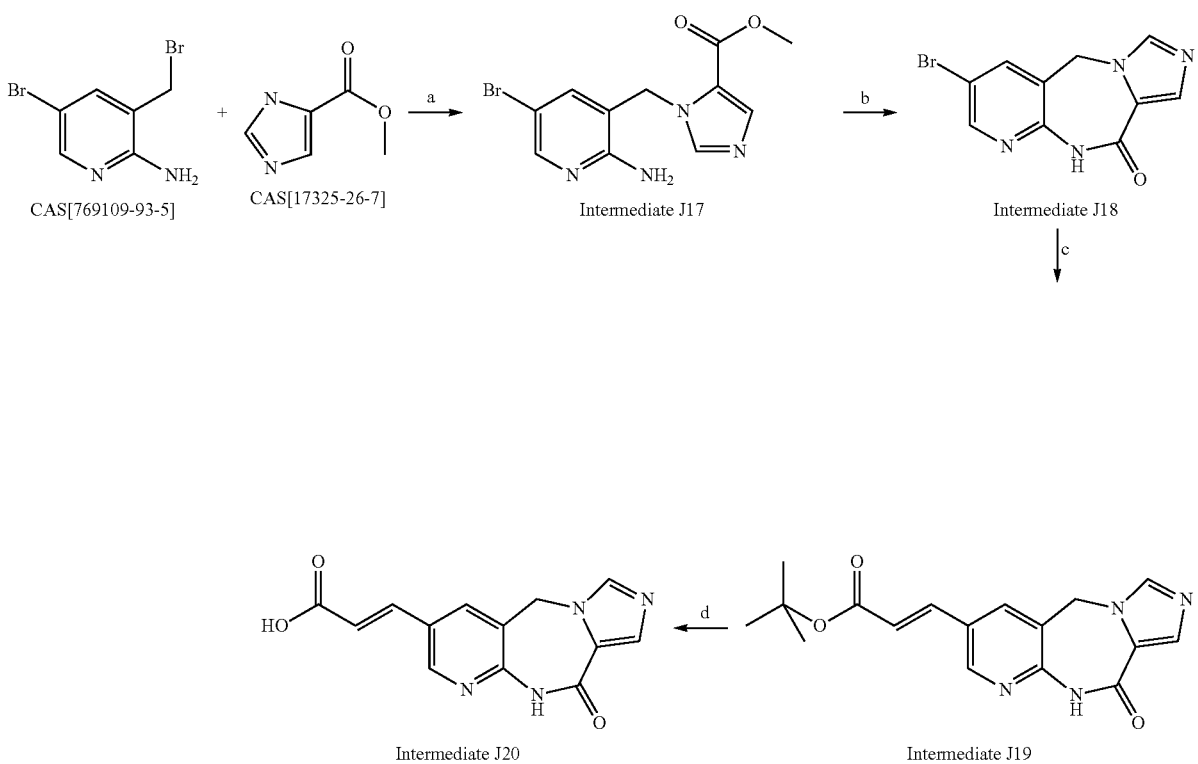

77
Intermediate J17

Intermediate J17 was prepared in the same way as Intermediate J1, starting from 2-Amino-5-bromo-3-(bromomethyl)pyridine CAS [769109-93-5] and 1H-Imidazole-5-carboxylic acid, methyl ester [17325-26-7]. Yielding: 1.42 g, 11%.

Intermediate J18

Intermediate J18 was prepared in the same way as Intermediate J2, starting from Intermediate J17. Yielding: 0.54 g, 49%.

Intermediate J19

Intermediate J19 was prepared in the same way as Intermediate J3, starting from Intermediate J18. Yielding: 0.17 g, 29%.

Intermediate J20

Intermediate J20 was prepared in the same way as Intermediate J4, starting from Intermediate J19. Yielding: 0.23 g, 66%.

78
Synthesis of Final Compounds K

Preparation of Compound K1

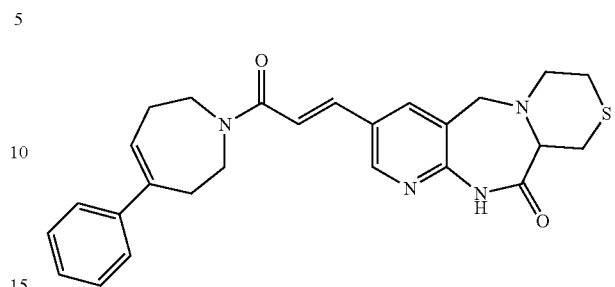

The compound Compound K1 was prepared starting from 1H-Azepine 2,3,6,7-tetrahydro-4-phenyl CAS [324784-75-95-4] (Intermediate A3) and Intermediate J8. Yielding: Compound K1, 0.160 g, (66%). m.p. 224° C.
$^1$H NMR (500 MHz, DMSO-d$_6$) δ 10.55 (br. s., 1H), 8.59-8.62 (m, 1H), 8.12-8.19 (m, 1H), 7.50-7.56 (m, 1H), 7.27-7.37 (m, 5H), 7.19-7.26 (m, 1H), 5.99-6.06 (m, 1H), 3.58-4.00 (m, 6H), 2.51-3.18 (m, 11H).

Example L

Preparation of Compounds in which $R^x$=(iii) and the $Z^2$-Containing Ring is 8-Membered

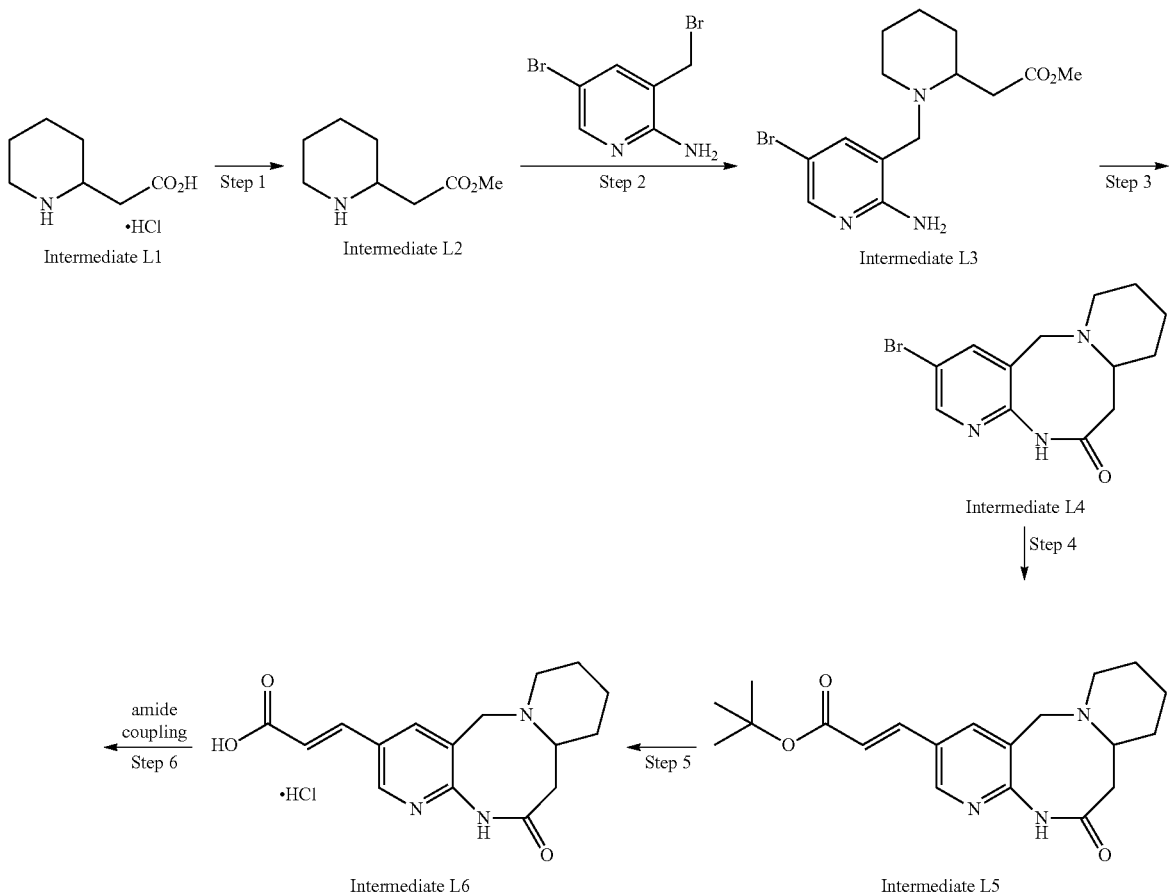

General: All experiments for the synthesis in the scheme above were carried out under argon atmosphere using anhydrous solvents.

Step 1: The preparation of Intermediate L2 was performed by reaction in the presence of Intermediate L1, SOCl$_2$ (e.g. 4 equivs) and MeOH (e.g. at reflux).

Step 2: Preparation of Intermediate L3

A mixture of Intermediate L2 (1.47 g, 9.35 mmol), the HBr salt of 3-bromo-5-bromomethyl-6-amino-pyridine (3.24 g, 9.35 mmol) and N-ethyldiisopropylamine (6.50 ml, 37.3 mmol) in acetonitrile (40 ml) was stirred at reflux for 3 h, then concentrated under reduced pressure. The residue was taken up in aqueous saturated sodium bicarbonate (70 ml) and extracted with dichloromethane (3×70 ml). The combined organic layers were washed with aqueous saturated sodium bicarbonate (2×100 ml), dried over sodium sulfate, filtered and then concentrated under reduced pressure. The crude compound was purified by column chromatography over silica gel (eluent: chloroform) and vacuum-dried to yield Intermediate L3 (2.67 g, 83%) as a yellowish oil.

Step 3: Preparation of Intermediate L4

Sodium hydride (60% dispersion in mineral oil, 0.437 g, 10.9 mmol) was added to a solution of Intermediate L3 (2.67 g, 7.80 mmol) in DMF (85 ml). The resulting mixture was stirred at room temperature for 3 h, then quenched by addition of water (10 ml) and concentrated under reduced pressure. The residue was taken up in water (80 ml) and extracted with dichloromethane/methanol (9/1, 5×80 ml). The combined organic layers were concentrated under reduced pressure. The residue was taken up in dichloromethane (100 ml), washed with saturated brine (5×80 ml), dried over sodium sulfate and concentrated under reduced pressure. The obtained product was triturated with diethyl ether (10 ml), collected by filtration on a glass frit, rinsed with diethyl ether (10 ml) and vacuum-dried to yield Intermediate L4 (1.25 g, 52%) as a yellowish solid.

Melting point: 216.1-225.6° C. under decomposition (Buchi M-560, 1° C./min).

Step 4: Preparation of Intermediate L5

Intermediate L4 (0.270 g, 0.870 mmol) was suspended in a mixture of DMF (3 ml) and acetonitrile (10 ml). Tert-butyl acrylate (0.510 ml, 3.48 mmol), N-ethyldiisopropylamine (0.320 ml, 1.84 mmol) and tri(o-tolyl)phosphine (0.0530 g, 0.174 mmol) were added. The resulting mixture was purged with argon and palladium acetate (0.0195 g, 0.0870 mmol) was added. The mixture was purged again with argon, stirred under reflux overnight and at room temperature for 2 days, then concentrated under reduced pressure. The residue was taken up in aqueous saturated sodium bicarbonate (20 ml) and extracted with dichloromethane (3×20 ml). The combined organic layers were dried over sodium sulfate, filtered and concentrated under reduced pressure. The crude residue was purified by column chromatography over silica gel (eluent: dichloromethane/methanol 98/2). The obtained product was taken up in dichloromethane (10 ml), washed with brine (3×20 ml), dried over sodium sulfate, filtered and concentrated under reduced pressure to yield Intermediate L5 (0.253 g, 81%) as a yellowish gum.

Step 5: Preparation of Intermediate L6:

A mixture of Intermediate L5 (0.253 g, 0.708 mmol) and 4M hydrogen chloride in 1,4-dioxane (7.00 ml, 28.0 mmol) was stirred at room temperature overnight and at 40° C. for 25 h. The precipitation was filtered on a glass frit, washed with dioxane (2×2 ml) and diethyl ether (3×2 ml) and dried under vacuum to yield Intermediate L6 (0.174 g, 67%) as a yellowish solid hydrochloride salt (1.8 eq. HCl according to chloride titration).

Step 6: Preparation of Final Compound:

An amide coupling reaction may be performed with the appropriate amine and the intermediate L6, using a coupling reagent such as 1-(3-dimethylaminopropyl)-3-ethylcarbodiimide hydrochloride and other reagents/reactants/solvents such as 1-hydroxybenzotriazole monohydrate, N-ethyldiisopropylamine and DMF/DMSO.

Example M

Synthesis of Intermediates in which X$^x$ Represents N

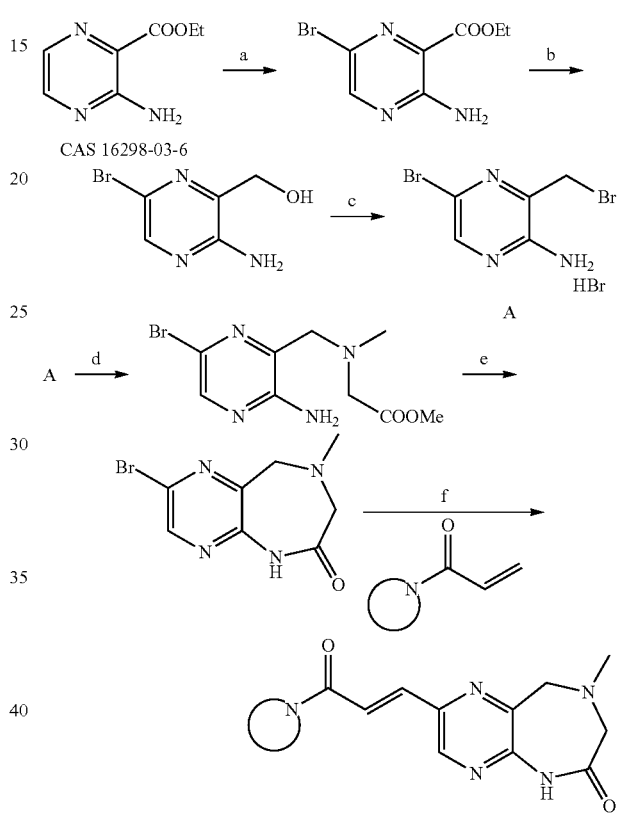

Conditions:
a) NBS, ACN, reflux, 3 h, 70%; b) LiAlH$_4$ 1 M in THF, THF, 5° C. to RT, o.n., 20%; c) PBr$_3$, DCM, RT, o.n., 90%; d) sarcosine ethyl ester, Et$_3$N, DMF, μw, 120° C., 20 min, 53%; e) NaH, DMF, RT, 3 h, 25%; f) DIEA, Pd(OAc)$_2$, tri-O-tolylphosphine, ACN, DMF, μw, 180° C., 25 min.

Hence, intermediate compounds (and therefore final compounds) in which the R$^x$ ring represents a monocyclic, bicyclic or tricyclic ring in which X$^x$ represents N may be prepared in accordance with the procedure described in this Example M.

The remaining compounds were prepared in accordance with the methods disclosed herein.

X. Compound Identification

X1. LCMS

For LCMS-characterization of the compounds of the present invention, the following methods were used.

General Procedure A

The LC measurement was performed using a UPLC (Ultra Performance Liquid Chromatography) Acquity (Waters) system comprising a binary pump with degasser, an autosampler, a diode-array detector (DAD) and a column as specified in the respective methods below, the column is hold at a temperature of 40° C. Flow from the column was brought to a MS detector. The MS detector was configured with an electrospray ionization source. The capillary needle voltage was 3 kV and the source temperature was maintained at 130° C. on the Quattro (triple quadrupole mass spectrometer from Waters). Nitrogen was used as the nebulizer gas. Data acquisition was performed with a Waters-Micromass MassLynx-Openlynx data system.

General Procedure B

The HPLC measurement was performed using an Alliance HT 2795 (Waters) system comprising a quaternary pump with degasser, an autosampler, a diode-array detector (DAD) and a column as specified in the respective methods below, the column is hold at a temperature of 30° C. Flow from the column was split to a MS spectrometer. The MS detector was configured with an electrospray ionization source. The capillary needle voltage was 3 kV and the source temperature was maintained at 100° C. on the LCT (Time of Flight Zspray™ mass spectrometer from Waters. Nitrogen was used as the nebulizer gas. Data acquisition was performed with a Waters-Micromass MassLynx-Openlynx data system.

Method 1

In addition to the general procedure A: reversed phase UPLC was carried out on a Waters Acquity BEH (bridged ethylsiloxane/silica hybrid) C18 column (1.7 μm, 2.1×100 mm) with a flow rate of 0.35 ml/min. Two mobile phases (mobile phase A: 95% 7 mM ammonium acetate/5% acetonitrile; mobile phase B: 100% acetonitrile) were employed to run a gradient condition from 90% A and 10% B (hold for 0.5 minutes) to 8% A and 92% B in 3.5 minutes, hold for 2 min and back to the initial conditions in 0.5 min, hold for 1.5 minutes. An injection volume of 2 μl was used. Cone voltage was 20 V for positive and negative ionization mode. Mass spectra were acquired by scanning from 100 to 1000 in 0.2 seconds using an interscan delay of 0.1 seconds.

Method 2

In addition to the general procedure A: reversed phase UPLC was carried out on a Waters Acquity BEH (bridged ethylsiloxane/silica hybrid) C18 column (1.7 μm, 2.1×100 mm) with a flow rate of 0.343 ml/min. Two mobile phases (mobile phase A: 95% 7 mM ammonium acetate/5% acetonitrile; mobile phase B: 100% acetonitrile) were employed to run a gradient condition from 84.2% A and 15.8% B (hold for 0.49 minutes) to 10.5% A and 89.5% B in 2.18 minutes, hold for 1.94 min and back to the initial conditions in 0.73 min, hold for 0.73 minutes. An injection volume of 2 μl was used. Cone voltage was 20V for positive and negative ionization mode. Mass spectra were acquired by scanning from 100 to 1000 in 0.2 seconds using an interscan delay of 0.1 seconds.

Method 3

In addition to the general procedure B: reversed phase HPLC was carried out on a Waters X-bridge C18 column (3.5 μm, 4.6×100 mm) with a flow rate of 0.8 ml/min. Two mobile phases (mobile phase A: 100% 7 mM ammonium acetate; mobile phase B: 100% acetonitrile) were employed to run a gradient condition from 80% A and 20% B (hold for 0.5 minute) to 90% B in 4.5 minutes, 90% B for 4 minutes and reequilibrated with initial conditions for 3 minutes. An injection volume of 5 μl was used. Cone voltage was 20 V for positive and negative ionization mode. Mass spectra were acquired from 100 to 1000 in 0.4 seconds using an interscan delay of 0.3 seconds.

Method 4

In addition to the general procedure B: reversed phase HPLC was carried out on a Waters Atlantis C18 column (5 μm, 3.9×100 mm) with a flow rate of 0.8 ml/min. Three mobile phases (mobile phase A: 100% 7 mM ammonium acetate; mobile phase B: 100% acetonitrile; mobile phase C: 0.2% formic acid+99.8% ultra-pure water) were employed to run a gradient condition from 50% A and 50% C (hold for 1.5 minute) to 10% A, 80% B and 10% C in 4.5 minutes, hold for 4 minutes and reequilibrated with initial conditions for 3 minutes. An injection volume of 5 μl was used. Cone voltage was 20 V for positive and negative ionization mode. Mass spectra were acquired by scanning from 100 to 1000 in 0.4 seconds using an interscan delay of 0.3 seconds.

Method 5

The HPLC measurement was performed using an HPLC 1100/1200 (Agilent) system comprising a quaternary pump with degasser, an autosampler, a diode-array detector (DAD) and a column as specified in the respective methods below, the column is hold at room temperature. The MS detector (MS-Agilent simple quadripole) was configured with an electrospray-APCI ionization source. Nitrogen was used as the nebulizer gas. Data acquisition was performed with a Chem-station data system.

Reversed phase HPLC was carried out on a Nucleosil C18 column (3 μm, 3×150 mm) with a flow rate of 0.42 ml/min. Two mobile phases (mobile phase A: water/TFA (0.1%); mobile phase B: 100% acetonitrile) were employed to run a gradient condition from 98% A for 3 minutes, to 100% B in 12 minutes, 100% B for 5 minutes, then back to 98% A in 2 minutes, and reequilibrated with 98% A for 6 minutes. An injection volume of 2 μl was used. The capillary voltage was 2 kV, the corona discharge was held at 1 μA and the source temperature was maintained at 250° C. A variable voltage was used for the fragmentor. Mass spectra were acquired in electrospray ionization and APCI in positive mode, by scanning from 100 to 1100 amu.

Method 6

This method employs the following parameters:
Agilent 1200 LC 6100 MS
Column: HALO C18(4.6*50 mm 2.7 μm)
Flow: 1.8 ml/min
A: H2O (0.05% FA) B: CH3CN (0.05% FA)

| Time (min) | Conc: (B %) |
| --- | --- |
| 0 | 5 |
| 1 | 95 |
| 2 | 95 |
| 2.01 | 5 |
| 2.5 | 5 |

X2. Melting Points

For a number of compounds, melting points were obtained with a Kofler hot bench, consisting of a heated plate with linear temperature gradient, a sliding pointer and a temperature scale in degrees Celsius.

For a number of compounds, melting points were determined using differential scanning calorimetry (DSC). Melting points were measured with a temperature gradient of 10° C./minute starting at 25° C. Maximum temperature was 350° C.

For a number of compounds, melting points were obtained with a Büchi melting point apparatus B-560. The heating medium was a metal block. The melting of the sample was visually observed by a magnifying lense and a big light contrast. Melting points were measured with a temperature gradient of either 3 or 10° C./minute. Maximum temperature was 300° C.

The remaining melting points were determined using open capillary tubes.

TABLE X

LC/MS data and melting points
For Compounds in which $R^x$ is ring (i)

| Cpd. No. | Rt | MH+ | LCMS Method | Melting Point (method) |
|---|---|---|---|---|
| 1 | 2.74 | 425 | 2 | 186° C. (Kofler) |
| 2 | 2.96 | 414 | 2 | 156° C. (Kofler) |
| 3 | 2.84 | 473 | 2 | 122° C. (Kofler) |
| 4 | 2.89 | 428 | 2 | |
| 5 | 2.95 | 487 | 2 | 120° C. (Kofler) |
| 6 | 2.68 | 362 | 2 | 152° C. (Kofler) |
| 7 | 2.62 | 348 | 2 | |
| 8 | 3.2 | 428 | 2 | 192° C. (Kofler) |
| 9 | 3.21 | 424 | 2 | 158.31° C./−70.01 Jg-1 (DSC) |
| 10 | 2.87 | 428 | 2 | 138° C. (Kofler) |
| 11 | 2.61 | 414 | 2 | 120° C. (Kofler) |
| 12 | 3.31 | 362 | 1 | 188° C. (Kofler) |
| 13 | 2.8 | 425 | 2 | 98° C. (Kofler) |
| 14 | 3.24 | 396 | 2 | 150° C. (Kofler) |
| 15 | 3.07 | 402 | 2 | |
| 16 | 3.1 | 429 | 2 | 169.37° C./−114.76 Jg-1 (DSC) |
| 17 | 2.73 | 428 | 2 | 134° C. (Kofler) |
| 18 | 3.18 | 416 | 2 | 141° C. (Kofler) |
| 19 | 2.97 | 390 | 2 | 158° C. (Kofler) |
| 20 | 2.73 | 418 | 2 | 152° C. (Kofler) |
| 21 | 3.19 | 320 | 1 | 184° C. (Kofler) |
| 22 | 3.04 | 416 | 2 | 159° C. (Kofler) |
| 23 | 2.53 | 320 | 2 | |

Table of compounds in which $R^x$ is (ii) i.e. a bicycle

| Cpd. No. | Rt | MH+ | LCMS Method | Melting Point (method) |
|---|---|---|---|---|
| 31 | 2.49 | 437 | 2 | 192° C. (Kofler) |
| 32 | 2.74 | 438 | 2 | 234° C. (Kofler) |
| 33 | 1.26 | 409 | 6 | 125-126° C. (X-4B) |
| 34 | 2.43 | 389 | 2 | 203.18° C./−3.49 Jg-1 (DSC) |
| 35 | 2.66 | 424 | 2 | 218.22° C./−48.79 Jg-1 (DSC) |
| 36 | 2.43 | 389 | 2 | 203.18° C./−3.49 Jg-1 (DSC) |
| 37 | 2.6 | 467 | 2 | |
| 38 | 2.52 | 403 | 2 | 198.79° C./−61.26 J/g (DSC) |
| 39 | 2.46 | 431 | 2 | |
| 40 | 2.52 | 403 | 2 | 198.79° C./−61.26 J/g (DSC) |
| 41 | 2.61 | 376 | 2 | 244.33° C. /−80.8 J/g (DSC) |
| 42 | 2.99 | 465 | 2 | |
| 43 | 1.25 | 409 | 6 | 212-213° C. (X-4B) |
| 44 | 3.02 | 509 | 2 | 198° C. (Kofler) |

Table of compounds in which $R^x$ is (iii) i.e. a tricycle

| Cpd. No. | Rt | MH+ | LCMS Method | Melting Point (method) |
|---|---|---|---|---|
| 46 | 2.53 | 445 | 2 | 227.76° C./−46.4 J/g (DSC) |
| 47 | 2.4 | 486 | 2 | 208° C. (Kofler) |
| 48 | 13.62 | 534 | 5 | |
| 49 | 2.76 | 461 | 2 | 224.06° C./−60.35 J/g (DSC) |
| 50 | 2.52 | 445 | 2 | 220° C. (Kofler) |
| 51 | 2.73 | 461 | 2 | 224° C. (Kofler) |
| 52 | 2.24 | 444 | 2 | 206° C. (Kofler) |

Y. Pharmacological Examples

Y.1 FabI Enzyme Inhibition: *Staphylococcus aureus* FabI Enzyme Inhibition Assay FabI enzyme inhibition assays were carried out in half-area, 384-well microtitre plates. Compounds were evaluated in 40 μl assay mixtures containing 100 mM NaADA, pH 6.5 (ADA=N-[2-acetamido]-2iminodiacetic acid), 250 μM crotonoyl-CoA, 625 μM NADH and 50 μg/ml *S. aureus* ATCC 29213 FabI Inhibitors were typically varied over the range of 50 to 0.39 μM. The reaction mixtures were incubated for 30 minutes at room temperature and the reaction was stopped by adding 200 mM Tris buffer (pH 9.0) to create a pH-shift. The consumption of NADH was monitored by measuring the change in absorbance at 340. By comparing sample readings to those of negative (absence of compound) and positive (absence of enzyme) controls, the percent inhibition of enzymatic activity of the compounds was determined A best-fit curve is fitted by a minimum of squares method. From this an $IC_{50}$-value (expressed in μg/ml), resulting in 50% inhibition of enzymatic activity, was obtained.

The results are depicted in the table(s) below (FabI activity).

Y.2 In Vitro Method for Testing Compounds for Antibacterial Activity Against Various Bacterial Strains Preparation of Bacterial Suspensions for Susceptibility Testing The following bacteria were used: *Staphylococcus aureus* ATCC 29213, methicillin-resistant *Staphylococcus aureus* (MRSA) ATCC 700788 and *Escherichia coli* ATCC 35218. The bacteria used in this study were grown overnight in flasks containing 100 ml Mueller-Hinton broth (Difco cat. nr. 0757-17) in sterile de-ionized water, with shaking, at 37° C. Stocks were store at −70° C. until use.

Bacteria were incubated on a tryptic soy agar plate containing 5% sheep blood (Becton Dickinson cat. nr. 254053) for 18-24 hours at 35° C. in aerobic conditions (first passage). For the second passage, fresh Mueller-Hinton broth is inoculated with 5-10 colonies and grown overnight at 35° C. until turbidity (reaching log-phase) in aerobic conditions is reached. The bacterial suspension is then adjusted to 0.5 McFarland density and further diluted 1:100 in Mueller Hinton broth medium. This is used as inoculum.

The result(s) are depicted the table below (for STA ATCC 29213).

Antibacterial Susceptibility Testing: $IC_{90}$ Determination

MIC assays were performed by the broth microdilution method in a 96-well format (flat-bottom microtitre plates) with a final volume of 0.1 ml Mueller Hinton broth containing two-fold serial dilutions of compounds and inoculated with $5 \times 10^5$ CFU/ml of bacteria (standard inoculum size according to CLSI guidelines). Inhibitors are typically varied over the range of 63 to 0.49 μM. The final DMSO concentration in the assay was 1.25% (maximum tolerable DMSO concentration=6%). In the assays where the effect of human serum on the activity of the compounds against *S. aureus* was tested, human serum was added at a final concentration of 10%. The plates were incubated at 35° C. for 16-20 hours. At the end of incubation the bacterial growth was quantified fluorometrically. For this, resazurin was added to all wells and the plates were re-incubated. The incubation time is dependent on the type of bacteria. A change in color from blue to pink indicated the growth of bacteria. The fluorescence was read in computer-controlled fluorometer (Fluoroskan Ascent FL, Lab-systems) at an excitation wavelength 540 nm and an emission wavelength of 590 nm. The % growth inhibition achieved by the compounds was calculated according to standard methods. The $IC_{90}$ (expressed in μg/ml) was defined as the 90% inhibitory concentration for bacterial growth. A panel of reference compounds were simultaneously tested for QC approval.

The results are depicted in the table(s) below (STA+10% HS).

Cytotoxicity Assays

Cytotoxicity of the compounds was evaluated using the MTT assay. Human HelaM cells grown in 96-well plates were exposed to serial dilutions of the tested compounds (final volume of 0.2 ml) and incubated for 72 hours at 37° C. and 5% $CO_2$ Inhibitors are typically varied over the range of 25 to 0.8 μM. The final DMSO concentration in the assay is 0.5%. MTT (3-(4,5-Dimethylthiazol-2-yl)-2,5-diphenyltetrazolium bromide, a tetrazole) was added and reduced to purple formazan only in living cells. Solubilization of the formazan crystals was achieved by adding 100 μl 2-propanol. Cell viability was determined by measuring the absorbance of the reduced formazan, giving a purple color, at 540 nm and 690 nm. The absorbance measured at 690 nm was automatically subtracted from the absorbance at 540 nm, to eliminate the effects of non-specific absorption. The percent cytotoxicity achieved by the compounds was calculated according to standard methods. Cytotoxicity is reported as $CC_{50}$, the concentration that causes a 50% reduction in cell viability.

The results are depicted in the table(s) below (HELAM).

Biological Testing

Compounds of the invention/examples were tested in assays described above and were found to exhibit a certain inhibition as depicted in the tables below.

TABLE of compounds in which $R^x$ is (i) i.e. a monocycle

| Example | Cpd. No. | STA (361.159) IC90 μg/mL | STA + 10% HS (361.169) IC90 μg/mL | HELAM (222.125) CC50 μg/mL | FabI (300.235) IC50 μg/mL |
|---|---|---|---|---|---|
| <structure> | 1 | 0.40 | 0.84 | 0.43 | 0.31 |
| <structure> | 2 | 0.44 | 1.43 | >10.39 | 0.49 |
| <structure> | 3 | 0.45 | 1.68 | 1.13 | 0.77 |
| <structure> | 4 | 0.63 | 1.66 | 3.94 | 0.60 |

TABLE-continued of compounds in which R^x is (i) i.e. a monocycle

| Example | Cpd. No. | STA (361.159) IC90 μg/mL | STA + 10% HS (361.169) IC90 μg/mL | HELAM (222.125) CC50 μg/mL | FabI (300.235) IC50 μg/mL |
|---|---|---|---|---|---|
| | 5 | 0.66 | 2.83 | 7.80 | 0.87 |
| | 6 | 0.69 | 1.90 | >9.08 | ~0.29 |
| | 7 | 0.78 | 1.25 | 7.18 | 0.23 |
| | 8 | 0.84 | 6.70 | 5.64 | 0.91 |
| | 9 | 0.85 | 6.26 | 4.24 | 0.77 |

TABLE-continued
of compounds in which R^x is (i) i.e. a monocycle
| Example | Cpd. No. | STA (361.159) IC90 μg/mL | STA + 10% HS (361.169) IC90 μg/mL | HELAM (222.125) CC50 μg/mL | FabI (300.235) IC50 μg/mL |
|---|---|---|---|---|---|
| 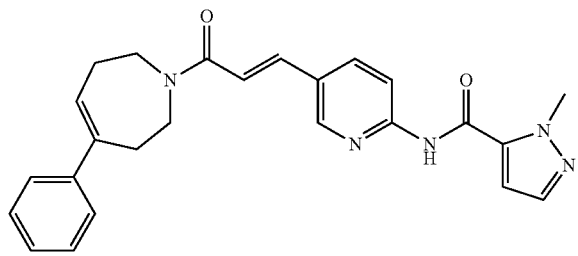 [SMILES: Cn1nccc1C(=O)Nc1ccc(/C=C/C(=O)N2CCC=C(c3ccccc3)CC2)cn1] | 10 | 0.92 | 2.07 | 5.44 | 0.82 |
| 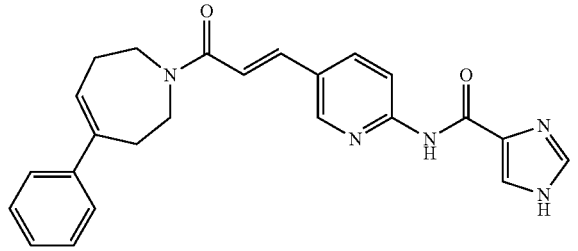 [SMILES: O=C(Nc1ccc(/C=C/C(=O)N2CCC=C(c3ccccc3)CC2)cn1)c1c[nH]cn1] | 11 | 1.26 | 3.17 | >10.39 | 0.67 |
| 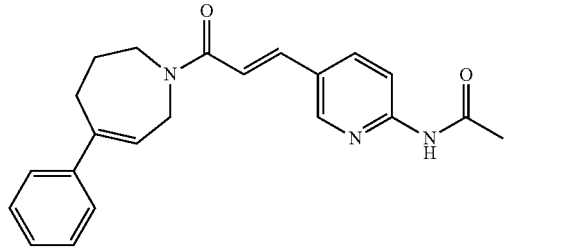 [SMILES: CC(=O)Nc1ccc(/C=C/C(=O)N2CC=C(c3ccccc3)CCC2)cn1] | 12 | 1.30 | 1.90 | >9.08 | 0.22 |
| 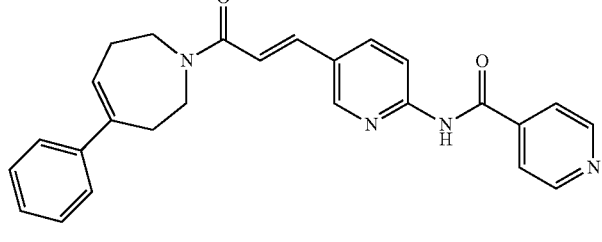 | 13 | 1.41 | 3.08 | 4.29 | 0.53 |
| 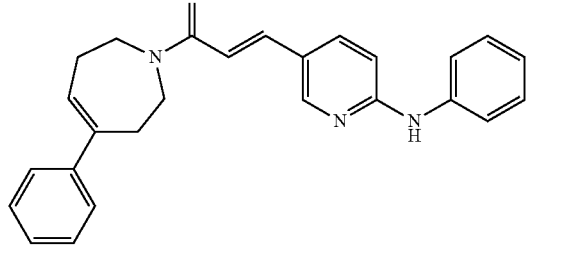 | 14 | 1.45 | 24.11 | 6.27 | 0.89 |

TABLE-continued of compounds in which R^x is (i) i.e. a monocycle

| Example | Cpd. No. | STA (361.159) IC90 μg/mL | STA + 10% HS (361.169) IC90 μg/mL | HELAM (222.125) CC50 μg/mL | FabI (300.235) IC50 μg/mL |
|---|---|---|---|---|---|
| (structure) | 15 | 2.84 | 11.85 | 6.59 | ~0.43 |
| (structure) | 16 | 3.29 | 6.71 | 7.89 | 0.66 |
| (structure) | 17 | 4.29 | 8.56 | 13.88 | 1.03 |
| (structure) | 18 | 6.29 | >26.22 | 2.62 | 0.85 |
| (structure) | 19 | 6.32 | 20.92 | 8.52 | 0.50 |

TABLE-continued of compounds in which R^x is (i) i.e. a monocycle

| Example | Cpd. No. | STA (361.159) IC90 μg/mL | STA + 10% HS (361.169) IC90 μg/mL | HELAM (222.125) CC50 μg/mL | FabI (300.235) IC50 μg/mL |
|---|---|---|---|---|---|
| (structure) | 20 | 6.69 | 11.77 | 10.02 | 0.39 |
| (structure) | 21 | 6.75 | 12.86 | 4.78 | 1.24 |
| (structure) | 22 | 11.57 | 12.12 | 8.01 | 0.45 |
| (structure) | 23 | 13.32 | >20.15 | 5.30 | 0.96 |
| (structure) | 24 | 21.04 | >22.8085 | >9.08022 | 1.90 |

TABLE-continued of compounds in which R^x is (i) i.e. a monocycle

| Example | Cpd. No. | STA (361.159) IC90 μg/mL | STA + 10% HS (361.169) IC90 μg/mL | HELAM (222.125) CC50 μg/mL | FabI (300.235) IC50 μg/mL |
| --- | --- | --- | --- | --- | --- |
| | 25 | >25.461 | >25.461 | 6.32 | 0.82 |
| | 26 | >25.461 | >25.461 | 3.77 | 0.56 |
| | 27 | >26.7848 | >26.7848 | 3.83 | 0.89 |
| | 28 | >26.8466 | 26.24 | >10.6878 | 0.51 |
| | 29 | >27.104 | >27.104 | 3.15 | 1.33 |

TABLE-continued
of compounds in which R^x is (i) i.e. a monocycle
| Example | Cpd. No. | STA (361.159) IC90 µg/mL | STA + 10% HS (361.169) IC90 µg/mL | HELAM (222.125) CC50 µg/mL | FabI (300.235) IC50 µg/mL |
|---|---|---|---|---|---|
| 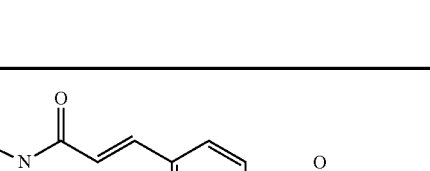 | 30 | 27.68 | 33.28 | 11.02 | ~0.736545 |
TABLE
of compounds in which R^x is (ii) i.e. a bicycle
| Example | Cpd. No. | STA (361.159) IC90 µg/mL | STA + 10% HS (361.169) IC90 µg/mL | HELAM (222.125) CC50 µg/mL | FabI (300.235) IC50 µg/mL |
|---|---|---|---|---|---|
| 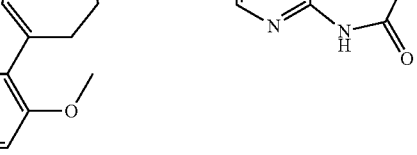 | 31 | <0.21 | 0.26 | >10.96 | ~0.407356 |
| 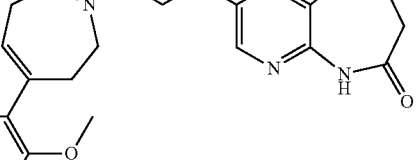 | 32 | 0.22 | 0.41 | 10.14 | 0.55 |
| 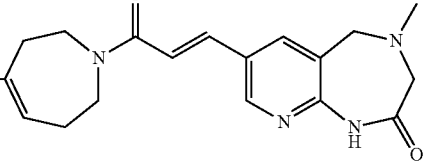 | 33 | 0.32 | 0.26 | >10.26 | 0.51 |

TABLE-continued of compounds in which R^x is (ii) i.e. a bicycle

| Example | Cpd. No. | STA (361.159) IC90 μg/mL | STA + 10% HS (361.169) IC90 μg/mL | HELAM (222.125) CC50 μg/mL | FabI (300.235) IC50 μg/mL |
|---|---|---|---|---|---|
| | 34 | 0.37 | 0.38 | >9.76 | 0.35 |
| | 35 | 0.38 | 0.54 | 6.56 | ~0.43 |
| | 36 | 0.46 | 0.45 | >19.47 | 0.29 |
| | 37 | 0.48 | 0.66 | 2.04 | 0.32 |
| | 38 | 0.50 | 0.46 | >10.11 | 0.33 |

TABLE-continued of compounds in which R^x is (ii) i.e. a bicycle

| Example | Cpd. No. | STA (361.159) IC90 μg/mL | STA + 10% HS (361.169) IC90 μg/mL | HELAM (222.125) CC50 μg/mL | FabI (300.235) IC50 μg/mL |
|---|---|---|---|---|---|
| (structure) | 39 | 0.51 | 0.75 | >10.81 | 0.32 |
| (structure) | 40 | 0.53 | 0.60 | 24.25 | 0.29 |
| (structure) | 41 | 0.60 | 0.67 | >9.43 | 0.37 |
| (structure) | 42 | 0.77 | 3.33 | 11.67 | ~0.70 |
| (structure) | 43 | 1.13 | 1.32 | >10.26 | 1.07 |

TABLE-continued of compounds in which R^x is (ii) i.e. a bicycle

| Example | Cpd. No. | STA (361.159) IC90 μg/mL | STA + 10% HS (361.169) IC90 μg/mL | HELAM (222.125) CC50 μg/mL | FabI (300.235) IC50 μg/mL |
|---|---|---|---|---|---|
| [structure] | 44 | 4.80 | 3.64 | >12.78 | ~1.43 |
| [structure] | 45 | >34.41 | >34.41 | >13.70 | 0.57 |

TABLE of compounds in which R^x is (iii) i.e. a tricycle

| Example | Cpd. No. | STA (361.159) IC90 μg/mL | STA + 10% HS (361.169) IC90 μg/mL | HELAM (222.125) CC50 μg/mL | FabI (300.235) IC50 μg/mL |
|---|---|---|---|---|---|
| [structure] | 46 | <0.22 | 0.53 | >11.17 | 0.25 |
| [structure] | 47 | 0.25 | 0.44 | 17.63 | 0.38 |

TABLE-continued of compounds in which R^x is (iii) i.e. a tricycle

| Example | Cpd. No. | STA (361.159) IC90 μg/mL | STA + 10% HS (361.169) IC90 μg/mL | HELAM (222.125) CC50 μg/mL | FabI (300.235) IC50 μg/mL |
|---|---|---|---|---|---|
| (structure) | 48 | <0.26 | 0.46 | >13.40 | 0.59 |
| (structure) | 49 | 0.39 | 1.23 | 4.88 | 0.51 |
| (structure) | 50 | 0.64 | 1.58 | 22.02 | 0.31 |
| (structure) | 51 | 0.67 | 1.60 | 5.35 | 0.51 |
| (structure) | 52 | 6.56 | 4.75 | >11.14 | 9.48 |

Example Z

Z.1 Thermodynamic Solubility

The pH solubility profiling is carried out at ambient temperature for a period of 4 days. A saturation solubility study is carried out in order to determine maximum solubility in a particular buffer solution. The compound is added to respective buffer solution until saturation point is reached. This is followed by shaking the flask for 4 days at ambient temperature. After 4 days, the solutions are filtered and injected on UPLC and the concentration is determined using a generic HPLC method.

Results

Compounds of the invention/examples are found to display good thermodynamic solubility, for instance the compounds may display good concentrations when the following buffer solutions are employed in the above test: Buffer pH 2, 10% HP-3-CD buffer pH 2, 20% HP-β-CD buffer pH 2, Buffer pH 4, 10% HP-β-CD buffer pH 4, 20% HP-β-CD buffer pH 4, Buffer pH 7.4, 10% HP-β-CD buffer pH 7.4 and 20% HP-β-CD buffer pH 7.4.

Z.2 Antimicrobial Spectrum of Activity

Minimum Inhibitory Concentrations (MICs) are determined in accordance with the Clinical and Laboratory Standards Institute (CLSI) methodology against aerobic bacteria (CLSI M07-A8) (see Clinical and Laboratory Standards Institute. 2009. Methods for dilution antimicrobial susceptibility tests for bacteria that grow aerobically. CLSI document M07-A8, Vol. 29, No. 2.) by the broth microdilution method with cation-adjusted Mueller-Hinton broth (CA-MHB) medium for the majority of organisms, except for *Haemophilus influenza*, where Haemophilis test medium (HTM) broth is used. Descriptions of the individual organisms can be found in the table. Where possible, ATCC standard strains are tested.

The inoculum density for the susceptibility testing is standardized to give a final inoculum of approximately $5 \times 10^5$ CFU/mL. The broth MIC is determined as the lowest concentration of drug that prevented visible growth after 16-24 hours (species dependent) of incubation at 35° C.-37° C.

TABLE

Description of individual organisms tested

| Organism | Characteristics | MIC test medium |
|---|---|---|
| Staphylococcus aureus | ATCC 29213; reference strain MSSA | MHB |
| Staphylococcus aureus | ATCC 43300; reference strain MRSA | MHB |
| Staphylococcus aureus | NRS119; LZD-R; SCCmec IV; origin: US | MHB |
| Staphylococcus aureus | NRS120; LZD-R; SCCmec IV; origin: US | MHB |
| Staphylococcus aureus | NRS121; LZD-R; SCCmec IV; origin: US | MHB |
| Escherichia coli | ATCC 25922; reference strain | MHB |
| Escherichia coli | Tol C mutant | MHB |
| Haemophilus influenzae | ATCC 49247; reference strain | HTM broth |
| Moraxella catarrhalis | ATCC 8176; b-lactamase negative | MHB |

Stock solutions of the compounds are prepared in DMSO at concentrations of 1 mg/mL. Linezolid is prepared in DMSO at a concentration of 2 mg/mL. Stock solutions of all compounds are diluted into CA-MHB to give a range of two-fold dilutions, depending upon the sensitivity of the organism being tested.

Results

Compounds of the invention/examples are found to exhibit a broader spectrum of antibacterial activity, for instance compounds may be found to be active against a number of bacterial strains e.g. *S. aureus* ATCC 29213, *S. aureus* NRS119, *S. aureus* NRS120, *S. aureus* NRS121, *E. coli* tolC mutant, *E. coli* ATCC 25922, *H. influenza* ATCC 49247, *M. catarrhalis* ATCC 8176.

E.3 In Vivo Pharmacokinetic and Oral Bioavailability

The in vivo pharmacokinetics and oral bioavailability of the compound of the examples were/are investigated in male Swiss mice (fed) following single intravenous (i.v.) bolus and oral (p.o.) administration. For the i.v. and p.o. solution formulations, the compound was/is dissolved in a 20% HP-β-CD solution. The pH of the formulations was/is around pH 4. All i.v. formulations were isotonic.

Results

Compounds of the invention/examples are found to exhibit good in vivo pharmacokinetic and/or oral bioavailability properties, for instance compounds may be found to exhibit good properties as measured by pharmacokinetic parameters such as, for i.v. forms, plasma clearance CI, $VD_z$, AUC and half life, and, for p.o. forms, $C_{max}$, $T_{max}$, AUC, half life and oral bioavailability %.

E.4 In Vivo Efficacy

The concept of studying the in vivo effect of an antibacterial compound by treating intraperitoneally infected mice was introduced in 1911 for optochin against pneumococci (Morgenroth and Levy, 1911). The popularity of the model comes from the ease of its use with short-duration experiments, reproducible infections and simple end-points.

Method Methicillin-sensitive *S. aureus* strain ATCC 29213 is used to infect female Swiss albino mice. A Brain Heart Infusion (BHI) broth bacterial culture is inoculated the day before infection, incubated at 37° C. overnight and diluted in fresh BHI broth to the desired concentration. Intraperitoneal (i.p.) injection of $-5 \times 10^9$ colony forming units (CFU) is performed in either of the lateral lower quadrants of the abdomen. After inoculation, mice are kept in their cages under daily observation for development of signs of infection or death. For the treatment of mice, both the p.o. and i.v. routes may be used and each mouse is treated individually by gavage or by i.v. injection. Both solutions and suspensions are tested in this model. The parameter used for monitoring the course of infection and the effect of treatment is death or survival of the animals over 3 days post-infection. As death could also be due to toxic side effects, a non-infected control group of 3 mice, treated with the highest dose of the compound tested, is included.

Results

Compounds of the invention/examples display good in vivo efficacy properties, for instance compounds may exhibit such properties as measured by % survival (following the above test).

The invention claimed is:

1. A compound of formula (I)

wherein
M is a moiety of formula

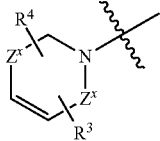

each $Z^x$ independently is —[C($R^{z8}$)($R^{z9}$)]$_n$—, in which n is 1 or 2;
$R^{z8}$ and $R^{z9}$ independently are hydrogen, $R^3$ or $R^4$;
$R^1$ is hydrogen, $C_{1-4}$alkyl or halo;
$R^2$ is hydrogen, $C_{1-4}$alkyl or halo;
$R^x$ is selected from the group consisting of moieties of formulae (i), (ii) and (iii), (i)

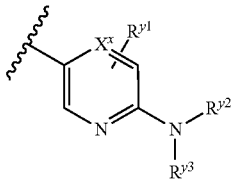

wherein
$X^x$ represents C(H), C($R^{yy}$) or N;
$R^{yy}$ is selected from the group consisting of hydrogen, halo, —CN, A1 and B1; wherein each of said A1 and B1 is optionally and independently substituted by one or more fluoro atoms, and said A1 is —O—$C_{1-6}$ alkyl, and said B1 is $C_{1-6}$ alkyl;
$R^{y1}$ is one to three optional substituents each independently selected from hydrogen, halo, —CN, A1 or B1;
each $R^{y2}$ and $R^{y3}$ independently is hydrogen or -$Q^1$-$R^5$;
each $Q^1$ independently is a direct bond or —C(O)—;
each $R^5$ is hydrogen, A2, B2, A3 or B3 wherein each of said A2 and B2 is optionally and independently substituted by at least one of =O and $Q^2$, said A2 is $C_{1-6}$ alkyl, said B2 is heterocycloalkyl, and wherein each of said A3 and B3 is optionally and independently substituted by at least one of $Q^3$ substituents, said A3 is aryl and said B3 is heteroaryl;
$Q^2$ is selected from the group consisting of halo, —CN, A4, B4 and B5, wherein said A4 is optionally substituted by at least one fluoro, and said A4 is —O$C_{1-6}$ alkyl, and each of said B4 and B5 are optionally and independently substituted by one or more substituents selected from halo, —CN, optionally fluoro-substituted $C_{1-3}$ alkyl and optionally fluoro-substituted —O$C_{1-3}$ alkyl, and said B4 is aryl, and said B5 is heteroaryl;
$Q^3$ is selected from the group consisting of halo, —CN, A5 and B6; wherein each of said A5 and B6 is optionally and independently substituted by at least on fluoro said and A5 is —O—$C_{1-6}$ alkyl and said B6 is $C_{1-6}$ alkyl;

(ii)

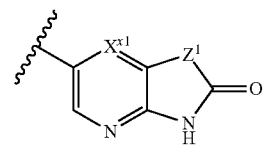

wherein
$X^{x1}$ is C(H) or N;
$Z^1$ is —$X^1$—O—$X^{1a}$—, —$X^2$—N($R^{z3}$)—$X^{2a}$— or —$X^3$—S—$X^{3a}$—;
each of $X^1$, $X^2$ and $X^3$ independently is a direct bond, —C(O)—, or —C($R^{z4}$)($R^{z5}$)—;
each of $X^{1a}$, $X^{2a}$ and $X^{3a}$ independently is a direct bond or —$V^1$—C($R^{z1}$)($R^{z2}$)—;
$V^1$ is a direct bond or —C(O)—;
each of $R^{z1}$, $R^{z2}$, $R^{z3}$, $R^{z4}$ and $R^{z5}$ independently is selected from the group consisting of hydrogen, A6 and B7, wherein said A6 is optionally substituted by at least one of =O and halo, said A6 is $C_{1-6}$ alkyl, said B7 is (optionally substituted by at least one of =O, halo and $C_{1-3}$ alkyl, and said B7 is heterocycloalkyl;
and (iii)

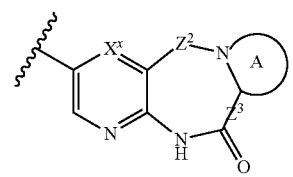

wherein
$X^x$ is C(H) or N;
$Z^2$ is —C($R^{z6}$)($R^{z7}$)— or —C(O)—;
$Z^3$ is —CH$_2$— and moiety (iii) is moiety (iii.1)

(iii.1)

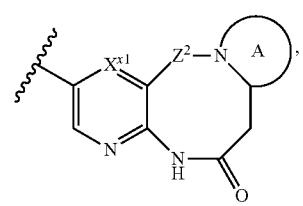

or a bond and moiety (iii) is moiety (iii.2)

(iii.2)

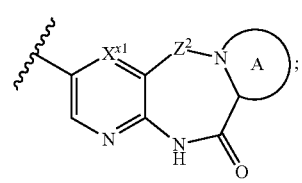

A is a 5- or 6-membered ring optionally containing one, two or three double bonds and optionally containing an additional one to three heteroatoms, wherein each of said heteroatoms is N or O, wherein said A is optionally substituted by one or more substituents each independently selected from =O and $R^{z8}$;

each $R^{z6}$, $R^{z7}$ and $R^{z8}$ independently is hydrogen or A7, wherein said A7 is optionally substituted by at least one substituent selected from =O, —$OC_{1-4}$ alkyl and halo, and said A7 is $C_{1-6}$ alkyl;

each $R^3$ independently is hydrogen, halo, —$OR^{10}$ or A8, wherein said A8 is optionally substituted by at least one halo and said A8 is $C_{1-6}$ alkyl;

each $R^4$ independently is hydrogen, halo or -$T^1$-$R^{20}$;

wherein each $T^1$ independently is a bond, —O—, —C(O)—, —C(O)—O—, —O—C(O)—, —C(O)—N($R^{21}$)— or —S(O)$_{n1}$— wherein n1 is 0, 1 or 2, and $R^{21}$ is hydrogen or $C_{1-6}$ alkyl;

each $R^{10}$ and each $R^{20}$ independently is A9, B8 or B9, wherein said A9 is optionally and independently substituted by at least one substituent selected from the group consisting of =O and $Y^1$, and said A9 is $C_{1-6}$ alkyl, each of said B8 and B9 is optionally substituted by one or more substituents independently selected from $Y^2$ said B8 is aryl and said B9 is heteroaryl;

each $Y^1$ independently is halo, —O—$R^{30}$, —CN, B10 or B11 wherein each of said B10 and B11 is optionally substituted by at least one substituent selected from the group consisting of halo, —O—$C_{1-3}$alkyl and $C_{1-3}$ alkyl and said B10 is aryl and said B11 is heteroaryl;

each $Y^2$ independently this halo, A10 or A11; wherein each of said A10 and A11 is optionally substituted by at least one fluoro, said A10 is —$OC_{1-6}$alkyl, and said A11 is $C_{1-6}$ alkyl;

each $R^{30}$ independently is hydrogen, A12, B12 or B13, wherein said A12 is optionally substituted by at least one fluoro, said A12 is $C_{1-6}$ alkyl, each of said B12 and B13 is independently and optionally substituted by at least one substitutent selected from the group consisting of halo, —O—$C_{1-3}$alkyl and $C_{1-3}$ alkyl, said B12 is aryl, and said B13 is heteroaryl;

or a pharmaceutically acceptable salt thereof.

2. The compound as claimed in claim 1 wherein moiety M is selected from the group consisting of:

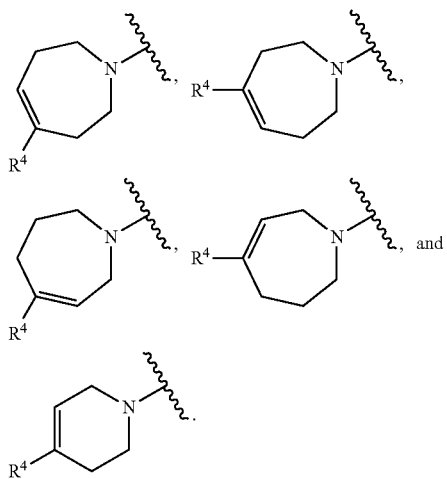

3. The compound as claimed in claim 1 wherein $R^4$ is one of the following optionally substituted groups:

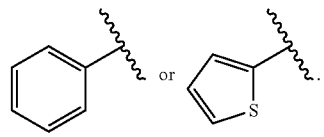 [SMILES: *c1ccccc1 ; *c1cccs1]

4. The compound as claimed in claim 1 wherein each of $R^{y1}$ and $R^{yy}$ is hydrogen and the other $R^{y2}$ is -Q1-$R^5$.

5. The compound as claimed in claim 1 wherein $Q^1$ is —C(O)—, and $R^5$ is selected from the group consisting of:

H, $CH_3$, $CF_3$, isopropyl, tert-butyl, isobutyl, cyclopentyl, -cyclopropylmethyl, cyclohexyl,

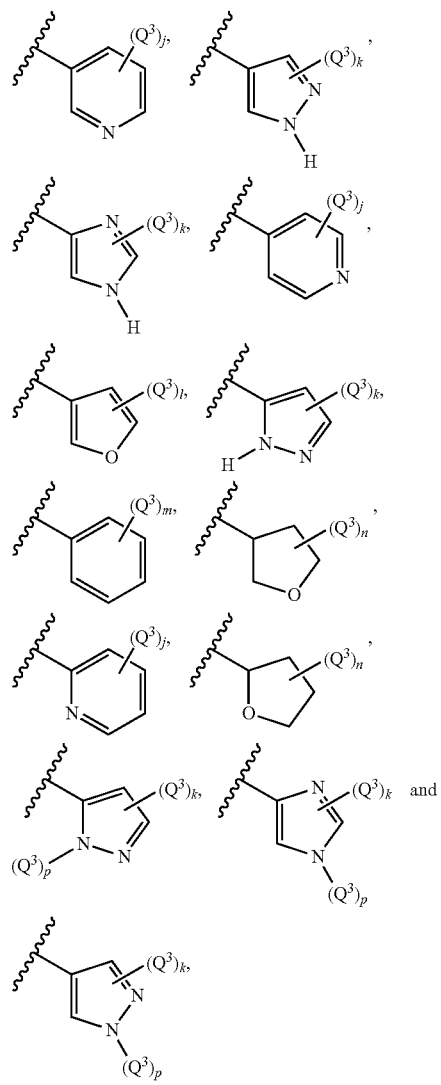

wherein
j is 0, 1, 2, 3 or 4;
k is 0, 1 or 2;
l is 0, 1, 2, 3;
m is 0, 1, 2, 3, 4 or 5;

n is 0, 1, 2, 3, 4, 5, 6 or 7;

p is 1;

and wherein each of $(Q^3)_j$, $(Q^3)_k$, $(Q^3)_l$, $(Q^3)_m$, $(Q^3)_n$ and $(Q^3)_p$ is independently selected from any other $Q^3$ assignment.

6. The compound as claimed in claim 1 wherein when $R^x$ is moiety (ii), and said $R^x$ is selected from the group consisting of:

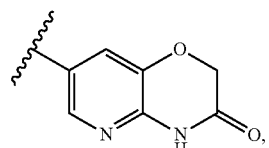 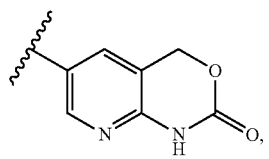

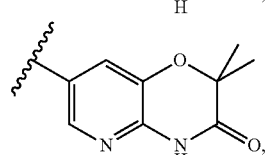

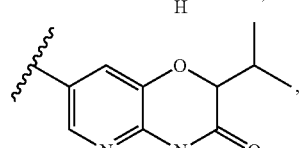

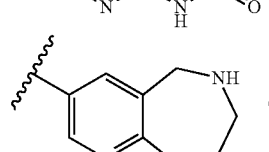 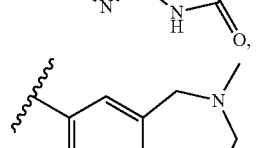

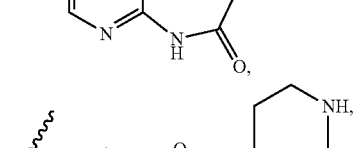

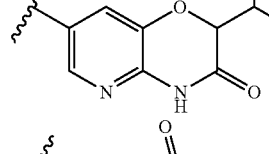

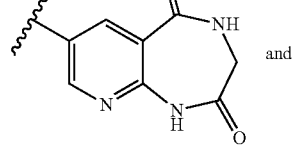

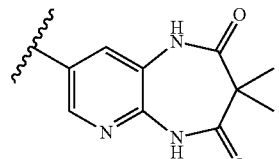

7. The compound as claimed in claim 1 wherein when $R^x$ is moiety (iii), and said $R^x$ is selected from the group consisting of:

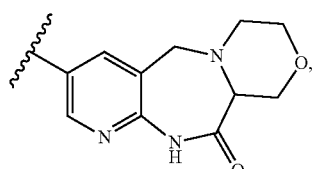

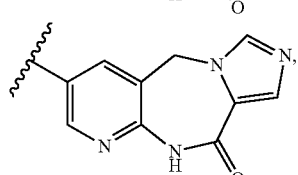

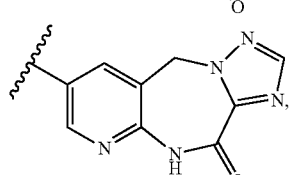

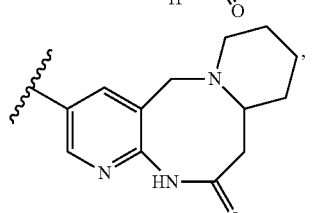

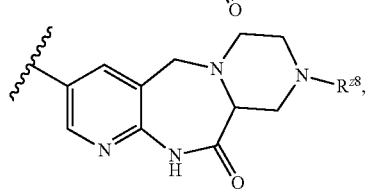

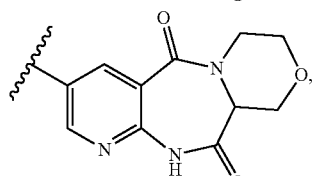

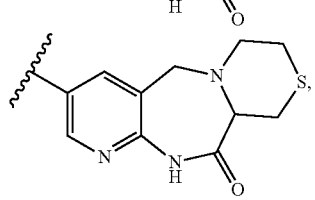

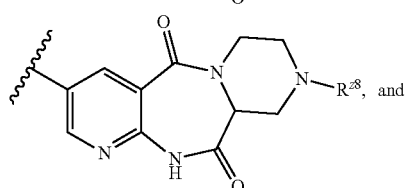

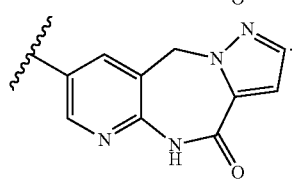

8. A pharmaceutical composition comprising a pharmaceutically acceptable carrier and a therapeutically active amount of a compound as claimed in claim 1.

9. A process for preparing a pharmaceutical composition wherein a therapeutically active amount of a compound as claimed in claim 1 is intimately mixed with a pharmaceutically acceptable carrier.

10. A method of treating a bacterial infection, comprising the administration of a therapeutically effective amount of at least one compound as claimed in claim 1.

11. A method of treating a bacterial infection as claimed in claim 10 wherein said bacterial infection is caused by a bacterium that expresses a FabI enzyme.

12. A process for preparing a compound as claimed in claim 1, comprising:

(i) reacting of a compound of formula (II),

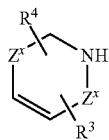

(II)

with a compound of formula (III),

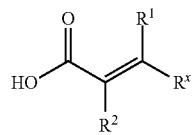

(III)

to yield a compound of formula (IV); and
(ii) coupling of a compound of formula (IV),

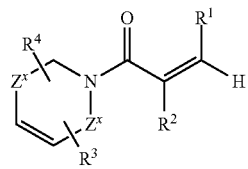

(IV)

with moiety $R^x$, to yield a compound of formula (I).

* * * * *